(12) United States Patent
Walen et al.

(10) Patent No.: US 12,702,518 B2
(45) Date of Patent: Aug. 11, 2026

(54) TRACKER AND RELATED ACCESSORIES FOR A SURGICAL NAVIGATION SYSTEM

(71) Applicant: Stryker European Operations Limited, Carrigtwohill (IE)

(72) Inventors: James G. Walen, Portage, MI (US); Rahul Eapen, Grand Rapids, MI (US); Clifford Edwin Lambarth, Portage, MI (US); Caleb Gossens, Ravenna, MI (US); Fadi Ghanam, Schallstadt (DE); Michael Laubenthal, Mattawan, MI (US); John Andrew Snodgrass, Plainwell, MI (US)

(73) Assignee: Stryker European Operations Limited, Carrigtwohill (IE)

( * ) Notice: Subject to any disclaimer, the term of this patent is extended or adjusted under 35 U.S.C. 154(b) by 532 days.

(21) Appl. No.: 18/278,992

(22) PCT Filed: Feb. 25, 2022

(86) PCT No.: PCT/IB2022/051706

§ 371 (c)(1),
(2) Date: Aug. 25, 2023

(87) PCT Pub. No.: WO2022/180610

PCT Pub. Date: Sep. 1, 2022

(65) Prior Publication Data

US 2024/0130825 A1 Apr. 25, 2024
US 2024/0225775 A9 Jul. 11, 2024

Related U.S. Application Data

(60) Provisional application No. 63/169,088, filed on Mar. 31, 2021, provisional application No. 63/154,273, filed on Feb. 26, 2021.

(51) Int. Cl.
*A61B 90/00* (2016.01)
*A61B 34/20* (2016.01)

(52) U.S. Cl.
CPC .............. *A61B 90/08* (2016.02); *A61B 34/20* (2016.02); *A61B 2034/2055* (2016.02)

(58) Field of Classification Search
None
See application file for complete search history.

(56) References Cited

U.S. PATENT DOCUMENTS 7,725,162 B2 5/2010 Malackowski et al.
8,118,488 B2 2/2012 Gregerson
(Continued)

FOREIGN PATENT DOCUMENTS

WO 2021059253 A2 4/2021
WO 2021084484 A2 5/2021

OTHER PUBLICATIONS

Partial International Search Report for Application No. PCT/IB2022/051706 dated Jul. 5, 2022, 2 pages.
(Continued)

*Primary Examiner* — Yi-Shan Yang
(74) *Attorney, Agent, or Firm* — Howard & Howard Attorneys PLLC

(57) ABSTRACT

An adapter for removably coupling a tracker to a surgical handpiece includes a proximal member having an interface configured to engage and prevent rotation of the proximal member relative to the surgical handpiece, a distal member slidably and rotatably coupled to the proximal member, a biasing member disposed between the proximal distal members and configured to urge the proximal and distal members in opposing directions, and a tracking array mount coupled to the distal member. The biasing member is configured to be compressed by a reference feature of the end effector and
(Continued)

the surgical handpiece when the distal member is disposed on the end effector and the end effector is coupled to the surgical handpiece, the compressed biasing member creating a frictional force between the distal and proximal members that resists rotation of the distal member relative to the proximal member.

20 Claims, 35 Drawing Sheets

(56) References Cited

U.S. PATENT DOCUMENTS

| | | | | |
|---|---|---|---|---|
| 9,008,757 | B2 | 4/2015 | Wu | |
| 9,111,379 | B2 | 8/2015 | Gregerson et al. | |
| 9,119,655 | B2 | 9/2015 | Bowling et al. | |
| 9,801,592 | B2 | 10/2017 | Stanton et al. | |
| 9,962,132 | B2 | 5/2018 | Gregerson | |
| 10,151,810 | B2 | 12/2018 | Gregerson et al. | |
| 10,456,207 | B2 | 10/2019 | Flatt | |
| 10,765,480 | B2 | 9/2020 | Srimohanarajah et al. | |
| 11,819,287 | B2 * | 11/2023 | Lequette | A61B 34/25 |
| 2011/0263971 | A1 * | 10/2011 | Nikou | A61B 90/39<br>600/424 |
| 2014/0275953 | A1 | 9/2014 | Gregerson et al. | |
| 2016/0302871 | A1 | 10/2016 | Gregerson et al. | |
| 2018/0028266 | A1 | 2/2018 | Barnes et al. | |
| 2018/0344304 | A1 | 12/2018 | Lindenmann et al. | |
| 2019/0231447 | A1 | 8/2019 | Ebbitt et al. | |
| 2019/0321108 | A1 | 10/2019 | Ghanam et al. | |
| 2020/0078097 | A1 | 3/2020 | Gregerson et al. | |

OTHER PUBLICATIONS

International Search Report for Application No. PCT/IB2022/051706 dated Aug. 26, 2022, 2 pages.

* cited by examiner 100
102
104
106A
106B
108
112
114
116
118
120
122
124
126
128
130
132A
132B
134
140
142
144
146
144; 146
148
150
152
502
506
1B
LCLZ
P
ST 416A
423A 416A
419A
414
411
410
8B
412
8C
408
427
424
406
422
425

402
404
418
420

418

410
413
412
411

419A
416A
411
410
423A 410
415B
414
415A
411

306
178
314
180
422
406
404
316
312
421
408
420
418
402
310
302
304

208
202
204
410
502
210
404B
408
418
416B
406B
178

408
402B
204
418
428
426
406B
422
178
430

511B
514
515A
515B
506
510B
504
502

513B
511A
512
506
516
503
513A
510A
534
510C
506
532
505
501
516
522
524
511C
516
534
506
511D
510D 512
513B
515A
514
513A
506
511B
515B
511A
510A
506
516
510B
516
502
534
503
19
19
501
504
534
510C
510D
516
511D
506
522
506
511C
516
524

512
513B
514
513A
511A
515
$P_A$
$P_{B, C}$
$P_C$
511B
$P_A$
$P_B$
510C
510B
502
503
501
504

$P_{A, B, C}$
511D
522
510C
$P_A$
$P_C$
$P_B$
510D
511C

TRACKER AND RELATED ACCESSORIES FOR A SURGICAL NAVIGATION SYSTEM

RELATED APPLICATIONS

This application is a National Stage Entry of International Patent Application No. PCT/IB2022/051706, filed Feb. 25, 2022, which claims priority to and all the benefits of U.S. Provisional Patent Application No. 63/154,273, filed Feb. 26, 2021, and U.S. Provisional Patent Application No. 63/169,088, filed Mar. 31, 2021, the disclosures of which are hereby incorporated by reference herein in their entirety.

BACKGROUND

Navigation systems are frequently utilized to assist medical professionals in carrying out various types of surgical procedures, including neurosurgical and orthopedic procedures. To this end, a surgeon may utilize a navigation system to track, monitor, or otherwise locate one or more tools, surgical instruments, and/or portions of a patient's anatomy within a common reference frame. Typically, tools and/or surgical instruments are tracked together with the anatomy, and their relative movement is depicted on a display.

Conventional navigation systems may employ light signals, sound waves, magnetic fields, radio frequency signals, and the like, in order to track the position and/or orientation of objects, such as a surgical instrument or surgical robot relative to the patient and/or surgical site. Often, trackers are attached or otherwise integrated into the objects being tracked. A localizer cooperates with tracking elements (e.g., fiducials, markers, and the like) coupled to the trackers to monitor the trackers, and ultimately to determine a position and/or orientation of the objects being tracked.

For certain procedures, patient-specific imaging data may be acquired intraoperatively using one or more types of imaging systems to help assist the surgeon in visualizing, navigating relative to, and/or treating the anatomy. To this end, navigation systems may cooperate with imaging systems and/or other parts of surgical systems (e.g., surgical tools, instruments, surgical robots, and the like) to track objects relative to a target site of the anatomy.

In certain surgical procedures, such as those performed using a surgical instrument and/or a surgical robot to manipulate biological tissue and/or place an implant in the patient, trackers may be secured to the surgical instrument and/or surgical robot to track the pose of the surgical instrument or surgical robot relative to the target site of the anatomy.

For many types of navigation systems, the surgeon generally considers the visibility of the trackers to the localizer. This can be especially true when the navigation system relies on the optical visibility of the tracking elements of the trackers by the localizer to determine the position and/or orientation of the objects being tracked. Many instrument trackers are configured to be mounted in a fixed or static position to a surgical instrument. However, when a tracker is mounted to a surgical instrument in a fixed or static manner, an object can become positioned between the localizer and the tracker, inhibiting the localizer's visibility of the tracking elements. Accordingly, while trackers and navigation systems have generally worked well for their intended purpose, there remains a need in the art to overcome one or more of the deficiencies described above.

SUMMARY

This Summary introduces a selection of concepts in a simplified form that are further described below in the Detailed Description below. This Summary is not intended to limit the scope of the claimed subject matter nor identify key features or essential features of the claimed subject matter.

In one aspect, an adapter for mounting a tracker to a surgical instrument for use with a surgical navigation system to track the pose of the surgical instrument is provided. The adapter may enable the tracker to be rotated relative to the surgical instrument while maintaining a fixed relationship between the markers of the tracker and a distal end of an end effector of the surgical instrument, allowing the surgical instrument to continue to be tracked via the tracker without recalibrating the system.

In another aspect, a surgical instrument assembly for removably coupling a tracker to a surgical handpiece is provided. The surgical instrument assembly may include an end effector, which may include: a shaft including a distal portion and opposing proximal portion, the distal portion for manipulating biological tissue and the proximal portion defining a coupling feature for removably attaching the end effector to the surgical handpiece; and a reference feature disposed on the shaft between the proximal portion and the distal portion, the reference feature spaced a defined distance from the coupling feature. The assembly may also include an adapter removably couplable to the end effector. The adapter may include: a proximal member that may include a surgical handpiece interface configured to engage the surgical handpiece and prevent rotation of the proximal member relative to the surgical handpiece; a distal member rotatably and slidably coupled to the proximal member, where the distal member further may include a tracking array mount for coupling a tracker to the adapter; and a biasing member positioned to urge the proximal member and the distal member in opposing directions; where the proximal member and the distal member define an aperture through the adapter that is configured to receive the shaft of the end effector. The assembly may also include where the coupling feature and the reference feature of the end effector are spaced along the shaft of the end effector such that the surgical handpiece will engage the proximal member of the adapter and the reference feature will engage the distal member of the adapter when the end effector is coupled to the surgical handpiece causing the biasing member to create a frictional force between the proximal member and the distal member that resists rotation of the distal member relative to the proximal member.

In another aspect, a surgical instrument assembly for removably coupling a tracker to a surgical handpiece is provided. The surgical instrument assembly may include an end effector, which may include: a shaft including a distal portion and opposing proximal portion, the distal portion for manipulating biological tissue and the proximal portion defining a coupling feature for removably attaching the end effector to the surgical handpiece; and a reference feature disposed on the shaft between the proximal portion and the distal portion, the reference feature spaced a defined distance from the coupling feature. The assembly may also include an adapter removably couplable to the end effector. The adapter may include: a proximal member that may include a surgical handpiece interface configured to engage the surgical handpiece and prevent rotation of the proximal member relative to the surgical handpiece; a distal member rotatably and slidably coupled to the proximal member, where the distal member may include a tracking array mount for coupling a tracker to the adapter; where an outer surface distal member includes one of a plurality of recesses arranged annularly about the outer surface or at least one protrusion; where an inner surface of the proximal member that is at least partially disposed over the outer surface includes the other of the at least one protrusion or the plurality of recesses arranged annularly about the inner surface; and where the at least one protrusion is configured to selectively engage the plurality of recesses as the distal member is rotated relative to the proximal member. The assembly may also include where the at least one protrusion and the plurality of recesses configured to create a frictional force between the proximal member and the distal member that that resists rotation of the distal member relative to the proximal member.

In another aspect, a surgical instrument adapter for use with a calibration body including a stop and a retention feature is provided. The surgical instrument adapter includes a proximal member that may include a surgical handpiece interface configured to engage the surgical handpiece and prevent rotation of the proximal member relative to the surgical handpiece. The adapter also includes a distal member slidably and rotatably coupled to the proximal member. The adapter also includes a biasing member disposed between the proximal member and the distal member and configured to urge the proximal member and distal member in opposing directions. The adapter also includes a tracking array mount that may be coupled to the distal member. The adapter also includes a fastening member disposed on the distal member and configured to removably secure the adapter to the calibration body, the fastening member shaped to matingly engage the retention feature of the calibration body such that the distal member abuts the stop of the calibration body to position the adapter at a known distance from a distal end of the calibration body.

In another aspect, a surgical instrument adapter for use with an end effector including a reference feature and an attachment feature for coupling the end effector to a surgical handpiece is provided. The surgical instrument adapter includes a proximal member that may include a surgical handpiece interface configured to engage the surgical handpiece and prevent rotation of the proximal member relative to the surgical handpiece. The adapter also includes a distal member slidably and rotatably coupled to the proximal member. The adapter also includes a biasing member disposed between the proximal member and the distal member and configured to urge the proximal member and distal member in opposing directions. The adapter also includes a tracking array mount that may be coupled to the distal member. The adapter also includes a fastening member disposed on the distal member and configured to removably secure the adapter to the end effector such that the end effector can rotate freely relative to the distal and proximal members. The adapter also includes where the biasing member is configured to be compressed by the reference feature and the surgical handpiece acting upon the distal member and the proximal member when the end effector is coupled to the surgical handpiece, the biasing member creating a friction force between the distal member and the proximal member that resists rotation of the distal member relative to the proximal member. The adapter also includes where the biasing member is configured to be decompressed when the end effector is decoupled from the surgical handpiece, which may allow the distal member to rotate freely relative to the proximal member.

The present disclosure also provides a tracker assembly for tracking a surgical instrument with a surgical navigation system. The tracker assembly includes a tracking array which may include: an array base, a first leg extending distally from the array base, and a first marker identifiable by the surgical navigation system coupled to the first leg proximate a distal end of the first leg. The assembly also includes a tracking array mount for securing the tracking array to a surgical instrument. The tracking array mount may include: a base defining a mounting surface; and a first tab disposed above the mounting surface a distance greater than a thickness of the array base. The first tab may include an angled surface configured to urge the array base toward the mounting surface when the distal end of the first leg of the array base is disposed between the first tab and the mounting surface.

In another aspect, a tracking array mount system for securing a tracking array to a surgical tool is provided. The tracking array mount system includes a base defining a mounting surface. The system also includes a first tab disposed above the mounting surface. The first tab may include an angled surface configured to urge the tracking array toward the mounting surface. The system also includes a second tab disposed above the mounting surface. The second tab may include a pair of angled surfaces configured to provide two contact points on opposing edges of the tracking array to inhibit rotation of the tracking array relative to the mounting surface. The system also includes a biasing member configured to urge the tracking array toward the first tab and the second tab to removably couple the tracking array to the tracking array mount.

In another aspect, a surgical instrument tracking system for use with a surgical handpiece is provided. The surgical instrument tracking system includes a first end effector that may include: a first shaft including a distal portion and opposing proximal portion, the proximal portion defining a first coupling feature for removably attaching the first end effector to the surgical handpiece; and a first reference feature disposed on the first shaft a defined distance from the first coupling feature. The system also includes a second end effector that may include: a second shaft including a distal portion and opposing proximal portion, the proximal portion defining a second coupling feature for removably attaching the second end effector to the surgical handpiece; and a second reference feature disposed on the second shaft a defined distance from the second coupling feature. The system also includes an adapter configured to removably couple to the first end effector and the second end effector. The adapter may include: a proximal member that may include a surgical handpiece interface configured to engage the surgical handpiece and prevent rotation of the proximal member relative to the surgical handpiece, a distal member slidably and rotatably coupled to the proximal member, a fastening member disposed on the distal member and configured to removably couple the adapter to the proximal portion the first end effector and the second end effector, and a biasing member disposed between the proximal member and the distal member and configured to urge the proximal member and distal member in opposing directions. The system also includes where the first coupling feature of the first end effector is configured such that the surgical handpiece will engage the proximal member of the adapter when the first end effector is coupled to the surgical handpiece causing the biasing member to urge the distal member against the first reference feature to position the adapter at a first known distance from the distal portion of the first end effector. The system also includes where the second coupling feature of the second end effector is configured such that the surgical handpiece will engage the proximal member of the adapter when the second end effector is coupled to the surgical handpiece causing the biasing member to urge the distal member against the second reference feature to position the adapter at a second known distance from the distal portion of the second end effector.

In another aspect, a method of calibrating a surgical instrument adapter with a navigation system is provided. The method of calibrating includes coupling a surgical instrument adapter including a tracking array to a calibration body. The method also includes observing the calibration body with a surgical navigation system while the tracking array is in view of the surgical navigation system to calibrate a position of tracking array relative to the surgical instrument adapter. The method also includes removing the surgical instrument adapter from the calibration body. The method also includes coupling the surgical instrument adapter including the tracking array to an end effector. The method also includes coupling the end effector to a surgical handpiece such that a surgical handpiece engages the surgical instrument adapter causing a biasing member of the surgical adapter to position the surgical adapter adjacent a reference feature of the end effector so that the tracking array of the surgical instrument adapter is positioned at a known position relative to a distal end of the end effector.

In another aspect, a surgical instrument assembly for navigating a surgical end effector is provided. The surgical instrument assembly includes a surgical handpiece. The assembly also includes an end effector that includes a shaft having a distal portion and opposing proximal portion, the distal portion for manipulating biological tissue and the proximal portion defining a coupling feature for removably attaching the end effector to a surgical handpiece; and a reference feature disposed on the shaft between the proximal portion and the distal portion, the reference feature spaced a defined distance from the coupling feature. The assembly also includes an adapter removably couplable to the end effector, where the adapter may include: a proximal member that may include a surgical handpiece interface configured to engage the surgical handpiece and prevent rotation of the proximal member relative to the surgical handpiece; a distal member rotatably and slidably coupled to the proximal member, where the distal member may include a tracking array mount for coupling a tracker to the adapter; and a biasing member positioned to urge the proximal member and the distal member in opposing directions, where the proximal member and the distal member define an aperture through the adapter that is configured to receive the shaft of the end effector. The assembly also includes where the surgical handpiece is configured to engage the proximal member when the adapter is disposed on the end effector and the end effector is coupled to the surgical handpiece such that the biasing member urges the distal member against the reference feature to position the tracking array mount at a known distance from the distal portion of the end effector, and the adapter is configured to allow the distal member and the tracking mount to rotate about the shaft of the end effector.

In another aspect, a surgical instrument assembly for removably coupling a tracker to a surgical handpiece is provided. The surgical instrument assembly includes a surgical handpiece. The assembly also includes an end effector that may include: a shaft including a distal portion and opposing proximal portion, the distal portion for manipulating biological tissue and the proximal portion defining a coupling feature for removably attaching the end effector to the surgical handpiece; and a reference feature disposed on the shaft between the proximal portion and the distal portion, the reference feature spaced a defined distance from the coupling feature. The assembly also includes an adapter removably couplable to the end effector, where the adapter may include: a proximal member that may include a surgical handpiece interface configured to engage the surgical handpiece and prevent rotation of the proximal member relative to the surgical handpiece; a distal member rotatably and slidably coupled to the proximal member, where the distal member further may include a tracking array mount for coupling a tracker to the adapter; and a biasing member positioned to urge the proximal member and the distal member in opposing directions; where the proximal member and the distal member define an aperture through the adapter that is configured to receive the shaft of the end effector. The assembly also includes where the surgical handpiece is configured to engage the proximal member when the adapter is disposed on the end effector and the end effector is coupled to the surgical handpiece such that the biasing member is configured to urge the distal member against the reference feature positioning the adapter at a known distance from the distal portion of the end effector.

In another aspect, a surgical instrument adapter for use with an end effector including a reference feature and an attachment feature for coupling the end effector to a surgical handpiece is provided. The surgical instrument adapter includes a proximal member that may include a surgical handpiece interface configured to engage the surgical handpiece and prevent rotation of the proximal member relative to the surgical handpiece. The adapter also includes a distal member slidably and rotatably coupled to the proximal member. The adapter also includes a biasing member disposed between the proximal member and the distal member and configured to urge the proximal member and distal member in opposing directions. The adapter also includes a tracking array mount that may be coupled to the distal member. The adapter also includes a fastening member disposed on the distal member and configured to removably secure the adapter to the end effector such that the end effector can rotate freely relative to the distal and proximal members. The adapter also includes where the biasing member is configured position the distal member adjacent the reference feature of the end effector when the surgical handpiece interface engages the surgical handpiece to position the adapter and tracking array mount at a known position on the end effector.

In another aspect, a surgical instrument adapter for removably coupling a tracker to a surgical instrument including an end effector and a surgical handpiece is provided. The surgical instrument adapter includes a proximal member that includes a surgical handpiece interface configured to engage the surgical handpiece and prevent rotation of the proximal member relative to the surgical handpiece. The adapter also includes a distal member rotatably and slidably coupled to the proximal member, where the distal member further may include a tracking array mount for coupling a tracker to the adapter, and where the proximal member and the distal member define an aperture through the adapter that is configured to receive the end effector. The adapter also includes a biasing member disposed between the proximal member and the distal member and configured to urge the proximal member and distal member in opposite directions. The adapter also includes a tapered washer disposed between the biasing member and the proximal member and including a beveled surface configured to contact a reciprocal surface of the proximal member to create a sliding friction that resists rotation of the distal member relative to the proximal member when the adapter is disposed on the end effector and the surgical handpiece interface of the proximal member is engaged with the surgical handpiece.

In another aspect, a surgical instrument assembly for removably coupling a tracker to a surgical handpiece is provided. The surgical instrument assembly includes an end effector having a shaft with a distal portion and opposing proximal portion, the distal portion for manipulating biological tissue and the proximal portion defining a coupling feature for removably attaching the end effector to the surgical handpiece. The assembly also includes an adapter removably couplable to the end effector. The adapter includes a proximal member that includes a surgical handpiece interface configured to engage the surgical handpiece and prevent rotation of the proximal member relative to the surgical handpiece. The adapter also includes a distal member rotatably and slidably coupled to the proximal member, where the distal member further may include a tracking array mount for coupling a tracker to the adapter, and where the proximal member and the distal member define an aperture through the adapter that is configured to receive the end effector. The adapter also includes a biasing member disposed between the proximal member and the distal member and configured to urge the proximal member and distal member in opposite directions. The adapter also includes a tapered washer disposed between the biasing member and the proximal member and including a beveled surface configured to contact a reciprocal surface of the proximal member to create a sliding friction that resists rotation of the distal member relative to the proximal member when the adapter is disposed on the end effector and the surgical handpiece interface of the proximal member is engaged with the surgical handpiece.

In another aspect, a tracker array for tracking a surgical object is provided. The tracker array includes a body. The array also includes first, second, and third light sources secured to the body and arranged in a pattern for being recognized by a navigation system to track the surgical object. The array also includes a battery mount secured to the body and including battery contacts for engaging a battery and communicating electrical energy from the battery to the first, second, and third light sources when the battery is secured to the battery mount. The array also includes a control circuit coupled to the battery and to the first, second, and third light sources, the control circuit being configured to limit current through each of the first, second, and third light sources to less than 20 milliamps.

In another aspect, a tracker array for tracking a surgical object is provided. The tracker array includes a body. The array also includes first, second, and third light sources secured to the body and arranged in a pattern for being recognized by a navigation system to track the surgical object. The array also includes a battery mount secured to the body and including battery contacts for engaging a battery and communicating electrical energy from the battery to the first, second, and third light sources when the battery is secured to the battery mount. The array also includes a control circuit coupled to the battery and to the first, second, and third light sources, the control circuit being configured to limit an intensity of each of the first, second, and third light sources to less than 40 w/sr.

In another aspect, a tracker array for tracking a surgical object is provided. The tracker array includes a board including a first face and an opposed second face. The array also includes first, second, and third light sources disposed on the first face of the board and arranged in a pattern for being recognized by a navigation system to track the surgical object. The array also includes a battery mount disposed on the second face of the board and including battery contacts for engaging a battery and communicating electrical energy from the battery to the first, second, and third light sources when the battery is secured to the battery mount.

In another aspect, a disposable tracker for tracking a surgical object during a surgical procedure is provided, the disposable tracker being removably couplable to a tracker mount secured to the surgical object, the tracker mount defining a star-shaped recess for receiving the disposable tracker, the star-shaped recess including first, second, and third leg recesses that extend distally from a central portion of the star-shaped recess. The disposable tracker includes a body having a shape conforming to the star-shaped recess, the body including first, second, and third portions for being positioned adjacent distal end portions of the first, second, and third leg recesses respectively when the disposable tracker is secured to the tracker mount. The tracker also includes first, second, and third light sources disposed on the first, second, and third portions respectively and arranged in a pattern for being recognized by a navigation system to track the surgical object. The tracker also includes a battery mounted to the body and in electrical communication with the first, second, and third light sources. The tracker also includes where the disposable tracker is configured for single use.

In another aspect, a tracking array that is removably couplable to a tracking array mount for tracking a surgical object using a navigation system is provided. The tracking array includes a circuit board defining a central body portion and a plurality of legs extending from the central body portion, the plurality of legs including a first leg, a second leg, a third leg, and a fourth leg, the circuit board including a first face, and a second face, the first face being opposite the second face. The array also includes the central body portion having a center and defining an alignment aperture, the alignment aperture offset from the center of the central body portion. The array also includes a first light source coupled to the first leg, a second light source coupled to the second leg, a third light source coupled to the third leg, and a fourth light source coupled to the fourth leg, where the first, the second, the third light source, and the fourth light source extend from the first face of the circuit board. The array also includes a control circuit coupled to the circuit board. The array also includes a plurality of electrical traces printed on the circuit board, and connected to the first, second, third, and fourth light sources, and the control circuit. The array also includes a battery mount shaped to engage a battery, the battery mount coupled to the second face of the circuit board and in electrical communication with each of the light sources. The array also includes where the first leg, the second leg, the third leg, and the fourth leg each includes a foot portion at a distal end of the respective leg, the foot portions of the third leg and the fourth leg being shaped to align the tracking array with a tracking array mount. The array also includes a protrusion extending from the central body portion between the third leg and the fourth leg, the protrusion protruding from the central body portion for a length less than the length the third and fourth legs protrude from the central portion.

In another aspect, a tracking array for tracking a surgical object is provided. The tracking array includes a base defining a central portion and a plurality of legs extending from the central portion, the plurality of legs including a first leg, a second leg, a third leg, and a fourth leg, and the base including a first face and a second face, the first face being opposite the second face. The array also includes the central portion having a center and defining an alignment aperture, the alignment aperture offset from the center of the central body portion. The array also includes a first light source coupled to the first leg, a second light source coupled to the second leg, a third light source coupled to the third leg, and a fourth light source coupled to the fourth leg, where the first, the second, the third and the fourth light sources are disposed on the first face of the base. The array also includes a control circuit coupled to the base. The array also includes an electrical conductor coupled to the base and connected to the first light source and the control circuit. The array also includes a battery mount including a plurality of battery contacts shaped to engage a battery upon coupling of the battery to the battery mount, the battery mount coupled to the second face of the base. The array also includes where the first leg, the second leg, the third leg, and the fourth leg each includes a foot portion at a distal end of the respective leg, the foot portion of the third leg and the fourth leg being shaped to align the tracking array with a tracking array mount. The array also includes a protrusion extending from the central portion of the base between the third leg and the fourth leg, the protrusion protruding from the central portion for a length less than the length the third and fourth legs protrude from the central portion.

In another aspect, a package of tracking arrays for use with a surgical navigation system to identify a pose of one or more surgical objects is provided. The package of tracking arrays includes a package that may include a first portion and a second portion, the package defining a sterile volume, and the first portion and second portion separable from one another to provide access to the sterile volume. The package of tracking arrays also includes a first tracking array including a first light source, second light source, third light source, and a fourth light source coupled to the first tracking array, the first tracking array disposed within the sterile volume, where the first tracking array may include a battery. The package of tracking arrays also includes a second tracking array including a first light source, second light source, third light source, and a fourth light source coupled to the second tracking array, where the second tracking array may include a second battery. The package of tracking arrays also includes where each of the first tracking array and the second tracking array include a circuit board including a first leg, a second leg, a third leg, and a fourth leg. The package of tracking arrays also includes where the first light source of each of the first tracking array and the second tracking array is disposed on the first leg at a reference location. The package of tracking arrays also includes where the second light source, the third light source, and the fourth light source of the first tracking array are arranged to define a plurality of triangles using the first light source of the first tracking array and any two of the second light source, the third light source, and the fourth light source of the first tracking array as a first pattern that is identifiable by the surgical navigation system. The package of tracking arrays also includes where the second light source, the third light source, and the fourth light source of the second tracking array are arranged to define a plurality of triangles using the first light source of the second tracking array and any two of the second light source, the third light source, and the fourth light source of the second tracking array as a second pattern that is identifiable by the surgical navigation system. The package of tracking arrays also includes where the first pattern is distinguishable by the navigation system from the second pattern to allow the surgical navigation system to distinguish between each of one or more surgical objects that the first tracking array and the second tracking array are coupled to.

In another aspect, a method of attaching a tracking array to a tracker mount of surgical object for use with a surgical navigation system is provided. The method includes providing a tracking array that may include a central body portion, a plurality of legs extending from the central body portion, each of the plurality of legs including a foot portion located spaced apart from the central body portion, and a plurality of light sources coupled to the plurality of legs. The method also includes inserting the foot portions of two of the plurality of legs within respective recesses of the tracker mount of the surgical object. The method also includes manipulating a locking mechanism of the tracker mount to removably secure the tracker array to the tracker mount after the foot portions are inserted within the respective recesses of the tracker mount.

In another aspect, a method of manufacturing a kit of tracking arrays is provided. The method includes providing at least two circuit boards. Each of the circuit boards may include a central body portion and a plurality of legs extending from the central body portion arranged such that each of the at least two circuit boards may include a generally identical shape. The method also includes attaching three or more light sources to a first of the at least two circuit boards, each of the three or more light sources coupled to one of the plurality of legs extending from the central body portion to define a first pattern. The method also includes attaching three or more light sources to a second of the at least two circuit boards, each of the three or more light sources coupled to one of the plurality of legs extending from the central body portion to define a second pattern. The method also includes packaging the first and second of the at least two circuit boards in a single sterile container in preparation for use during a surgical procedure including two or more surgical objects, each of which utilizes a universal tracker mount configured to receive the first circuit board or the second board to allow a navigation system to distinguish between each of the two or more surgical objects.

In another aspect, a tracking array for tracking a surgical object using a navigation system is provided. The tracking array includes a central body portion and a plurality of legs extending from the central body portion, the plurality of legs including a first leg, a second leg, a third leg, and a fourth leg, and the central body portion including a first face and a second face, the first face being opposite the second face. The array also includes the central body portion having a center and defining an alignment aperture, the alignment aperture offset from the center of the central body portion. The array also includes a first light source coupled to the first leg, a second light source coupled to the second leg, a third light source coupled to the third leg, and a fourth light source coupled to the fourth leg, where the first, the second, the third, and the fourth light sources are disposed on the first face of the central body portion. The array also includes a control circuit in communication with the first, second, third, and fourth light sources and configured to limit the current to the light sources such that the first, second, third, and fourth lights sources emit light at an intensity capable of being observed by the navigation system. The array also includes a battery mount shaped to engage a battery, the battery mount coupled to the second face of the central body portion. The array also includes where each of the first leg, the second leg, the third leg, and the fourth leg includes a foot portion at a distal end of the respective leg, the foot portions of the first leg and the second leg being shaped to align the tracking array with a tracking array mount. The array also includes a protrusion extending from the central body portion between the third leg and the fourth leg, the protrusion protruding from the central body portion for a length less than the length the third and fourth legs protrude from the central body portion.

In another aspect, a tracking array removably couplable to a tracking array mount for use with a navigation system to identify a pose of a surgical instrument is provided. The tracking array includes a circuit board including a first surface and an opposed second surface, the circuit board shaped to define a first leg, a second leg, and a third leg. The array also includes a first light source disposed on the first surface of the first leg. The array also includes a second light source disposed on the first surface of the second leg. The array also includes a third light source disposed on the first surface of the third leg. The array also includes a battery mount disposed on the second surface of the circuit board, the battery mount including battery terminals in electrical communication with each of the first light source, the second light source, and the third light source. The array also includes where a combination of the first light source, the second light source, and the third light source are configured to define a visual indicia specific to the surgical instrument and identifiable by the navigation system.

In another aspect, a tracking array for tracking a surgical object using a navigation system is provided. The tracking array includes a central body portion and a plurality of legs extending from the central body portion, the plurality of legs including a first leg, a second leg, a third leg, and a fourth leg, and the central body portion including a first face, and a second face, the first face being opposite the second face. The array also includes the central body portion having a center and defining an alignment aperture, the alignment aperture offset from the center of the central body portion. The array also includes a first light source coupled to the first leg, a second light source coupled to the second leg, a third light source coupled to the third leg, and a fourth light source coupled to the fourth leg, where the first, the second, the third, and the fourth light sources are disposed on the first face of the central body portion. The array also includes a control circuit in communication with the first, second, third, and fourth light sources and configured to limit the current to the light sources such that the first, second, third, and fourth lights sources emit light at an intensity capable of being observed by the navigation system. The array also includes a battery mount shaped to engage a battery and coupled to the second face of the central body portion. The array also includes where each of the first leg, the second leg, the third leg, and the fourth leg includes a foot portion at a distal end of the respective leg, the foot portions of the first leg and the second leg being shaped to align the tracking array with a tracking array mount.

In another aspect, a tracking array for tracking a surgical object is provided. The tracking array includes a base defining a central portion and a plurality of legs extending from the central portion, the plurality of legs including a first leg, a second leg, a third leg, and a fourth leg, and the base including a first face and a second face, the first face being opposite the second face. The array also includes a first light source coupled to the first leg, a second light source coupled to the second leg, a third light source coupled to the third leg, and a fourth light source coupled to the fourth leg, where the first, the second, the third and the fourth light sources are disposed on the first face of the base. The array also includes a control circuit coupled to the base. The array also includes an electrical conductor coupled to the base and connected to the first light source and the control circuit. The array also includes a battery mount including a plurality of battery contacts shaped to engage a battery upon coupling of the battery to the battery mount, the battery mount coupled to the second face of the base. The array also includes where the first leg, the second leg, the third leg, and the fourth leg each includes a foot portion at a distal end of the respective leg, the foot portions of the third leg and the fourth leg being shaped to align the tracking array with a tracking array mount. The array also includes where the foot portion of at least one of the first leg or the second leg may include an indicia that distinguishes the foot portion from the remaining portion of the base.

Any of the above aspects may be combined in-whole or in part, and any of the aspects above may be utilized with any one or more of the implementations described in the following description, clauses, and claims, whether utilized individually or in combination.

It will be appreciated that one or more of the configurations depicted throughout the drawings may have certain components, structural features, and/or assemblies removed, depicted schematically, and/or shown in phantom for illustrative purposes.

DETAILED DESCRIPTION

The present disclosure describes that it may be advantageous for a tracker to be repositionable about a tracked object to allow the localizer to maintain visibility of the tracking elements of the tracker irrespective of the position of the object. Mounting a repositionable tracker to a surgical instrument with moving components that still allows the navigation system to accurately determine the position and/or orientation of the surgical instrument irrespective of the position of the tracker is not without its difficulties. For example, a device utilized to mount the tracker to the surgical instrument in this manner may include an increased number of components that can add weight, making the surgical instrument heavy and more difficult for the surgeon to manipulate. Furthermore, maintaining spatial positioning of the tracker relative to the surgical instrument as it is repositioned generally requires that the device for mounting the tracker includes a complex arrangement of components that can be difficult to manufacture and/or assemble, adding cost and time.

Figure 1A:
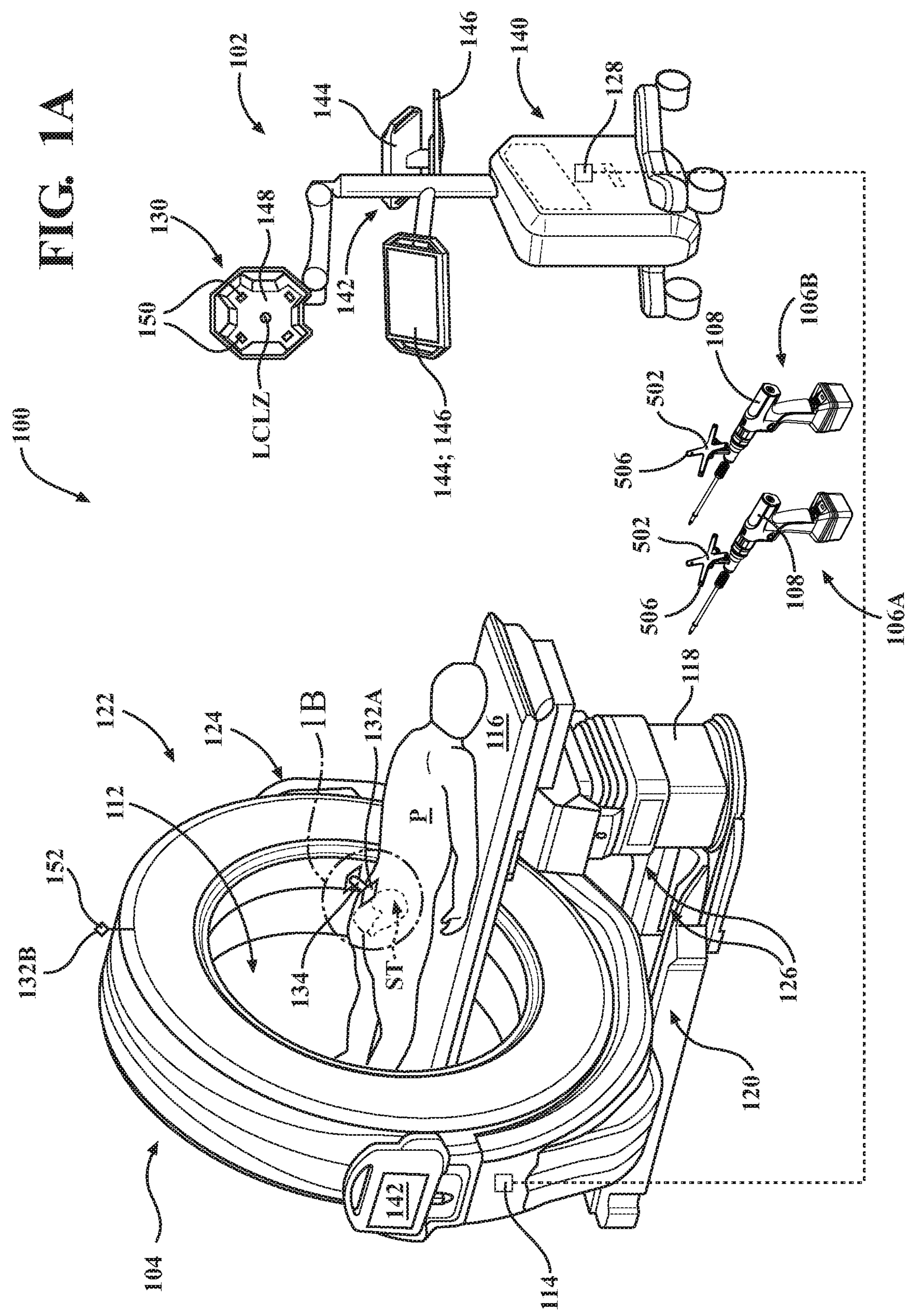
FIG. 1A is a perspective view of a surgical system shown comprising a navigation system and an imaging system supporting a patient with a rotation adapter secured to a surgical instrument according to configurations of the present disclosure.

Referring now to the drawings, wherein like numerals indicate like or corresponding parts throughout the several views, a surgical system 100 is shown in FIG. 1A for treating a patient P. To this end, the illustrated surgical system 100 generally includes a navigation system 102, an imaging system 104, and one or more types of surgical instruments 106. As will be appreciated from the subsequent description below, the surgical system 100 is configured to, among other things, allow the surgeon to visualize, approach, and treat or otherwise manipulate anatomy of a patient P at a target site ST with a high level of control. To this end, imaging data of the target site ST may be acquired via the imaging system 104, and can be used to assist the surgeon in visualizing the patient's P anatomy at or otherwise adjacent to the target site ST. Here, the imaging data may also be utilized by the navigation system 102 to, among other things, facilitate navigation of surgical instruments 106 relative to the target site ST. Each of the components of the surgical system 100 introduced above will be described in greater detail below.

In FIG. 1A, an operating room is shown with a patient P undergoing an exemplary surgical procedure performed using the surgical system 100. In this illustrative example, a minimally-invasive spinal surgical procedure, such as a posterior interbody spinal fusion, is being performed. It will be appreciated that this example is intended to be illustrative, and that other types of surgical procedures are contemplated. During the surgical procedure, one or more hand-held surgical instruments 106 including a powered surgical handpiece 108 and/or a manual surgical tool (not shown) may be used by the surgeon. As noted above and as is described in greater detail below, the navigation system 102 may be configured to track states of one or more of the surgical instruments 106 relative to the target site ST. In this exemplary surgical procedure, powered surgical handpiece 108 may be employed as a cutting or drilling tool to remove tissue, form pilot holes (e.g., in the ilium, in vertebrae, and the like), or otherwise approach the target site ST. The powered surgical handpiece 108 may also be used to drive or otherwise install implantable components (e.g., pedicle screws, anchors, and the like).

For illustrative purposes, generically-depicted surgical instruments 106A, 106B configured for hand-held use are shown in FIG. 1A. However, as will be appreciated from the subsequent description below, aspects of the surgical system 100 may be used with any suitable type of surgical instrument 106 without departing from the scope of the present disclosure. For example, in addition to hand-held surgical instruments 106 of various types and configurations, aspects of the surgical system 100 may also be employed in connection with surgical instruments that may be controlled, guided, positioned, or otherwise manipulated with one or more types of surgical robots. Certain types of surgical robots are disclosed in U.S. Pat. No. 9,119,655, entitled "Surgical Robotic arm Capable of Controlling a Surgical Instrument in Multiple Modes;" U.S. Pat. No. 10,456,207, entitled "Systems and Tools for use with Surgical Robotic Manipulators;" U.S. Patent Application Publication No. 2019/0231447, entitled "End Effectors And Methods For Driving Tools Guided By Surgical Robotic Systems;" U.S. Patent Application Publication No. 2016/0302871, entitled "Integrated Medical Imaging and Surgical Robotic System;" and U.S. Patent Application Publication No. 2020/0078097, entitled "Methods and Systems for Robot-Assisted Surgery," the disclosures of each of which are hereby incorporated by reference in their entirety.

As noted above, the imaging system 104 may be used to obtain imaging data of the patient P, which may be a human or animal patient. In the representative configuration illustrated in FIG. 1, the imaging system 104 is realized as an x-ray computed tomography (CT) imaging device. Here, the patient P may be positioned within a central bore of the imaging system 104 and an x-ray source and detector may be rotated around the central bore 112 to obtain raw x-ray imaging data ID of the patient P. The imaging data ID may be processed using an imaging system controller 114, or another suitable controller, in order to construct three-dimensional imaging data ID, two-dimensional imaging data ID, and the like, which may be transmitted to or otherwise utilized by the navigation system 102 or other components of the surgical system 100.

In some configurations, the imaging data may be obtained preoperatively (e.g., prior to performing a surgical procedure) or intraoperatively (e.g., during a surgical procedure) by positioning the patient P within the central bore of the imaging system 104. In order to obtain the imaging data, a portion of the imaging system 104 may be moved relative to a patient support 116 (e.g., a surgical table) on which the patient P is disposed while the patient P remains stationary. Here, the patient support 116 is secured to the imaging system 104, such as via a column 118 which is mounted to a base 120 of the imaging system 104. A portion of the imaging system 104 (e.g., an O-shaped imaging gantry 122) which includes at least one imaging component may be supported by an articulable support 124 that can translate along the length of the base 120 on rails 126 to perform an imaging scan of the patient P, and may translate away from the patient P to an out-of-the-way position for performing a surgical procedure on the patient P.

An example imaging system 104 that may be used in various configurations is the AIRO® intra-operative CT system manufactured by Mobius Imaging, LLC. Examples of x-ray CT imaging devices that may be used according to various configurations of the present disclosure are described in U.S. Pat. No. 10,151,810, entitled "Pivoting Multi-directional X-ray Imaging System with a Pair of Diametrically Opposite Vertical Support Columns Tandemly Movable Along a Stationary Base Support;" U.S. Pat. No. 9,962,132, entitled "Multi-directional X-ray Imaging System with Single Support Column;" U.S. Pat. No. 9,801,592, entitled "Caster System for Mobile Apparatus;" U.S. Pat. No. 9,111,379, entitled "Method and System for X-ray CT Imaging;" U.S. Pat. No. 8,118,488, entitled "Mobile Medical Imaging System and Methods;" and U.S. Patent Application Publication No. 2014/0275953, entitled "Mobile X-ray Imaging System," the disclosures of each of which are hereby incorporated by reference in their entirety.

While the illustrated imaging system 104 is realized as an x-ray CT imaging device as noted above, in other configurations, the imaging system 104 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. Other configurations are contemplated. In some configurations, the imaging system 104 may be a mobile CT device that is not attached to the patient support 116 and may be wheeled or otherwise moved over the patient P and the patient support 116 to perform a scan. Examples of mobile CT devices include the BodyTom® CT scanner from Samsung Electronics Co., Ltd. and the O-arm® surgical imaging system form Medtronic, plc. The imaging system 104 may also be a C-arm x-ray fluoroscopy device. In other configurations, the imaging system 104 may be a fixed-bore imaging device, and the patient P may be moved into the bore of the device, either on a patient support 116 or on a separate patient table that is configured to slide in and out of the central bore 112. Further, although the imaging system 104 shown in FIG. 1 is located close to the patient P within the operating room, the imaging system 104 may be located remotely, such as in another room or building (e.g., in a hospital radiology department).

The surgical system 100 employs the navigation system 102 to, among other things, track movement of various objects, such as the surgical instruments 106 and parts of the patient's P anatomy (e.g., tissue at the surgical site ST), as well as portions of the imaging system 104 in some configurations. To this end, the navigation system 102 comprises a navigation controller 128 coupled to a localizer 130 that is configured to sense the position and/or orientation of trackers 132A, 132B, 502 within a localizer coordinate system LCLZ. As is described in greater detail below, the trackers 132A, 132B, 502 (also referred to herein as "navigable trackers" and "tracker arrays") are fixed, secured, or otherwise attached to specific objects, and are configured to be monitored by the localizer 130.

The navigation controller 128 is disposed in communication with the localizer 130 and gathers position and/or orientation data for each tracker 132A, 132B, 502 sensed by the localizer 130 in the localizer coordinate system LCLZ. The navigation controller 128 may be disposed in communication with an imaging system controller 114 of the imaging system 104 (e.g., to receive imaging data) and/or in communication with other components of the surgical system 100 (e.g., robotic arm controllers, tool controllers, and the like; not shown). However, other configurations are contemplated. The controllers 114, 128 may be realized as computers, processors, control units, and the like, and may be discrete components, may be integrated, and/or may otherwise share hardware.

It will be appreciated that the localizer 130 can sense the position and/or orientation of multiple trackers 132A, 132B, 502 to track multiple objects within the localizer coordinate system LCLZ. By way of example, and as is depicted in FIG. 1A, trackers 132A, 132B, 502 may comprise a tool tracker 502, an imaging system tracker 132B, a first patient tracker 132A, as well as additional patient trackers, trackers for additional medical and/or surgical tools, and the like.

Figure 1B:
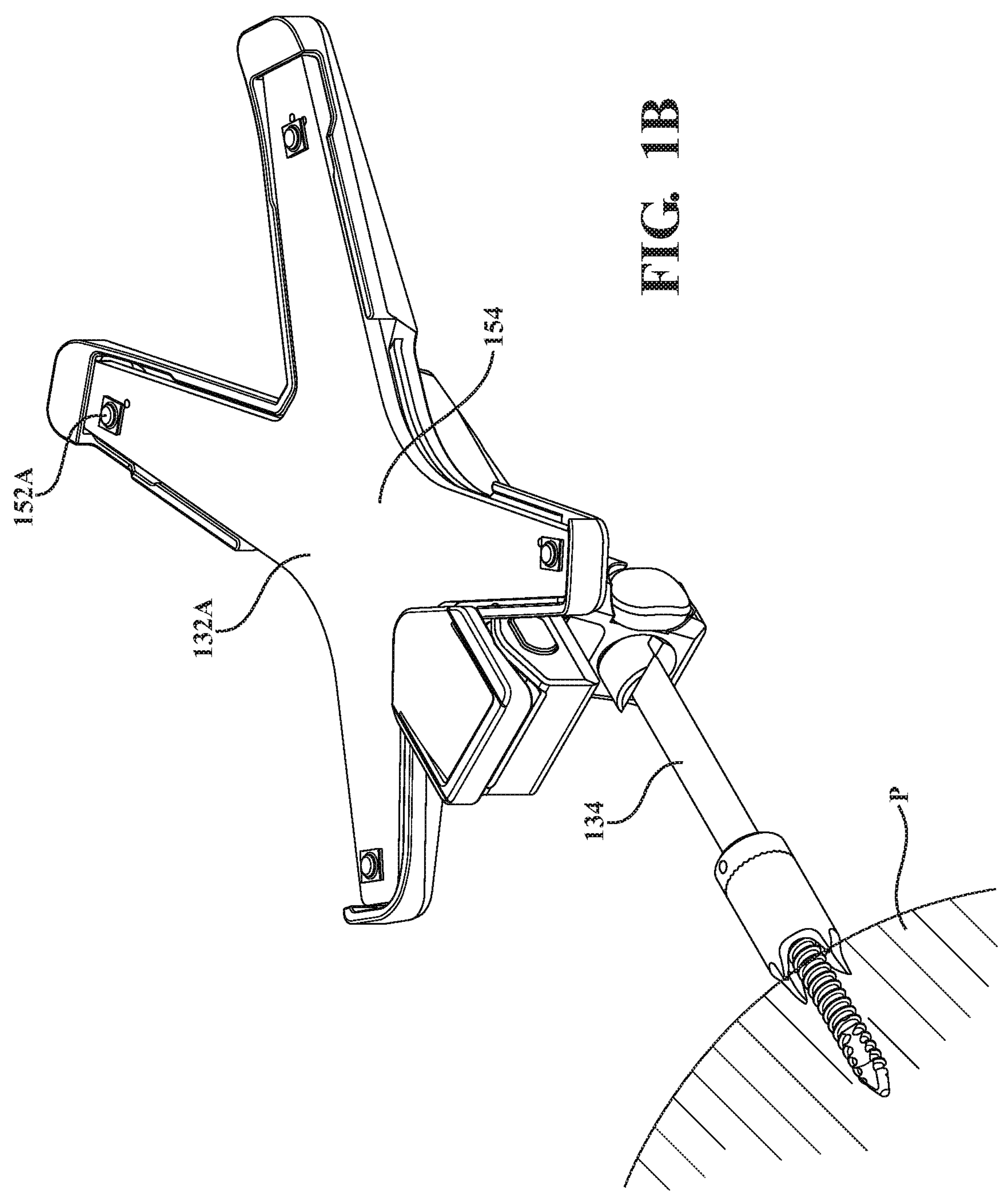
FIG. 1B is a perspective view of a patient tracker and patient anchor for use as part of the surgical system of FIG. 1B.
Figure 2A:
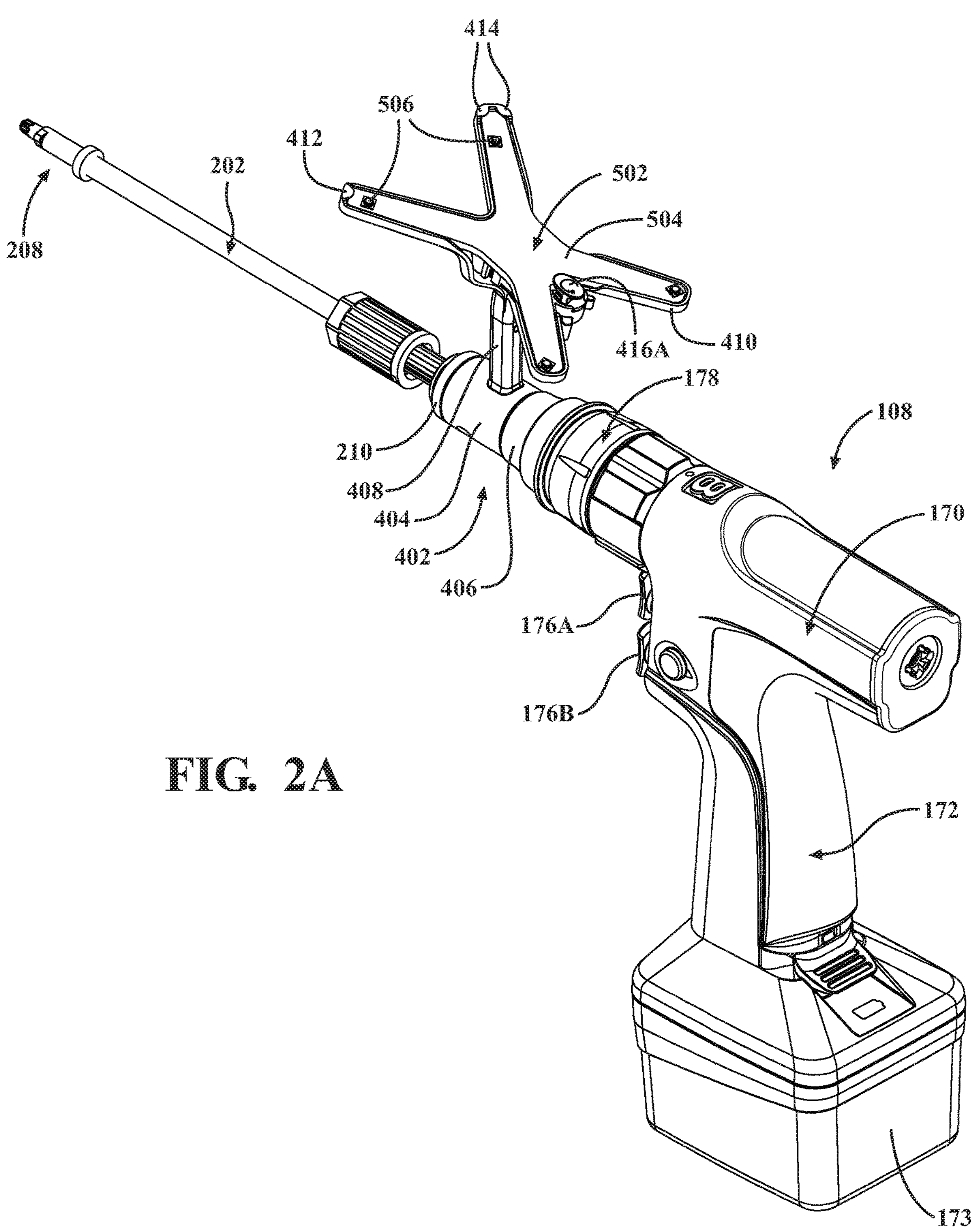
FIG. 2A is a perspective view of a surgical instrument including a surgical handpiece, an end effector, and a rotational adapter for attaching a tracker to the end effector for navigating the surgical instrument.
Figure 2B:
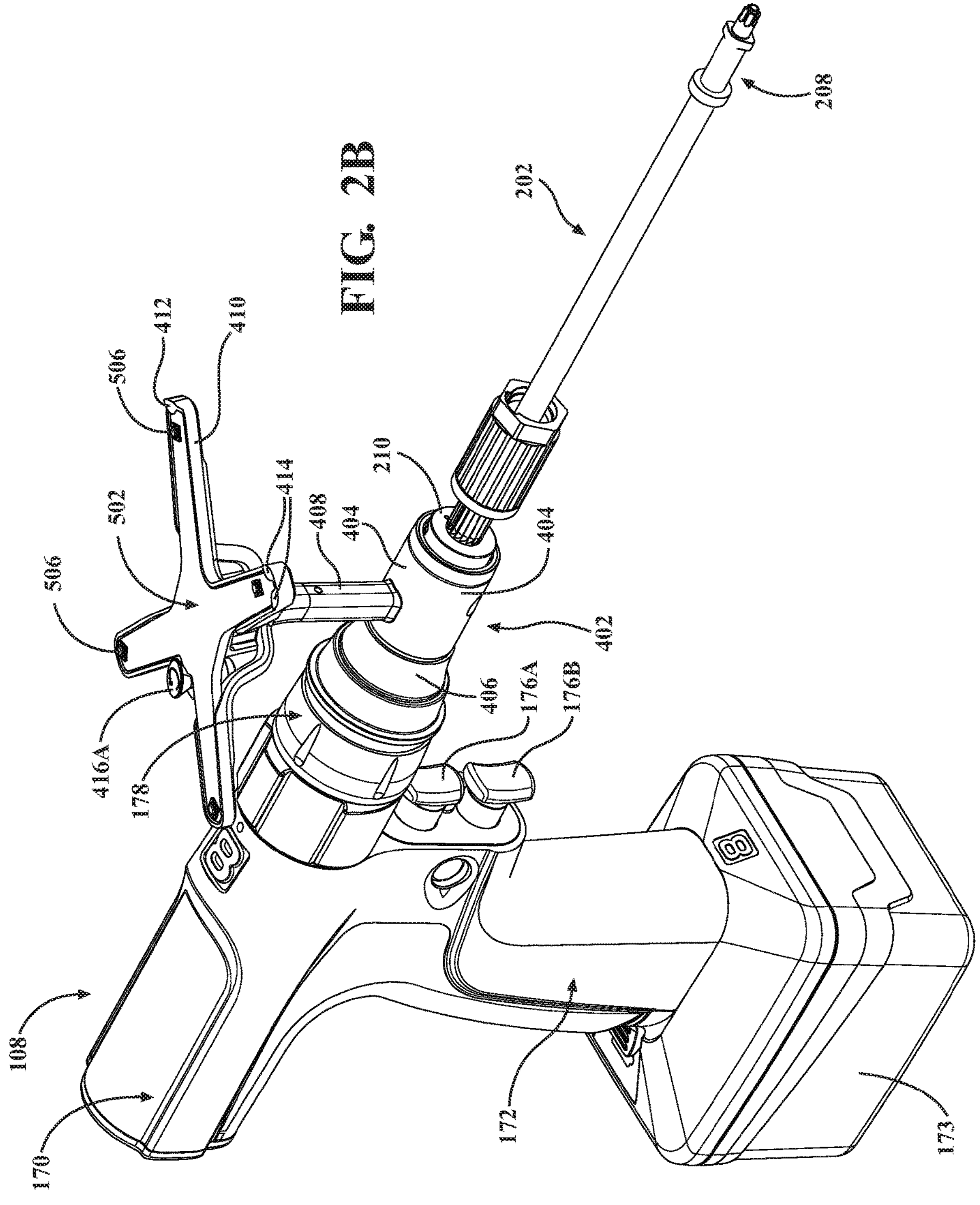
FIG. 2B is an alternative perspective view of the surgical instrument of FIG. 2A, the surgical instrument including the surgical handpiece, end effector, and rotational adapter supporting the tracker.
Figure 3:
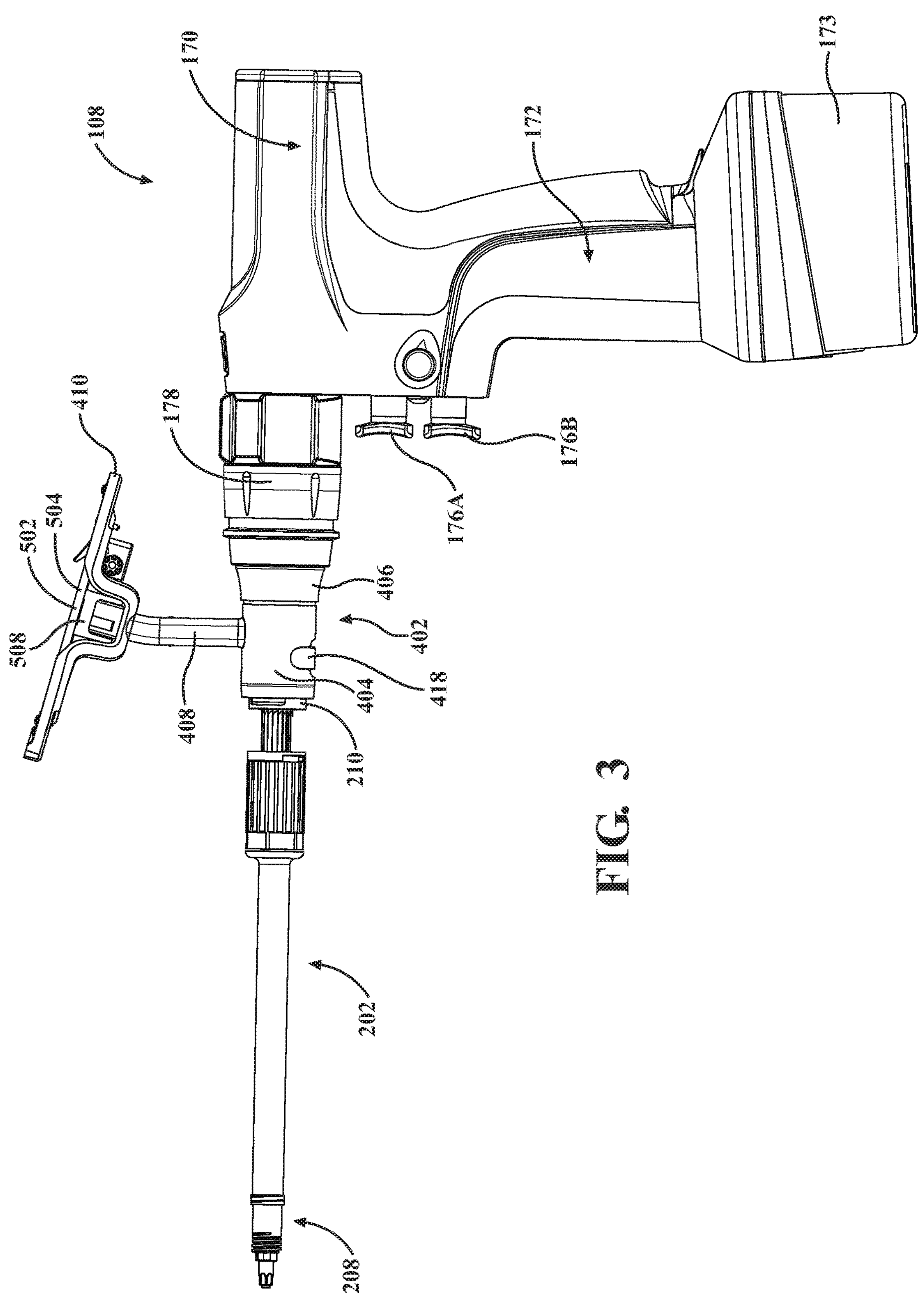
FIG. 3 is a side view of the surgical instrument including the surgical handpiece, end effector, and rotational adapter supporting the tracker of FIGS. 2A and 2B.

In FIG. 1A, the tool tracker 502 and the imaging system tracker 132B are each depicted generically and are mounted to the surgical instruments 106A, 106B and the gantry 122 of the imaging system 104, respectively. The patient trackers 132A may be removably coupled to mount assemblies 134 (e.g., anchors) to define tracker assemblies which facilitate selective movement of the trackers 132A relative to their mount assemblies 134 according to certain implementations of the present disclosure, as described in greater detail below. Here, the patient trackers 132A may be firmly fixed to different portions of the patient's P anatomy (e.g., to opposing lateral sides of the ilium) via the mount assemblies 134 which are configured to releasably engage tissue (e.g., bone), as illustrated in FIG. 1B. It will be appreciated that trackers 132A, 132B, 502 may be firmly affixed to different types of tracked objects (e.g., discrete bones, tools, pointers, and the like) in a number of different ways.

The position of the patient trackers 132A relative to the anatomy of the patient P to which they are attached can be determined by known registration techniques, such as point-based registration in which the tool tracker 502 is attached to a calibration tool 302 (FIG. 11), which will be described in greater detail below. The calibration tool 302, also referred to as a calibration body, is then used to touch off on a known object, such as a calibration block, touch off on bony landmarks of bone, or to touch off on several points across the bone for surface-based registration. Conventional registration techniques can be employed to correlate the pose of the patient trackers 132A to the patient's anatomy. Other types of registration are also possible.

Position and/or orientation data may be gathered, determined, or otherwise handled by the navigation controller 128 using conventional registration/navigation techniques to determine coordinates of each tracker 132A, 132B, 502 within the localizer coordinate system LCLZ. These coordinates may be utilized by various components of the surgical system 100 (e.g., to facilitate control of the surgical instruments 106, to facilitate navigation based on the imaging data, and the like).

In the representative embodiment illustrated in FIG. 1A, the navigation controller 128 and the localizer 130 are supported on a mobile cart 140 which is movable relative to the base 120 of the imaging system 104. The mobile cart 140 also supports a user interface, generally indicated at 142, to facilitate operation of the navigation system 102 by displaying information to, and/or by receiving information from, the surgeon or another user. The user interface 142 may be disposed in communication with other components of the surgical system 100 (e.g., with the imaging system 104), and may comprise one or more output devices 144 (e.g., monitors, indicators, display screens, and the like) to present information to the surgeon (e.g., images, video, data, a graphics, navigable menus, and the like), and one or more input devices 146 (e.g., buttons, touch screens, keyboards, mice, gesture or voice-based input devices, and the like). It will be appreciated that other types, arrangements, and configurations are contemplated. By way of non-limiting example, in some embodiments, certain components of the navigation system 102 may be arranged in other ways, such as with the localizer 130 mounted or otherwise coupled to the imaging system 104.

In some implementations, the surgical system 100 is capable of displaying a virtual representation of the relative positions and orientations of tracked objects to the surgeon or other users of the surgical system 100, such as with images and/or graphical representations of the anatomy of the patient P and the surgical instruments 106 presented on one or more output devices 144 (e.g., a display screen). The navigation controller 128 may also utilize the user interface 142 to display instructions or request information from the surgeon or other users of the surgical system 100. Other configurations are contemplated. One type of mobile cart 140 and user interface 142 of this type of navigation system 102 is described in U.S. Pat. No. 7,725,162, entitled "Surgery System," the disclosure of which is hereby incorporated by reference in its entirety.

Because the mobile cart 140 and the gantry 122 of the imaging system 104 can be positioned relative to each other and also relative to the patient P in the representative configuration illustrated in FIG. 1A, the navigation system 102 can transform the coordinates of each tracker 132A, 132B, 502 from the localizer coordinate system LCLZ into other coordinate systems (e.g., defined by different trackers 132A, 132B, 502, localizers 130, and the like), or vice versa, so that navigation relative to the target site ST (or control of surgical instruments 106A, 106B) can be based at least partially on the relative positions and orientations of multiple trackers 132A, 132B, 502 within a common coordinate system (e.g., the localizer coordinate system LCLZ). Coordinates can be transformed using a number of different conventional coordinate system transformation techniques. It will be appreciated that the localizer 130 or other components of the navigation system 102 could be arranged, supported, or otherwise configured in other ways without departing from the scope of the present disclosure. By way of non-limiting example, the localizer 130 could be coupled to the imaging system 104 in some configurations (e.g., to the gantry 122). Other configurations are contemplated.

In the illustrated configuration, the localizer 130 is an optical localizer and includes a camera unit 148 with one or more optical sensors 150. The navigation system 102 employs the optical sensors 150 of the camera unit 148 to sense the position and/or orientation of the trackers 132A, 132B, 502 within the localizer coordinate system LCLZ. To this end, the trackers 132A, 132B, 502 each employ one or more markers 152, 506 (also referred to as "fiducials" in some configurations) that are supported on a body 154, 504 on the tracker 132A, 132B, 502 in a predetermined arrangement. However, as will be appreciated from the subsequent description below, trackers 132A, 132B, 502 may have different configurations, such as with different quantities of markers 152, 506 that can be secured to or otherwise formed in other structures besides the bodies 154, 504 illustrated throughout the drawings (e.g., various types of housings, frames, surfaces, and the like). Other configurations are contemplated.

The illustrated configuration includes trackers 132A, 132B, 502 utilizing light sources (e.g., light emitting diodes "LEDs"), which emit light that is sensed by the optical sensors 150 of the camera unit 148.

Alternatively, the trackers 132, 502 could each employ "passive" markers 152, 506 (e.g., reflective markers such as spheres, cones, and the like) which reflect emitted light that is sensed by the optical sensors 150 of the camera unit 148. Examples of navigation systems 102 of these types are described in U.S. Pat. No. 9,008,757, entitled "Navigation System Including Optical and Non-Optical Sensors," the disclosure of which is hereby incorporated by reference in its entirety.

Although one implementation of the mobile cart 140 and localizer 130 of the navigation system 102 is illustrated in FIG. 1, it will be appreciated that the navigation system 102 may have any other suitable configuration for monitoring trackers 132A, 132B, 502 which, as will be appreciated from the subsequent description below, may be of various types and configurations and could employ various types of markers 152, 506. Thus, for the purposes of clarity and consistency, the term "marker 152, 506" is used herein to refer to a portion of a tracker 132A, 132B, 502 (e.g., a passive marker 152, 506 mounted to a body 154, 504) that can be monitored by a localizer 130 to track (e.g., states, motion, position, orientation, and the like) the object to which the tracker 132A, 132B, 502 is secured, irrespective of the specific type or configuration of the localizer 130 and/or tracker 132A, 132B, 502.

The navigation system 102 and/or localizer 130 may have any other suitable components or structure not specifically recited herein. Furthermore, any of the techniques, methods, and/or components described above with respect to the camera-based navigation system 102 shown throughout the drawings may be implemented or provided for any of the other configurations of the navigation system 102 described herein. For example, the navigation system 102 may also be based on one or more of inertial tracking, ultrasonic tracking, image-based optical tracking (e.g., with markers 152, 506 defined by patterns, shapes, edges, and the like that can be monitored with a camera), or any combination of tracking techniques. Other configurations are contemplated.

Referring now to FIG. 1B, as noted above, the patient trackers 132A are supported on respective mount assemblies 134, which in turn are secured to different portions of the patient's P anatomy (e.g., on opposing lateral sides of the ilium). In the representative illustrations of the patient trackers 132A illustrated throughout the drawings, each of the patient trackers 132A comprises a respective body 154 to which four markers 152 are secured. As noted above, the markers 152 in the illustrative configurations are realized as LEDs. However, those having ordinary skill in the art will appreciate that other configurations are contemplated, and the patient trackers 132A could be of various styles, types, and/or configurations, and could employ any suitable quantity, type, and/or arrangement of markers 152 without departing from the scope of the present disclosure.

Referring to FIGS. 2A-4, an exemplary configuration of a surgical instrument 106, such as a powered surgical handpiece 108, is illustrated. In the representative configuration illustrated herein, the surgical handpiece 108 generally comprises a housing 170 including a grip portion 172. The surgical handpiece 108 further comprises a motor 174 disposed within the housing 170, and one or more triggers 176A, 176B configured to selectively actuating the motor 174. The surgical handpiece 108 may be powered by a battery 173 that is removably coupled to the handpiece, or may employ a cord for connecting the surgical handpiece 108 to a control box or electrical outlet (not shown) to supply power to the motor 174. When activated, the motor 174 is configured to actuate an end effector 202, 302.

Figure 4:
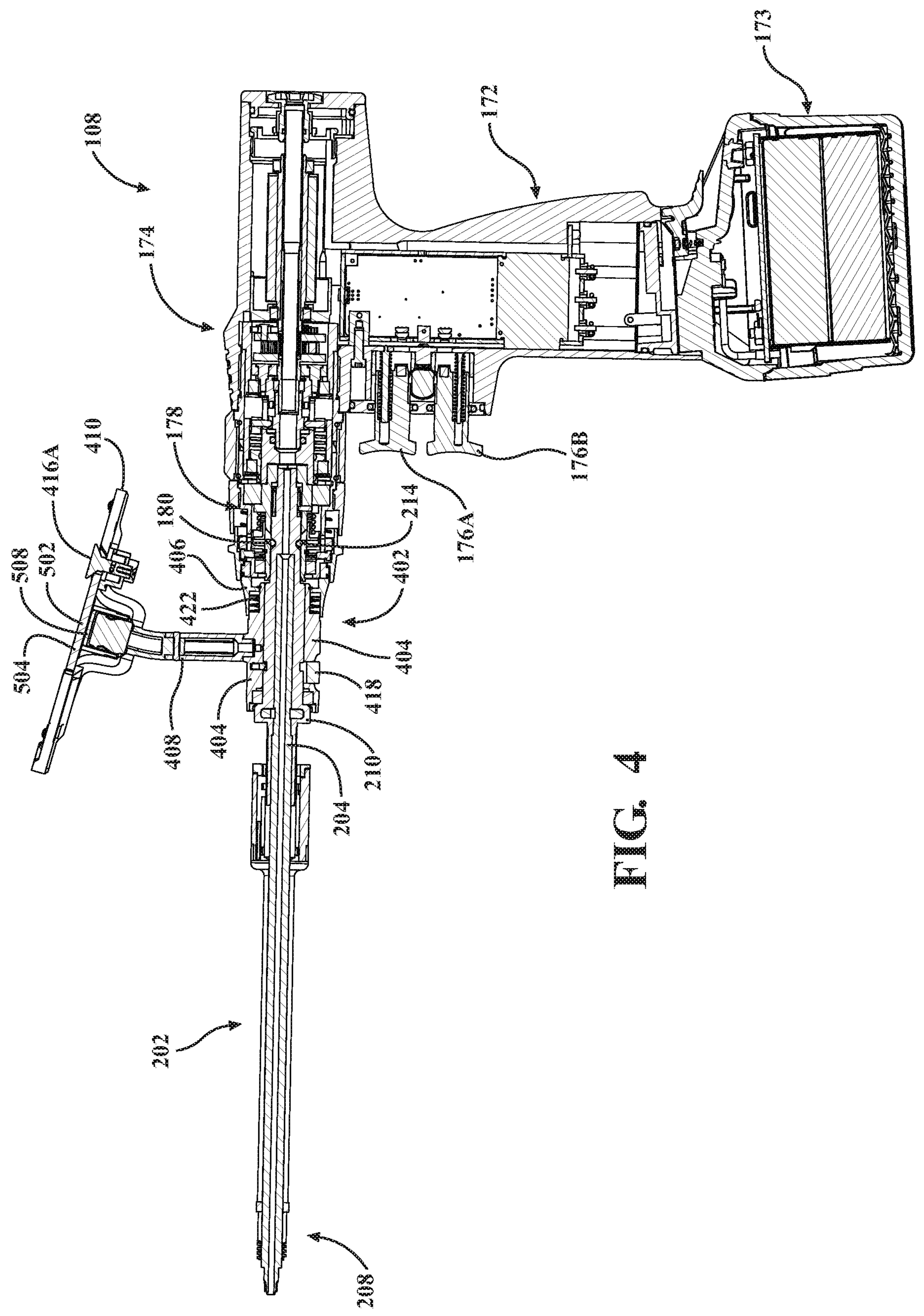
FIG. 4 is a side sectional view of the surgical instrument including the surgical handpiece, end effector, and rotational adapter supporting the tracker of FIGS. 2A-3.

The surgical handpiece 108 may further comprise a receiver 178 configured to receive an end effector 202, 302. As illustrated in FIGS. 2A-4, the end effector 202, 302 may be realized as a screwdriver for inserting an implant in the patient. However, it is also contemplated that the end effector 202, 302 may comprise a drill bit, a tap, a reamer, an awl, or any similar surgical instrument working member that is commonly coupled to a surgical handpiece 108. The receiver 178 may comprise a coupling mechanism to removably couple the end effector 202, 302 to the surgical handpiece 108. The coupling mechanism may comprise a clamp, traditionally referred to as a chuck or drill chuck, configured to provide symmetrical pressure about an exterior surface of the end effector 202, 302 that that is coupled to the surgical handpiece 108. For example, the surgical handpiece 108, such as a surgical drill, may comprise a chuck for removably coupling an end effector 202, 302, such as a drill bit, reamer, or driver, to the surgical handpiece 108. Alternatively, as illustrated in FIG. 4, the receiver 178 may comprise a quick-release or quick-connect chuck including opening keyed to the shape of the end effector 202, 302 and a retention feature 180 adapted to matingly engage a retainer 214, 314 of the end effector to couple the end effector to the surgical handpiece 108.

In some configurations, the powered surgical handpiece 108 may include a first trigger 176A and a second trigger 176B. The motor 174 may be configured to actuate the receiver 178 in a first direction, such as rotating clockwise, when the first trigger 176A is manipulated by the user; and to actuate the receiver 178 in a second direction, such as rotating counterclockwise, when the second trigger 176B is manipulated by the user. However, it will be appreciated that other configurations are contemplated, and the powered surgical handpiece 108 may be of various styles, types, and configurations without departing from the scope of the present disclosure.

As noted above, during a surgical procedure, an instrument tracker 502 including a marker 506 (also referred to herein as a tracking element) may be coupled to the surgical instrument 106 to allow the navigation system 102 to determine the position and/or orientation of the surgical instrument 106. The instrument tracker may be a disposable tracker including markers 506 and a battery 508. An exemplary implementation of a disposable tracker is shown and described in International Application No. PCT/IB2020/059064, which is hereby incorporated by reference.

Figure 5A:
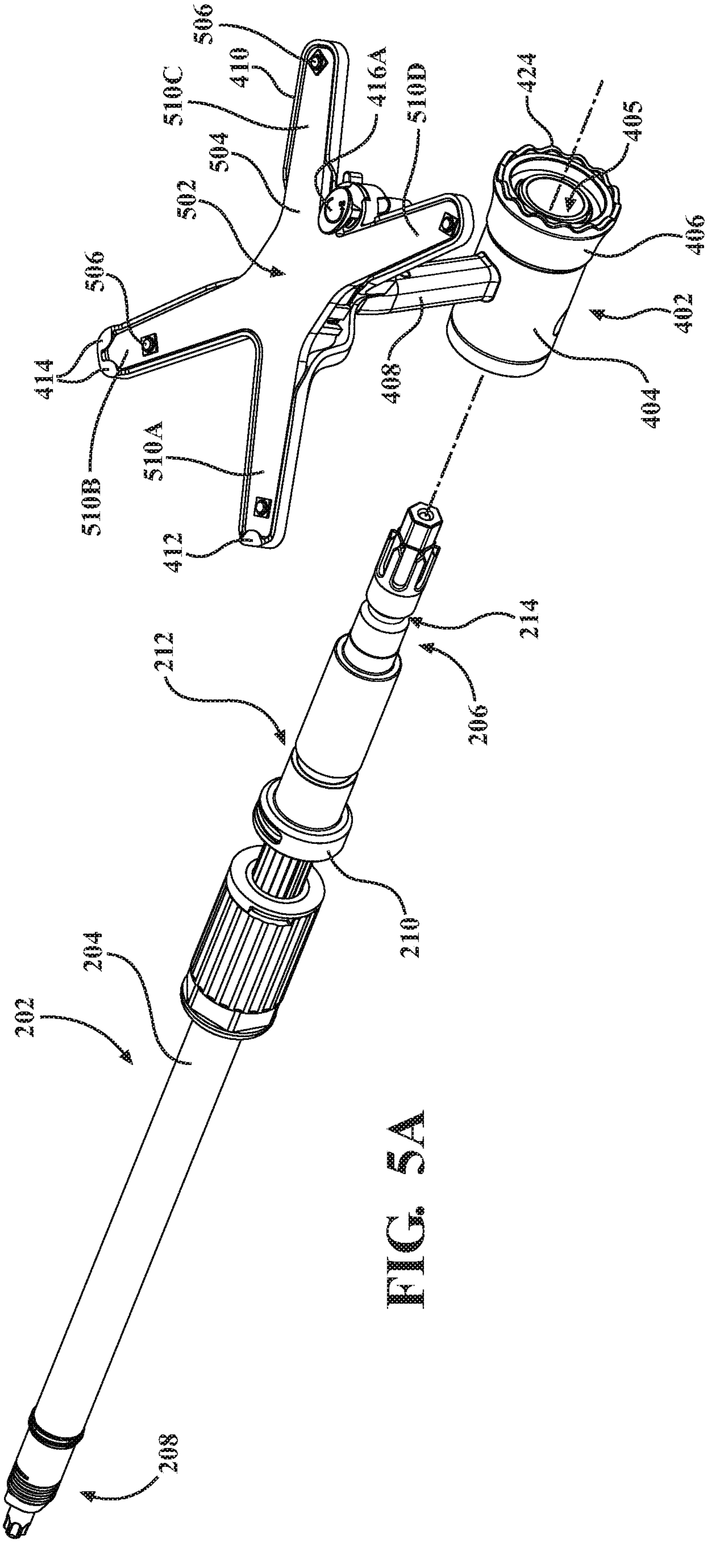
FIG. 5A is a partially exploded view of a rotational adapter including a tracker with a first configuration of an end effector for use with a surgical instrument of FIGS. 2A-4.
Figure 5B:
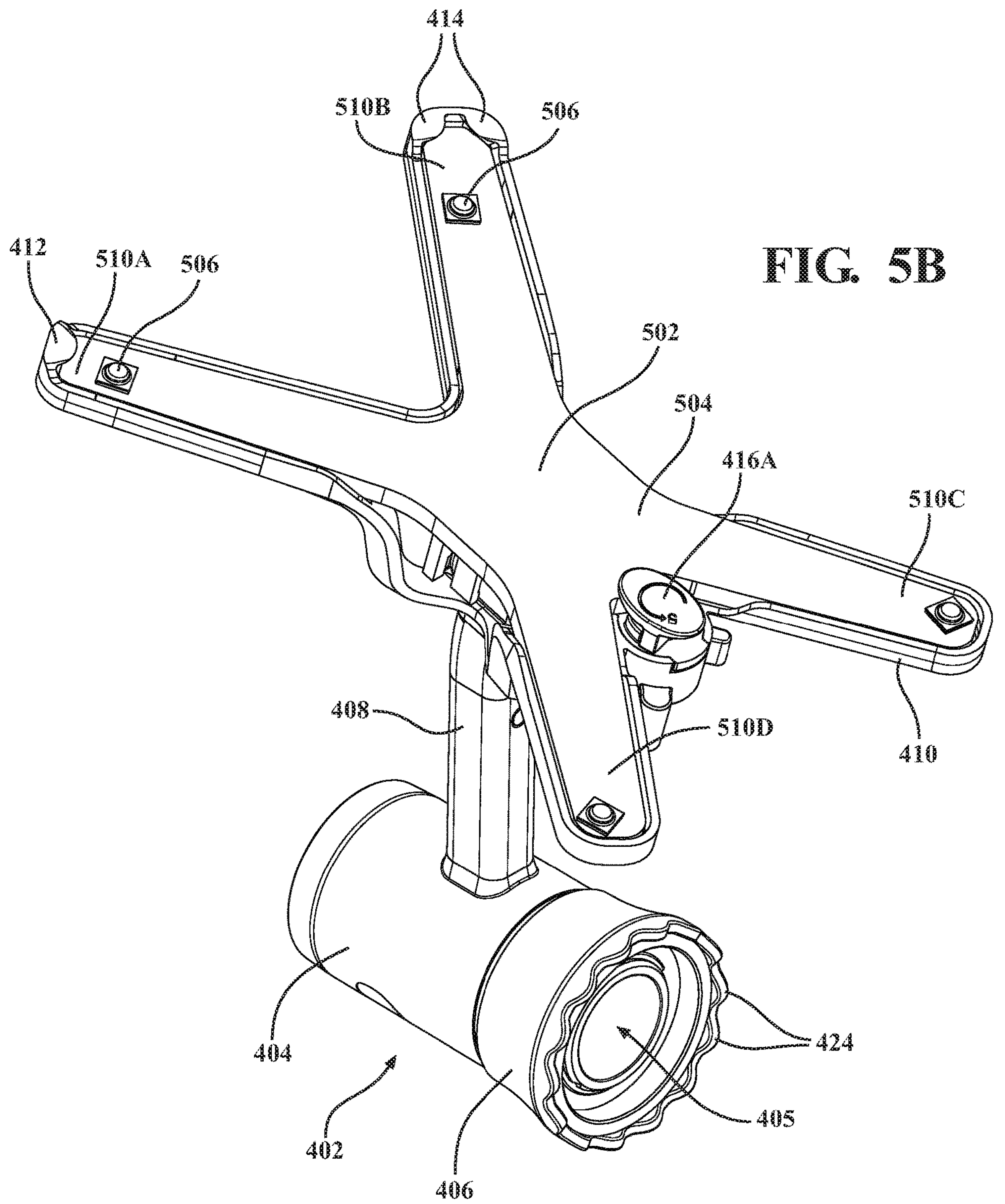
FIG. 5B is a perspective view of the rotational adapter of FIGS. 2A-4, including a tracker for navigating a surgical instrument that may be coupled to the rotational adapter.
Figure 5C:
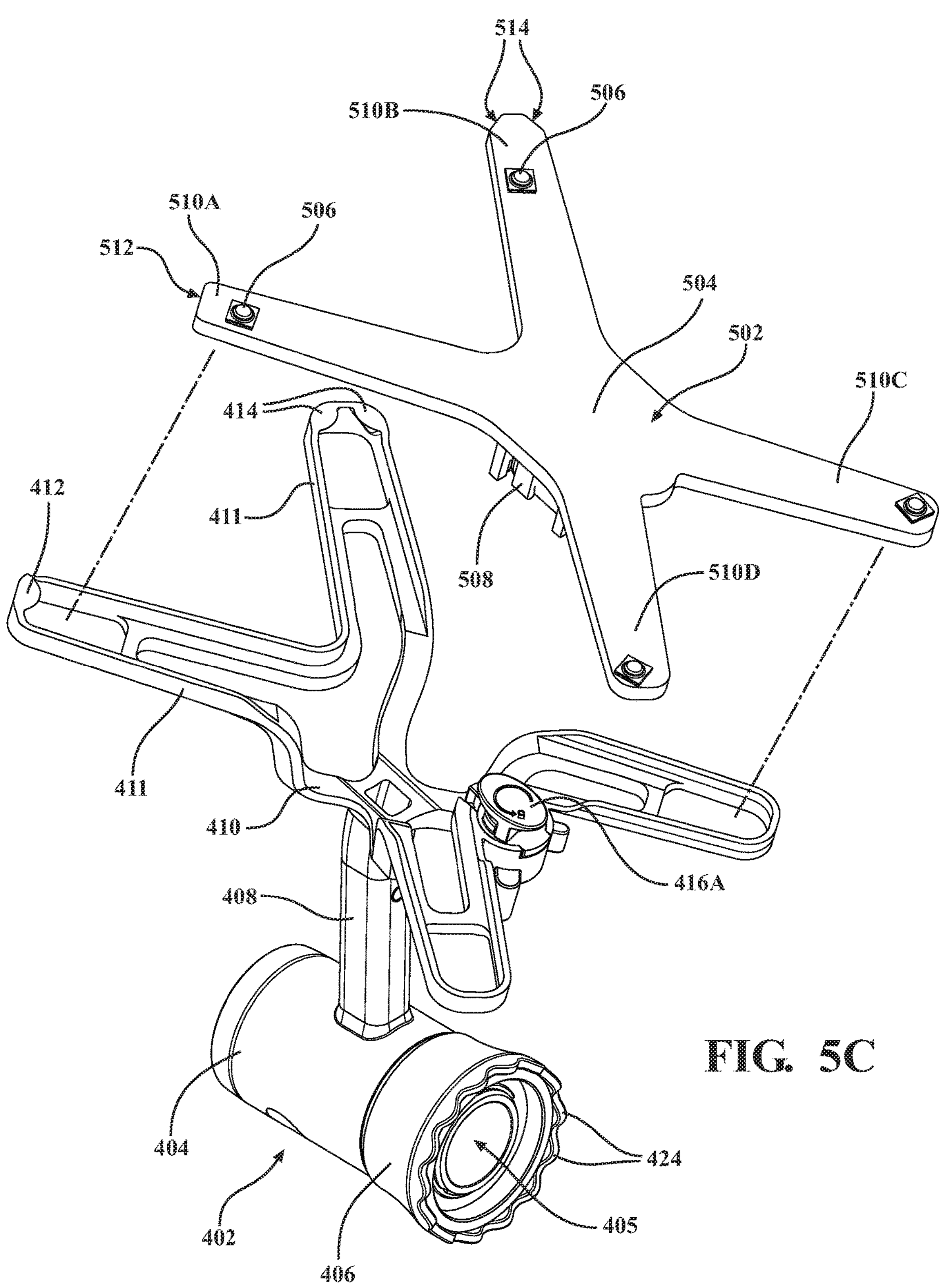
FIG. 5C is an exploded view of the rotational adapter and tracker of FIG. 5B, showing the tracker removed from the tracker mount of the rotational adapter.

Referring to FIG. 5A-5C, an exemplary configuration of an adapter 402 for coupling an instrument tracker 502 to one or more types of surgical instruments 106 is illustrated. The adapter 402 generally includes a distal member 404 and a proximal member 406.

The combination of the distal member 404 and the proximal member 406 may define an aperture 405 that extends through the adapter 402 and is configured to receive a portion of the end effector 202, 302. For example, as will be described in more detail below, the surgical instrument 106 comprises an end effector 202, 302 including a shaft 204, 304 extending between a distal portion 208, 308 for manipulating tissue and proximal portion 206, 306 defining a retainer 214, 314 for removably attaching the end effector 202, 302 to the surgical handpiece 108. The end effector 202, 302 also includes a reference feature 210, 310 arranged between the proximal portion 206, 306 and the distal portion 208, 308 of the shaft 204, 304. The reference feature 210, 310 may also be referred to as a stop, as the distal surface of the distal member 404 of the adapter 402 is configured to abut reference feature 210, 310. The aperture 405 in the adapter 402 is defined to receive the proximal portion 206, 306 of the shaft 204, 304 of the end effector 202, 302. The adapter 402 may also include a tracker mount 408 coupled to and extending from the distal member 404 for releasably securing the tracker 502 to the adapter 402.

The tracker mount 408 comprises a base 410 configured to receive a tracker 502. An exemplary configuration of a tracker 502 for use with the adapter 402 is illustrated in FIGS. 5A-5C. The tracker 502 may comprise a body 504 (may also be referred to as base 504). The body 504 may include a plurality of leg portions 510A, 510B, 510C, 510D. While the tracker 502 is illustrated in the figures as having a generally X-shaped body 504, it is contemplated that the body 504 may be formed in any number of suitable shapes, such as a square, rectangle, disk, triangle, plate, circle, sphere, trapezoid cube, or the like.

The leg portions 510A, 510B may be shaped to assist with coupling the tracker to the base 410 of the tracker mount 408. For example, a first leg 510A may comprise a distal end 512 that is generally flat and configured to engage a first coupling feature 412 of the base 410 to couple the tracker to the base 410, which will be described in greater detail below. A second leg 510B may comprise a distal end 514 shaped to include a fillet or chamfer configured to engage a second coupling feature 414 of the base 410 to couple the tracker to the base 410, which will be described in greater detail below.

As described above, the tracker 502 may comprise one or more markers 506, which may also be referred to as fiducials. The markers 506 may be configured as light sources or reflective type markers 506, consistent with the description above. The markers 506 may be coupled to the body 504 of the tracker 502 in a unique pattern or arrangement that is identifiable to the navigation system 102. For example, as illustrated in 5B and 5C, a marker 506 is disposed on each of the leg portions 510A, 510B, 510C, 510D of the tracker 502. In the instance of tracker 502 including a light source, such as an LED marker 506, the tracker 502 may also include a battery 508 that is coupled to the body 504 of the tracker 502. For example, as illustrated in FIG. 5C, the battery 508 may be coupled to the underside or bottom surface the body 504 of the tracker 502 and electrically connected to each of the markers 506. Some exemplary implementations of LED tracking markers are shown and described in U.S. Patent Application Publ. No. 2019/0321108 and International Application No. PCT/IB2020/060187, both of which are hereby incorporated by reference.

Figure 15:
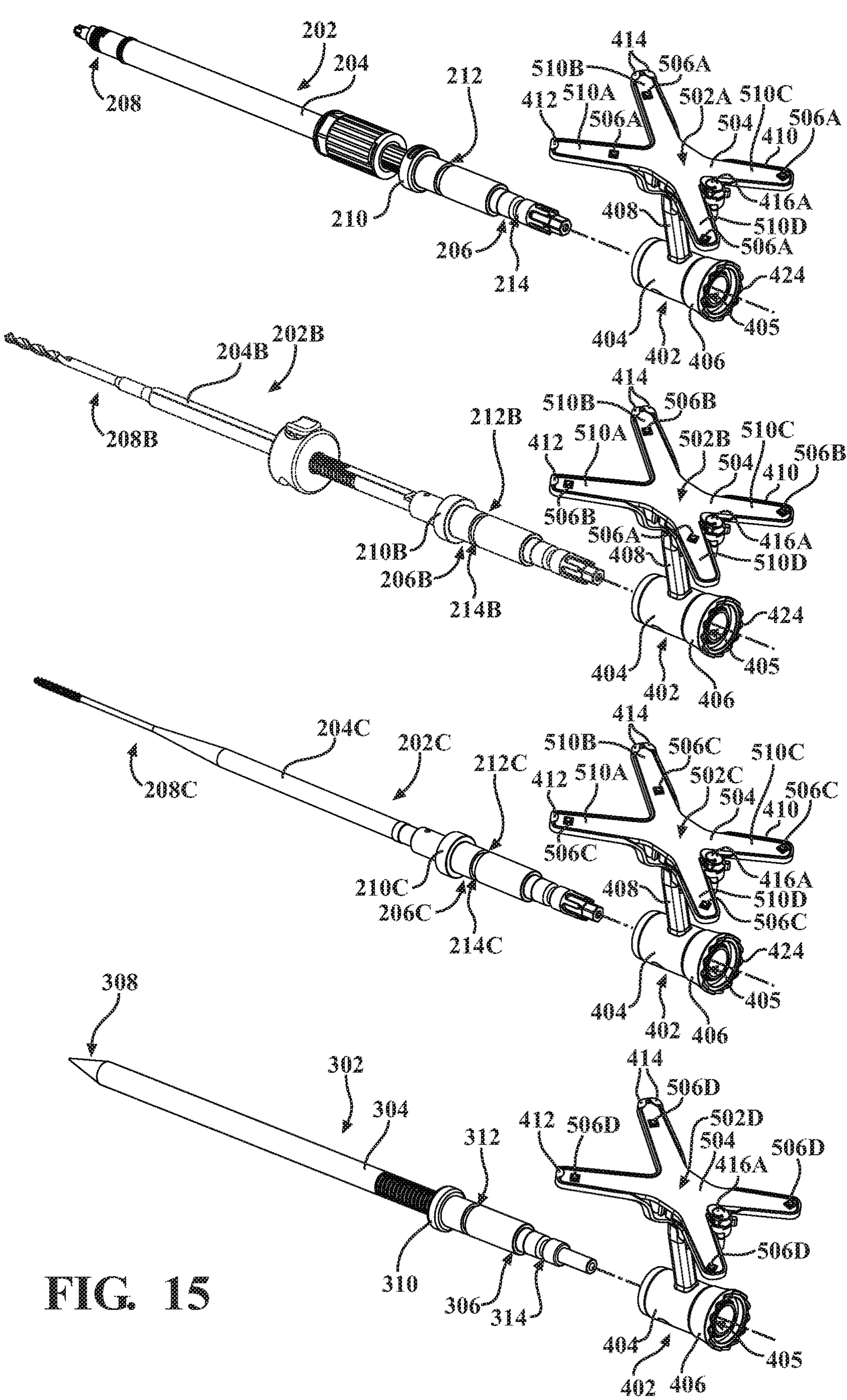
FIG. 15 is a perspective view of a surgical kit including a plurality of different end effectors, each of the end effectors including a rotational adapter and a unique tracker that is associated with the end effector and identifiable by the navigation system.

Referring to FIG. 15, a plurality of end effectors 202, 202B, 202C, 302 are shown each having their own adapter 402 and tracker 502. Each of the trackers 502 may have a unique pattern of markers 506A, 506B, 506C, 506D that is identifiable by the navigation system 102. The navigation system 102 may thus be configured to assign a given pattern of markers 506A, 506B, 506C, 506D on a tracker 502 to a particular end effector 202, 202B, 202C, 302 either by user selection/input into the navigation system 102 or by using the optical sensor 150 of the camera unit 148, i.e. machine vision, to identify the end effector 202, 202B, 202C, 302 that the pattern of markers 506A, 506B, 506C, 506D is associated with. Once a particular pattern of markers 506A, 506B, 506C, 506D is assigned to one of the end effectors 202, 202B, 202C, 302, the navigation system 102 will be able to identify which of the end effectors 202, 202B, 202C, 302 is currently in use, and accurately track the pose of the given end effector 202, 202B, 202C, 302 as it is manipulated by the user.

As illustrated in FIG. 5C, the base 410 of the tracker mount 408 may comprise a wall 411 extending from a perimeter of the base 410 and defining a recess shaped to receive the tracker 502. The wall(s) 411 surrounding the perimeter of the base 410 may be configured to extend above the top surface of the tracker 502 when the tracker 502 is disposed in the recess and coupled to the tracker mount 408. This may assist in protecting the tracker 502 from being damaged. For example, if the tracker mount 408 were set down or dropped while the tracker 502 was mounted to the tracker mount 408, the wall(s) 411 extending above the top surface of the tracker 502 could prevent tracker 502 from experiencing any type of direct impact with the table, floor, etc. It is further contemplated that the wall(s) 411 may extend sufficiently above the top surface of the tracker and the highest point of the marker(s) 506 to prevent the markers 506 from experiencing any type of direct impact with the table, floor, etc. if the tracker mount 408 were set down or dropped while the tracker 502 was mounted to the tracker mount 408. However, the wall(s) 411, when considered in combination with the position of the markers 506 on the body of the tracker 502, should not extend so far above the top surface of the tracker 502 that the view of the markers 506 by the optical sensors 150 of the camera unit of the navigation system is significantly inhibited and/or obstructed.

Figures 8A, 8B, 8C:
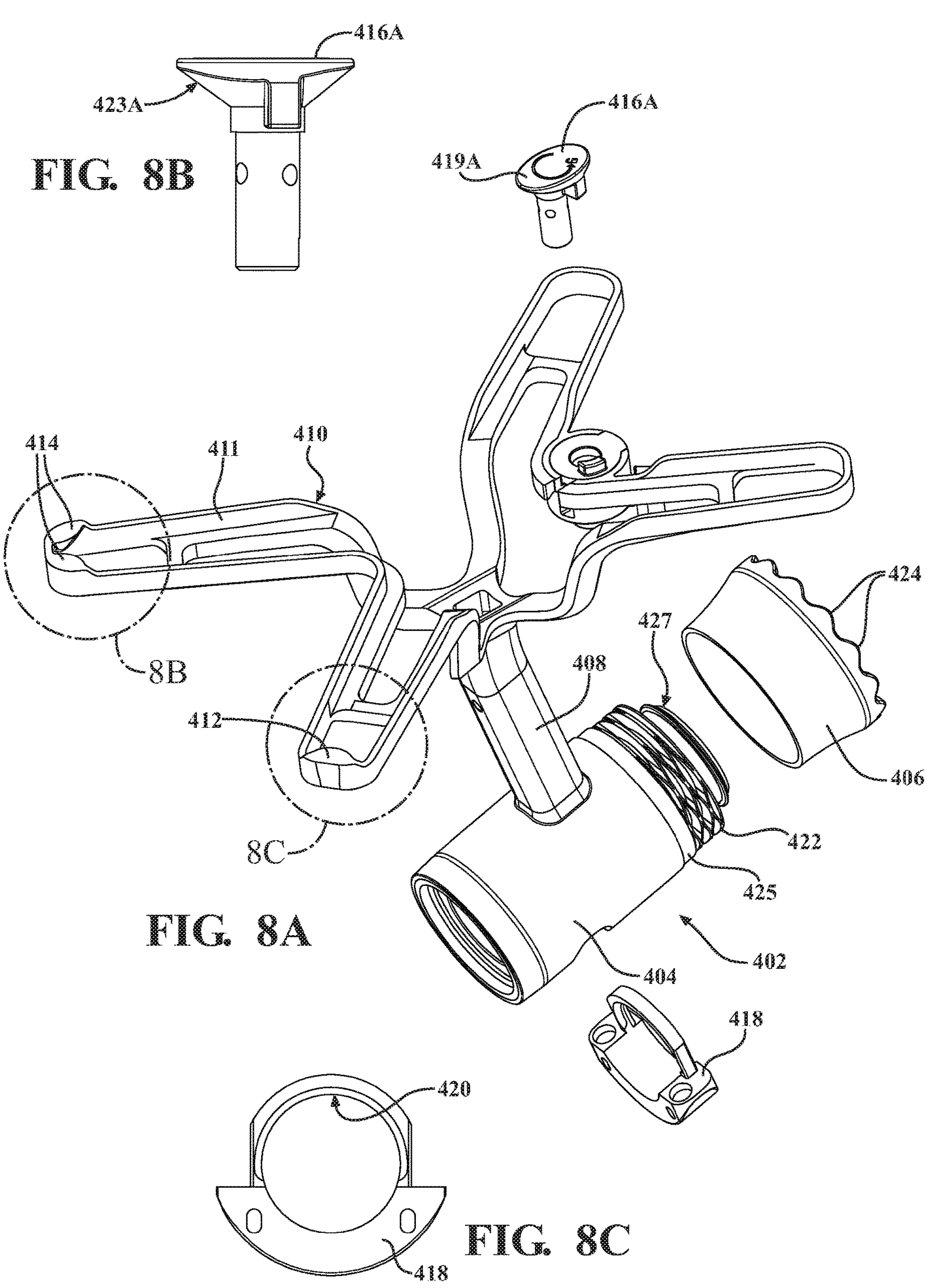
FIG. 8A is a perspective view of the rotational adapter of FIGS. 5A-7C shown without the tracker to illustrate the features of a tracker mount of the rotational adapter.
FIG. 8B is a side view of an exemplary configuration of a locking mechanism of the tracker mount of the rotational adapter of FIG. 8A.
FIG. 8C is a front view of an exemplary configuration of a coupler of the rotational adapter of FIG. 8A.
Figures 8D, 8E, 9A:
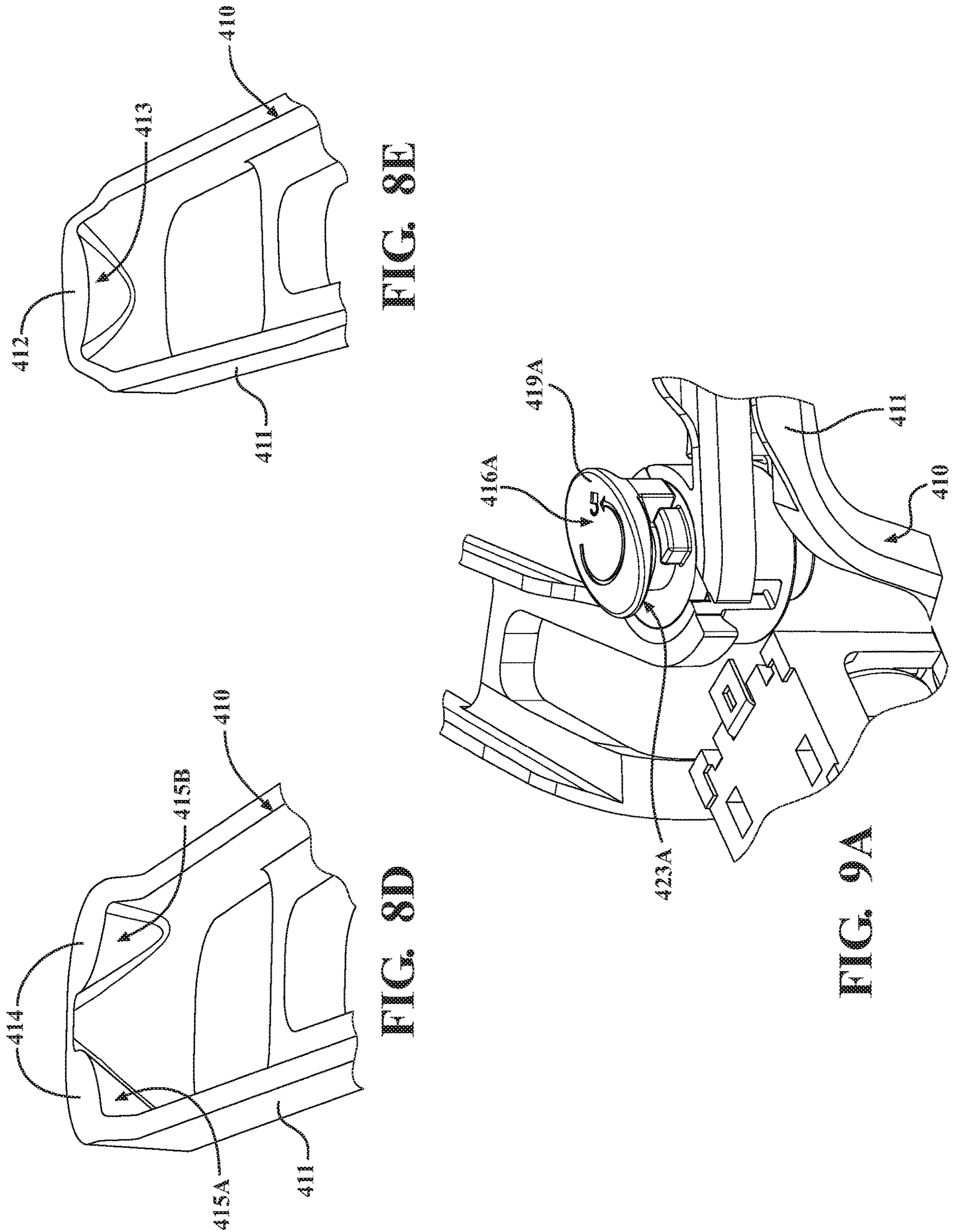
FIG. 8D is an enhanced perspective view illustrating a first alignment feature of the tracker mount for aligning the tracker within the tracker mount.
FIG. 8E is an enhanced perspective view illustrating a second alignment feature of the tracker mount for aligning the tracker within the tracker mount.
FIG. 9A is a perspective view of a first configuration of a locking mechanism of the rotational adapter of FIGS. 5A-7C for releasably securing the tracker to the tracking mount.

The base 410 may also comprise one or more coupling features 412, 414 configured to removably secure and/or align the tracker 502 with the base 410. As illustrated in FIGS. 8A-8C, the base 410 may be shaped to define the coupling features 412, 414. For example, the coupling feature 412, 414 may be configured as a tab extending from the wall(s) 411 defined at the perimeter of the base 410. The body 504 of the tracker 502 may be shaped to fit within the recess defined by the walls 411 of the base, and the tab 412, 414 may further be configured such that a portion of the body 504 of the tracker 502 is disposed between the tab 412, 414 and the base 410 when the tracker 502 is attached to the base 410 of the tracker mount 408. As illustrated in FIGS. 8A and 8C, the base 410 may be shaped to define a first coupling feature 412. The first coupling feature 412 may comprise a tab that is positioned over the base 410 such that the first leg 510A of the body 504 of the tracker 502 is positioned between the tab and the base 410. Furthermore, as illustrated in FIG. 8E, the first coupling feature 412 may comprise an angled surface 413. The angled surface 413 of the first coupling feature 412 may serve to wedge the first leg 510A of the tracker body 504 between the first coupling feature 412 and the base 410. The angled surface 413 of the first coupling feature 412 may engage the distal end 512 of the first leg 510A to prevent lateral movement of the tracker 502 relative to the base 410 when coupled to the tracker mount 408. For example, if a coordinate system were arranged such that the plane defined by the X-axis and Y-axis were oriented in parallel to a top surface of the body 504 of the tracker 502 and the Z-axis was oriented to be perpendicular to the top surface of the body 504, the first coupling feature 412 may be configured to prevent movement of the body 504 of the tracker 502 along the Z-axis when the first leg 510A of the body 504 of the tracker 502 is positioned between the first coupling feature 412 and the base 410.

As illustrated in FIGS. 8A and 8B, the base 410 may also be shaped to define a second coupling feature 414. The second coupling feature 414 may comprise a pair of spaced apart tabs that are positioned over the base 410 such that the second leg 510B of the body 504 of the tracker 502 is positioned between the second coupling feature 414 and the base 410. Furthermore, as illustrated in FIG. 8D, the second coupling feature 414 may comprise angled surfaces 415A, 415B. The angled surfaces 415A, 415B of the second coupling feature 414 may serve to wedge the distal end 514 of the second leg 510A of the body 504 between the second coupling feature 414 and the base 410. The pair of angled surfaces 415A, 415B of the second coupling feature 414 being spaced apart may be configured to engage the fillet or chamfer of the distal end 514 of the second leg 510B to provide an anti-rotational force on the body 504 of the tracker 502 to prevent the body 504 of the tracker 502 from rotating relative to the base 410. For example, using the coordinate system described above where the plane defined by the X-axis and Y-axis is parallel to the top surface of the body 504 of the tracker 502 and the Z-axis is perpendicular to the top surface of the body 504, the second coupling feature 414 may be configured to prevent movement of the tracker in yaw. The combination of the first coupling feature 412 and the second coupling feature 414 applies both a retention force and an anti-rotational force to the body 504 of the tracker 502 limiting the movement of the tracker 502 in all six degrees of freedom, which can improve both the fitment and the accuracy of the positioning of the tracker 502 relative to the adapter 402. For example, the first coupling feature 412 may provide a retention force, preventing the vertical movement of the tracker 502 relative to the Z-axis, and the second coupling feature 414 may provide an anti-rotational force, preventing the tracker 502 from yawing about the Z-axis and/or rolling about the Y-axis.

While the figures illustrate the tracker mount 408 as including one first coupling feature 412 including a single angle surface 413 and one second coupling feature 414 including a pair of spaced apart angled surface 415A, 415B, it is contemplated that the tracker mount 408 may be configured with an additional first coupling feature 412 with a single angled surface 413 that replaces the second coupling feature 414 illustrated in the figures. Alternatively, it is further contemplated that the tracker mount 408 may be configured with an additional second coupling feature 414 with a pair of angled surfaces 415A, 415B that replaces the single coupling feature 412 illustrated in the figures. The tracker mount 408 may comprises any number and/or combination of coupling features 412, 414 arranged on the base 410 of the tracker mount 408 for removably securing the tracker 502 to the tracker mount 408.

Referring to FIGS. 9A to 10B, the tracker mount 408 may further comprise a locking mechanism 416A, 416B. As illustrated in FIGS. 9A-9C, the tracker mount 408 may comprise a first locking mechanism 416A. The locking mechanism 416A comprises a rotatable member 419A configured as a cam lock that may be rotated between a locked (see FIG. 9B) and an unlocked position (see FIG. 9C). The rotatable member 419A be formed in an oblong or eccentric cam-like shape, such that as rotatable member 419A of the lock mechanism 416A is rotated from the unlocked position to the locked position, an engagement surface 423A of the oblong portion of the rotatable member 419A is rotated to engage the body 504 of the tracker 502. When the rotatable member 419A is in the locked position, the engagement surface 423A may be configured to urge the tracker 502 laterally toward the coupling features 412, 414, while also applying a downward force on the body 504 of the tracker to secure the tracker 502 to the base 410. For example, as illustrated in FIG. 9C, the rotatable member 419A of the locking mechanism 416A may be positioned in an unlocked position such that the oblong portion of the rotatable member 419A is not disposed over and/or is disengaged from the body 504 of the tracker 502. When rotatable member 419A of the locking mechanism 416A is in the unlocked position, this allows the tracker 502 to be inserted into or removed from the base 410 of the tracker mount 408. For example, as described above, when in the unlocked position, the legs 510A, 510B of the tracker 502 may be slid under the coupling features 412, 414 of the base 410 and/or withdrawn from under the coupling features 412, 414 of the base 410, allowing the tracker 502 to be separated from the tracker mount 408.

Figure 9B:
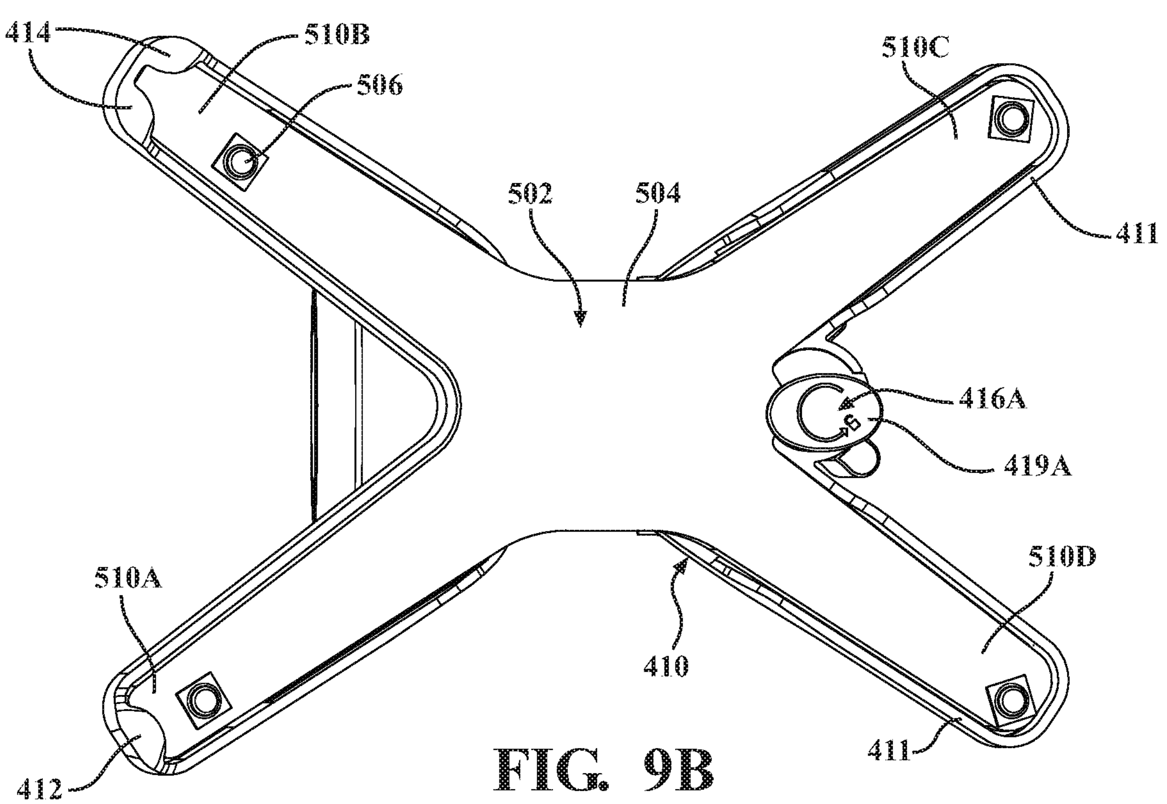
FIG. 9B is a top view of the rotational adapter including the tracker coupled to the tracker mount by the first configuration of the locking mechanism, the locking mechanism illustrated in a locked position to secure the tracker to the tracker mount and the rotational adapter.
Figure 9C:
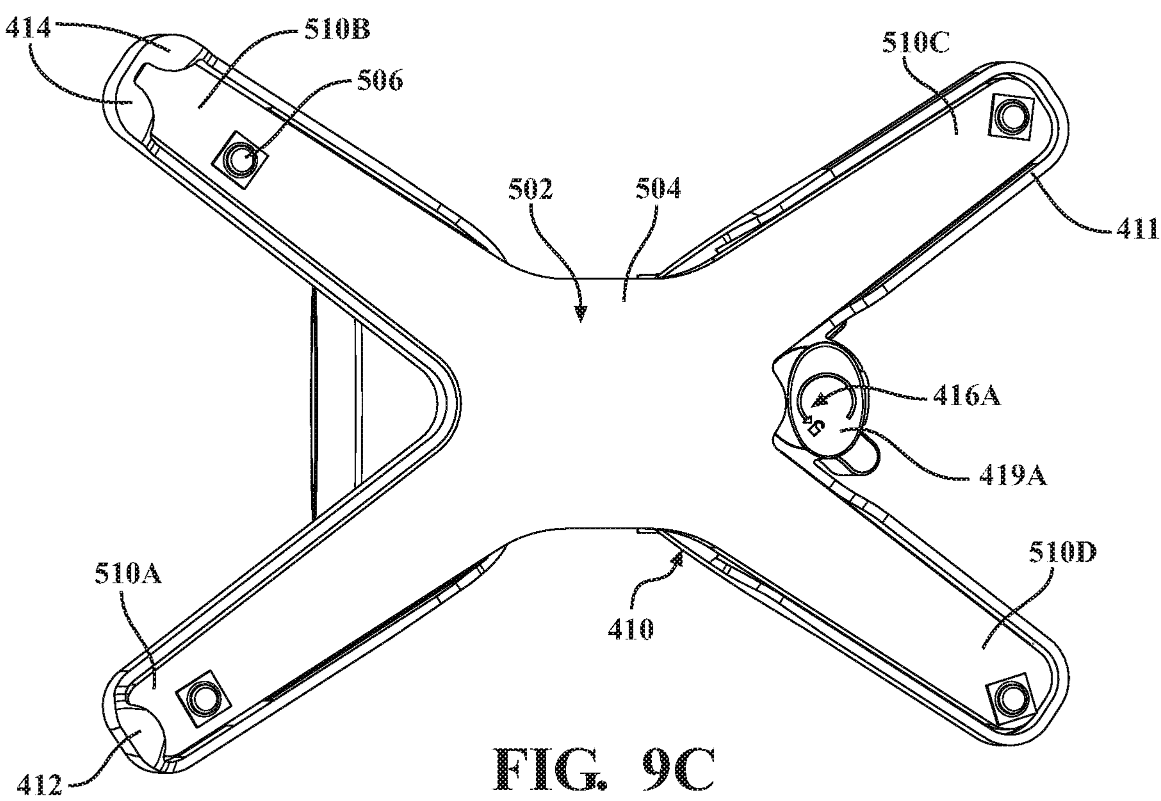
FIG. 9C is a top view of the rotational adapter including the first configuration of the locking mechanism in an unlocked position allowing the tracker to be decoupled from the tracker mount and the rotational adapter.

As illustrated in FIGS. 9A and 9B, the rotatable member 419A of the locking mechanism 416A may be rotated from the unlocked position to the locked position, such that the oblong portion of the rotatable member 419A is disposed over and/or is engaged with the body 504 of the tracker 502. When the locking mechanism 416A is in the locked position, the engagement surface 423A of the oblong portion of the rotatable member 419A engages the body 504 of the tracker 502, urging the body 504 laterally toward the coupling features 412, 414 of the base 410 of the tracker mount 408. The lock mechanism 416A may further be configured such that the engagement surface 423A of the oblong portion of the locking mechanism 416A is engaged with the body 504 of the tracker 502 when the locking mechanism 416A is in the lock position to supply a downward force on the body 504 to secure the tracker 502 to the tracker mount 408.

Figures 10A, 10B:
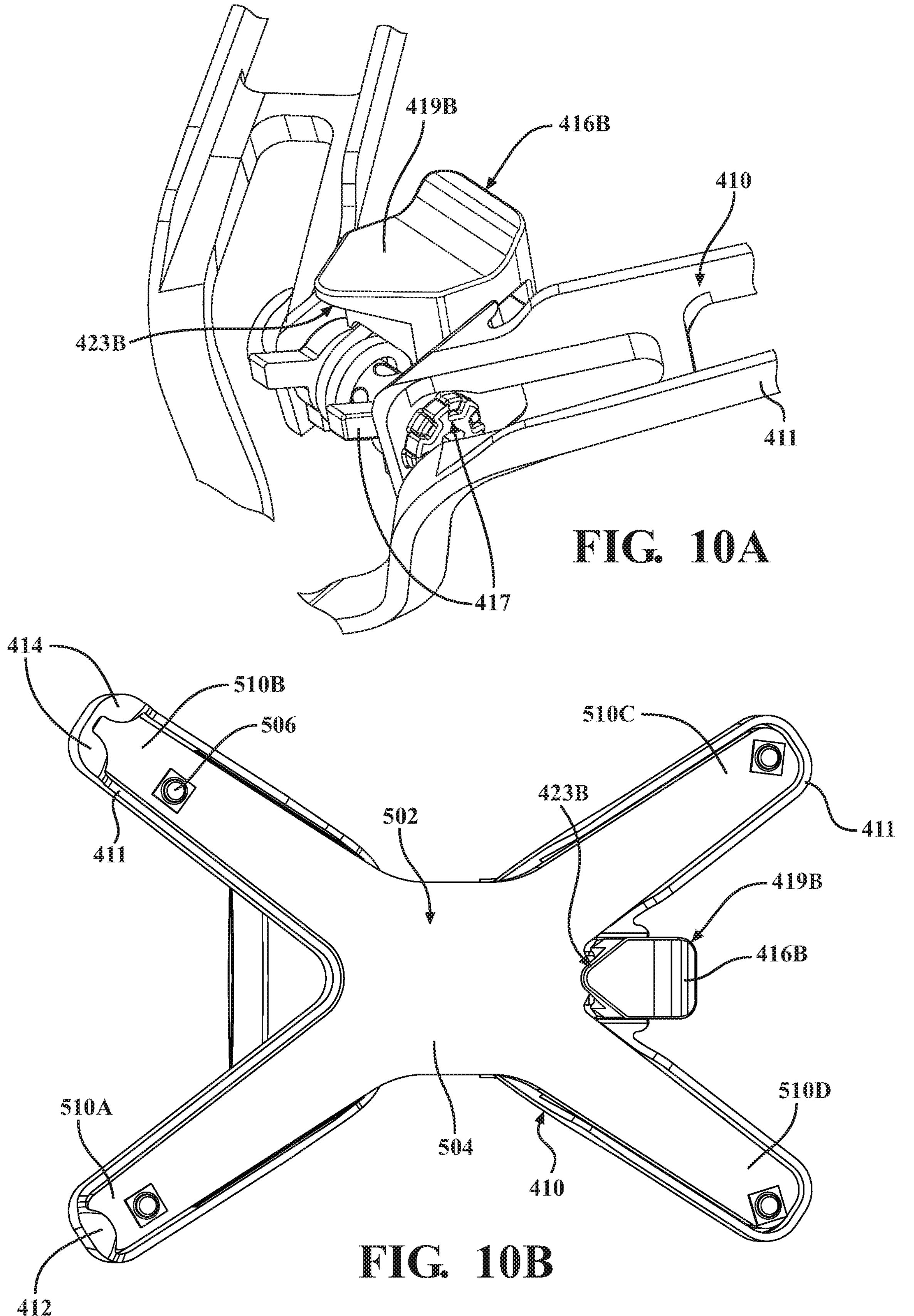
FIG. 10A is a is a perspective view of a second configuration of a locking mechanism of the rotational adapter of FIGS. 5A-7C for releasably securing the tracker to the tracking mount.
FIG. 10B is a top view of the rotational adapter including the tracker coupled to the tracker mount by the second configuration of the locking mechanism, the locking mechanism illustrated in a locked position to secure the tracker to the tracker mount and the rotational adapter.

As illustrated in FIGS. 10A and 10B, the tracker mount may alternatively comprise a second locking mechanism 416B. The locking mechanism 416B is configured as a pivot locking mechanism. For example, the locking mechanism 416B may include a pivotable member 419B and a biasing device 417. The pivotable member 419B may comprise a lever, tab, or similar protrusion defining an engagement surface 423B that is pivotable between a locked and unlocked position. The biasing device 417 may be configured to bias the pivotable member 419B into the locked position. The pivotable member 419B may be moved to the unlocked position by applying sufficient force to the pivotable member 419B to overcome the force of the biasing device 417. For example, the user may apply a force to the pivotable member 419B to pivot the pivotable member 419B from its natural locked position to an unlocked position. As described above, the tracker 502 may be inserted and/or removed from the base 410 of the tracker mount 408 when the pivotable member 419B of the locking mechanism 416B is in the unlocked position. Once the tracker 502 is inserted into the base 410, the pivotable member 419B of the locking mechanism 416B may be released allowing the biasing device 417 to return the pivotable member 419B to its natural locked position. The pivotable member 419B of the locking mechanism 416B may be shaped such that the engagement surface 423B of the pivotable member 419B engages the body 504 of the tracker 502 and urges the body 504 toward the coupling features 412, 414 of the base 410 of the tracker mount 408 when in the locked position. The pivotable member 419B of the locking mechanism 416B may further be shaped such that an engagement surface 423B of the pivotable member 419B is disposed over the body 504 of the tracker 502 when in the locked position to supply a downward force on the body 504 to secure the tracker 502 to the tracker mount 408.

A rotatable member 419A and/or a pivotable member 419B style locking mechanism 416A, 416B may be utilized to accurately and securely mount the tracker 502 to the tracker mount 408 in a quick and efficient manner without the need for additional tools such as a wrench or screw driver. Furthermore, the rotatable member 419A and/or pivotable member 419B of the locking mechanism 416A, 416B are coupled to the tracker mount 408 and do not require removal from the tracker mount 408 to insert and/or mount the tracker 502. Use of a screw or bolt that must be removed from the tracker mount 408 introduces the possibility of losing the screw or bolt, as well as additional sterilization considerations as the tracker mount 408 and tracker 502 may generally be used in a sterile environment.

Furthermore, coupling or mounting members such as a screw or bolt introduce torquing requirements that could result in damage and/or improper securement of the tracker 502 to the tracker mount 408. For example, if the user over tightens the screw or bolt, it is possible that the tracker 502 may be damaged. The body 504 of the tracker 502 may be constructed from a plastic type material that is generally flexible. The material of the body 504 may also be brittle. Furthermore, the body 504 of the tracker 502 may house circuitry and/or other sensitive/brittle components needed of operation of the marker(s) 506. These components may be damaged if a bolt or screw is over tightened. Alternatively, if the user under tightens the screw or bolt, the tracker 502 may not be securely coupled to the tracker mount 408 and may move or shift within the tracker mount 408 during use. This could result in incorrect data related to the pose of the end effector 202, 302 being presented to the user by the navigation system 102. Moreover, as described above, the body 504 of the tracker 502 may house circuitry and/or other sensitive/brittle components needed of operation of the marker(s) 506 that can complicate placing an aperture or hole in the body 504 of the tracker 502 for the purpose of mounting the tracker 502 to the tracker mount 408.

While the tracker mount 408 is described as being associated with and/or part of the rotational adapter 402 for mounting the tracker 502 to the end effector 202, 302 and/or surgical handpiece 108, it is also contemplated that the tracker mount 408 may be utilized to attach a tracker 132A, 132B, 502 to other components. For example, the tracker mount 408 described above may be configured to be coupled to a patient anchor type tracker mount assembly 134, as illustrated in FIG. 1B, and utilized to mount a tracker 132A, 132B, 502, such as a patient tracker 132A, to the patient. The tracker mount 408 may also be configured to mount a tracker 132A, 132B, 502, such as an imaging system tracker 132B, to the imaging system.

Referring to FIGS. 6A-7B, the distal member 404 and the proximal member 406 are coupled to one another such that the distal member 404 is rotationally and/or axially moveable relative to the proximal member 406. For example, the distal member 404 may be rotated relative to the proximal member 406. The distal member 404 may be configured to rotate about an Axis-A, passing through the center of the aperture 405 defined by the distal member 404 and the proximal member 406. The distal member 404 may also be slid laterally along the Axis-A relative to the proximal member 406. To accomplish this, the distal member 404 may be sized to fit within a portion of aperture 405 defined by the proximal member 406. For example, as illustrated in FIGS. 6A-7B, a portion of a proximal end of the distal member 404 is sized to fit within the portion of the aperture 405 that is defined at the distal end of the proximal member 406. This allows the distal member 404 to be rotated within the proximal member 406, while also allowing the distal member 404 to be slid axially within the proximal member 406.

The proximal member 406 may include an abutment interface 424 for engaging the surgical handpiece 108. The abutment interface 424 of the proximal member 406 may define an anti-rotation surface. For example, the abutment interface 424, also referred to as a surgical handpiece interface, may include a plurality of protrusions and/or teeth configured to engage one or more reciprocal features of the surgical handpiece 108 and to resist the rotational movement of the proximal member 406 relative to the surgical handpiece 108.

The adapter 402 may also comprise a biasing member 422 disposed between the distal member 404 and the proximal member 406 of the adapter 402. The biasing member 422 is configured to urge the distal member 404 and the proximal member 406 in opposing directions. The biasing member 422 may comprise a spring, wire coil, or similar mechanism capable of storing potential energy that can be used to provide a biasing force when compressed. For example, as illustrated in FIGS. 6A-7B, the biasing member 422 may comprise a wave spring. It is also contemplated that the biasing member may comprise a spring-like element created from a metallic material that is wire cut to create slits that allow the biasing member 422 to compress when a force is applied and decompress when the force is removed from the biasing member 422.

The adapter 402 may also comprise a coupler 418. The coupler 418 may be disposed on and/or defined in the distal member 404 of the adapter 402 and configured to removably secure the adapter 402 to the end effector 202, 302. The coupler 418 may comprise a sliding mechanism configured to selectively engage a corresponding coupling feature on the end effector 202, 302, such as recess 212, 312, which may be defined as a recess 212, 312 in the proximal portion 206 of the shaft 204.

Figure 6A:
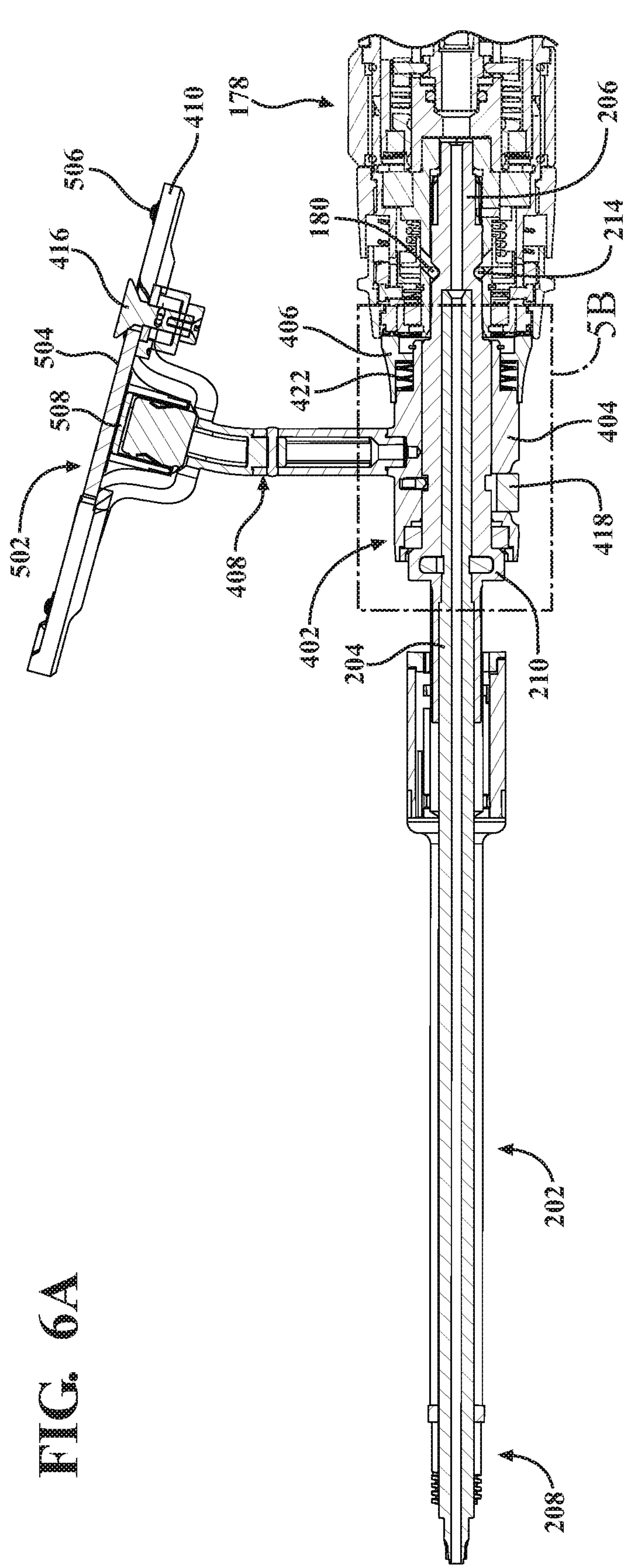
FIG. 6A is a partial sectional view of the rotational adapter for coupling a tracker to the end effector of the surgical instrument illustrated in FIGS. 2A-4, the rotational adapter illustrated in a compressed state when coupled to a surgical instrument.
Figure 6B:
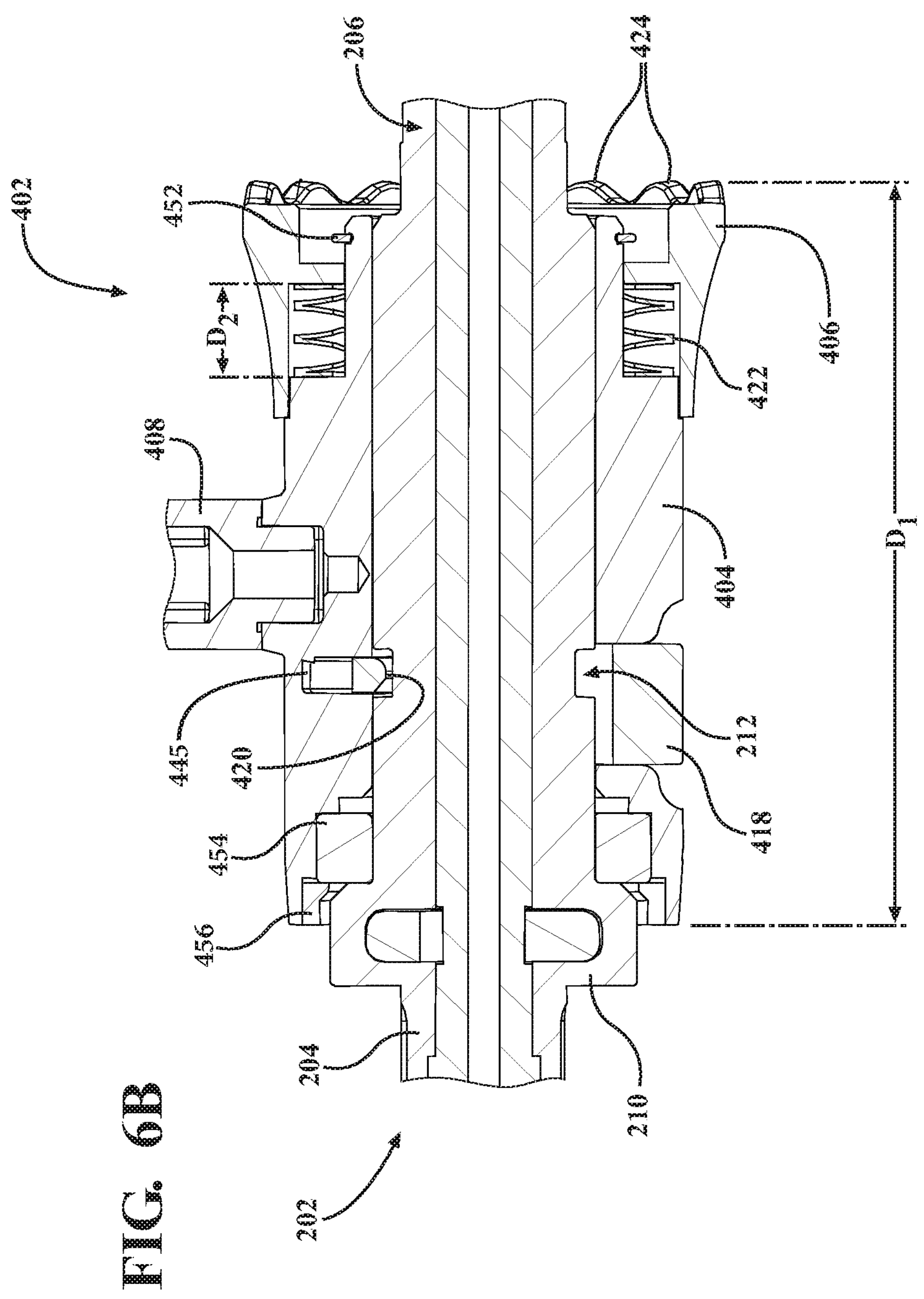
FIG. 6B is an enlarged partial sectional view of the rotational adapter of FIG. 5A, the rotational adapter illustrated in a compressed state when coupled to a surgical instrument.
Figure 7A:
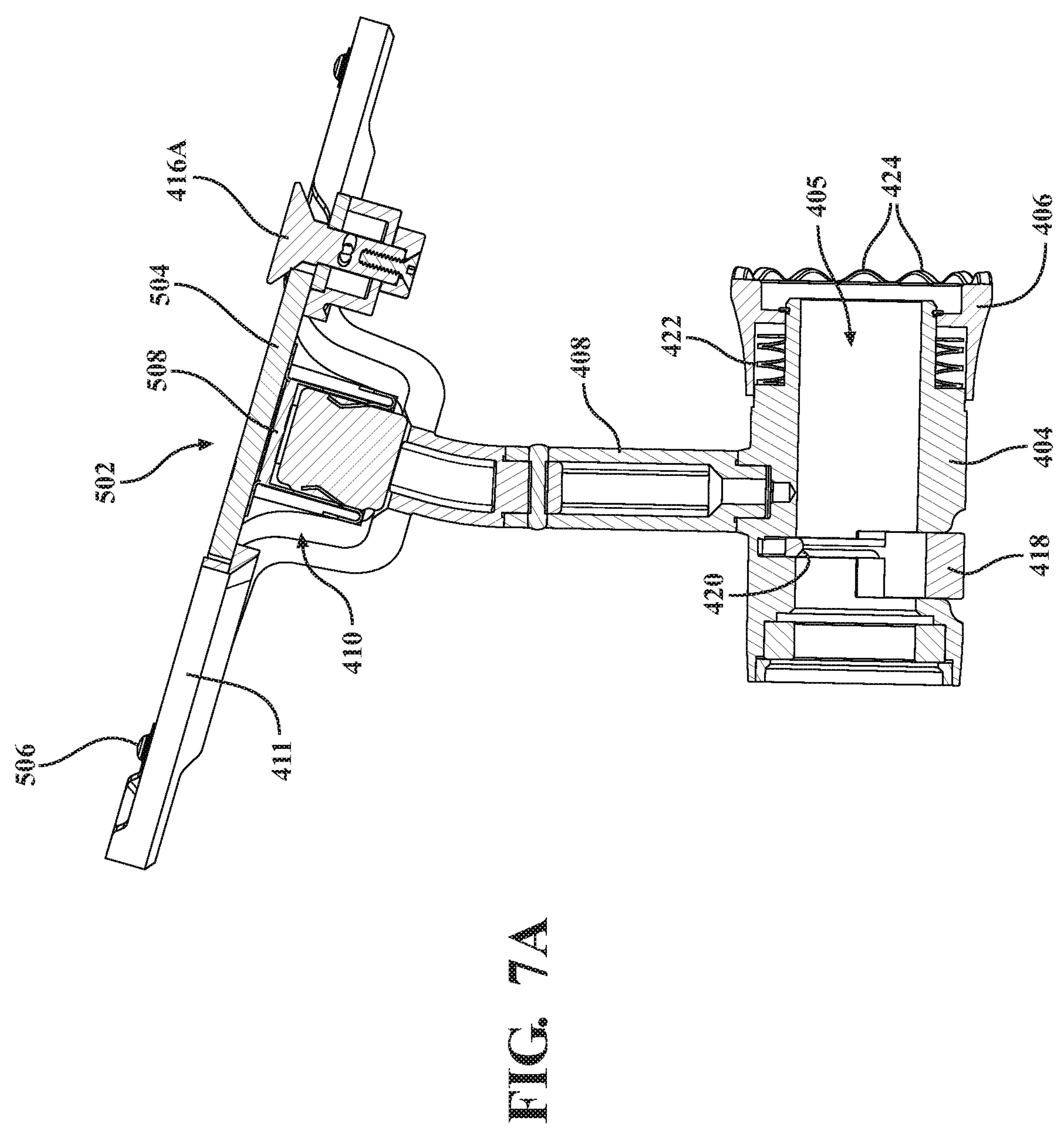
FIG. 7A is a sectional view of the rotational adapter coupled to the first configuration of the end effector in FIG. 6A, the rotational adapter illustrated in a decompressed state when not coupled a surgical handpiece.
Figure 7B:
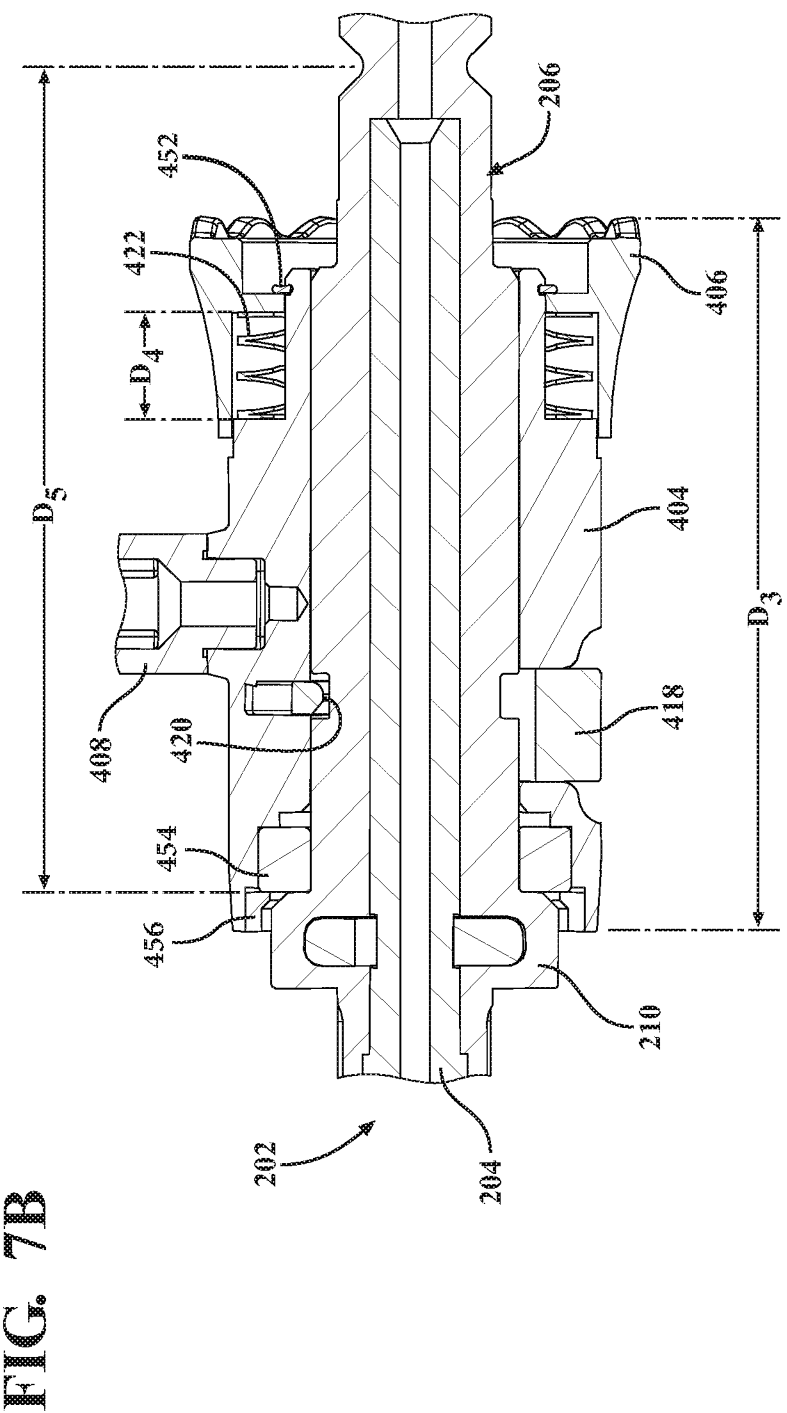
FIG. 7B is a partial sectional view of the rotational adapter for use with the surgical instrument of FIG. 6, the rotational adapter illustrated in a compressed state when coupled to the surgical instrument.

For example, as illustrated in FIGS. 6B and 7B, the coupler 418 may comprise a sliding mechanism including a detent 420 configured to engage an annular recess 212, 312 in the shaft 204, 304 of the end effector 202, 302 when the adapter 402 is coupled to the end effector 202, 302. In operation, the coupler 418, which may also be referred to as a coupling member 418 or fastening member 418, may comprise a detent 420 shaped to allow the user to slide the adapter 402 onto the shaft 204, 304 of the end effector 202, 302. For example, the detent 420 may include a sloped surface that allows the detent 420 to be slid over the shaft 204, 304 of the end effector 202, 302 when attaching the adapter 402 to the end effector 202, 302. Once the adapter 402 has been slid sufficiently far enough onto the shaft 204, 304 of the end effector 202, 302, a pair of springs 442 positioned between the coupling member 418 and the distal member 404 (see FIGS. 25 and 26) may urge the detent 420 to become seated in the recess 212, 312 of the end effector 202, 302 securing the adapter 402 to the end effector 202, 302.

Figure 25:
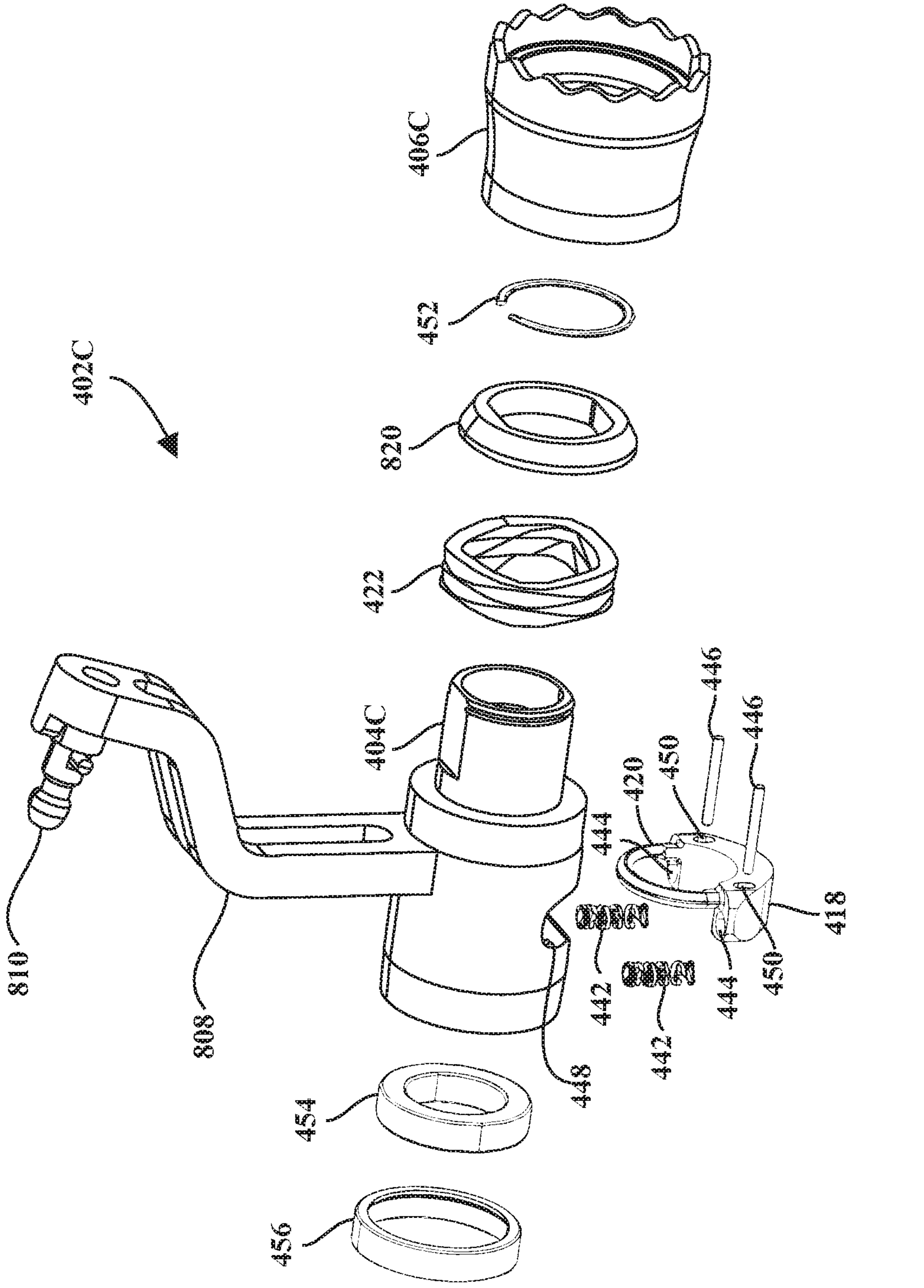
FIG. 25 is an exploded view of the third configuration of the rotational adapter of FIG. 24 illustrating a tapering washer disposed between the biasing member and the proximal member of the rotational adapter.
Figure 26:
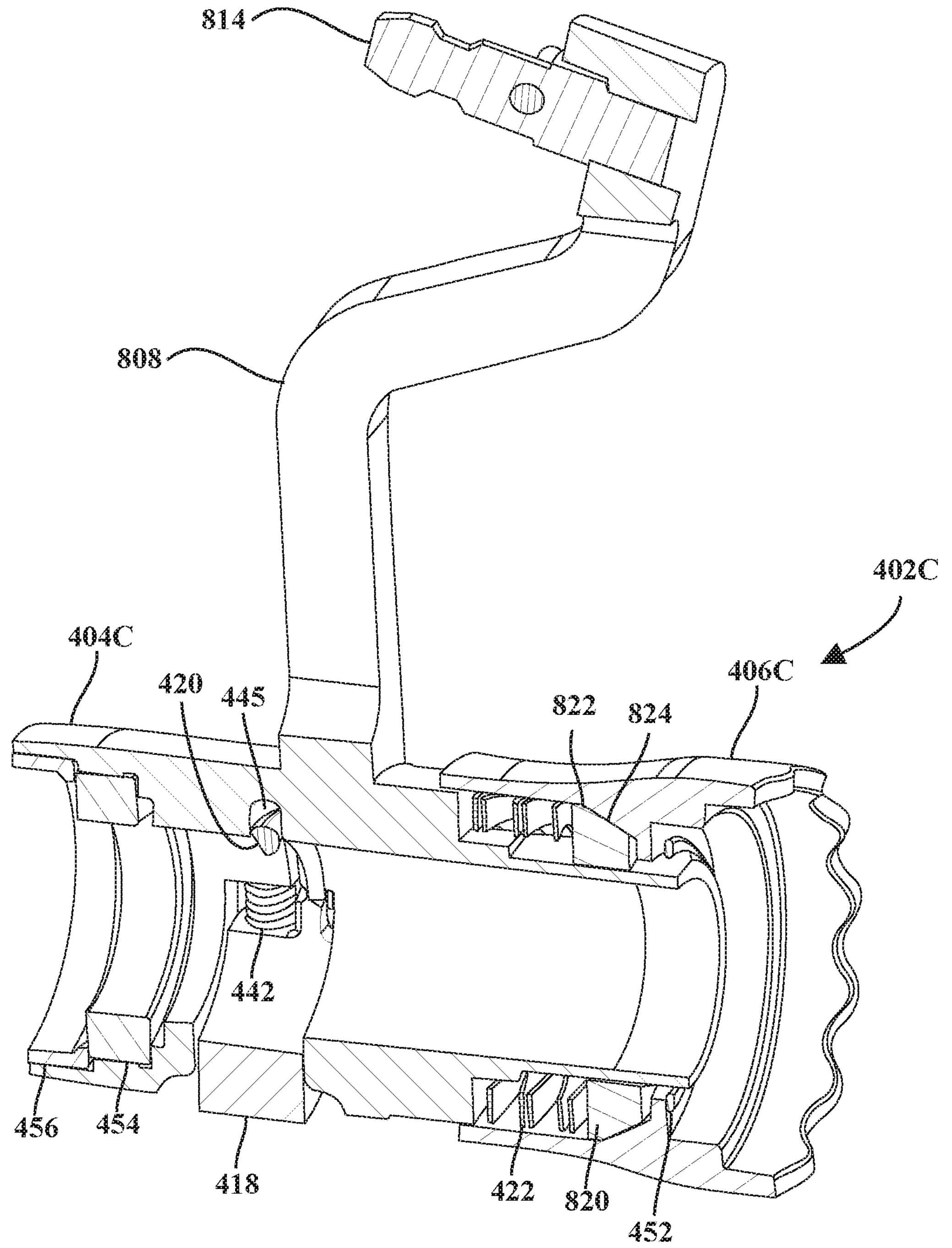
FIG. 26 is a sectional view of the third configuration of the rotational adapter.

More specifically, as illustrated in FIGS. 25 and 26, the coupler 418 may include a pair of opposed bores 444 in which one end of the springs 442 are received, with the other end of the springs 442 abutting a surface of the distal member 404. As the adapter 402 is being slid onto the shaft 204, 304 of the end effector 202, 302, the shaft 204, 304 may function to compress the springs 442 such that the detent 420 is urged into a recess 445 of the of the distal member 404. Once the adapter 402 has been slid sufficiently far enough onto the shaft 204, 304 of the end effector 202, 302 such that the detent 420 is aligned with the recess 212, 312 of the end effector 202, 302, the springs 442 may decompress urging the detent 420 into the recess 212, 312.

In order to detach the adapter 402 from the end effector 202, 302, the user may manipulate the coupler 418 to disengage the detent 420 from the recess 212, 312 of the end effector 202, 302, allowing the user to slide the adapter 402 off the shaft 204, 304 of the end effector 202, 302. More specifically, the user may apply pressure to the coupling member 418, which may compress the springs 442 to urge the detent 420 out of the recess 212, 312 of the end effector 202, 302.

In some implementations, the coupler 418 may be slidably attached to the distal member 404 by a pair of posts 446 extending through the coupler 418 into corresponding bores 448 of the distal member 404. The coupler 418 may include a pair of oblong shaped apertures 450 configured to receive the posts 446. The oblong shape of the apertures 450 may enable the coupler 418 to move relative to the posts 446 as the detent 420 is seated into and unseated from the recess 212, 312 of the end effector 202, 302 as described above.

It will be appreciated that this configuration prevents the adapter 402 from sliding off the end effector 202, 302 when the end effector 202, 302 is separated from the surgical handpiece 108, which promotes significantly improved handling during the process of attaching and detaching the end effector 202, 302 to/from the surgical handpiece 108, as the user does not have to worry about positioning the adapter 402 relative to the surgical handpiece 108 while attaching the end effector to the surgical handpiece 108.

As further illustrated in FIGS. 6B, 25, and 26, the adapter 402 may include additional components such as a snap ring 452, which may be positioned around a proximal portion of the distal member 404, and may be configured to prevent the proximal member 406 from decoupling from the distal member 404, at least absent a sufficient external force. The adapter 402 may further include a bearing 454 positioned within a distal portion of the distal member 404 and configured to enable the end effector 202, 302 to rotate relative to the distal member 404 without placing rotational torque on the distal member 404 that causes rotation of the distal member 404. The adapter 402 may also include a distal ring 456 positioned within the distal portion of the distal member 404. The distal ring 456 may be configured to abut or receive the stop 210, 310 of the end effect effector 202, 302 when the adapter 402 is disposed on the end effector 202, 302 as described herein.

Referring back to FIG. 5A, a partially exploded view of the adapter 402 and a first end effector 202 is illustrated. The first end effector 202 includes distal portion 208 for manipulating tissue and proximal portion 206 defining a retainer 214 for removably attaching the first end effector 202 to the surgical handpiece 108. As described above, the first end effector 202 may comprise a drill bit, a reamer, or similar cutting tool. The first end effector 202 may also comprise a screwdriver or a similar tool for inserting and/or placing a medical implant. Other configurations are contemplated. As illustrated in FIG. 15, the adapter 402 and tracker 502 may be coupled to a variety of different end effectors 202, 302. For example, a first end effector 202 may comprise a driver for inserting an implant, a second end effector 302 may comprise a calibration body, a third end effector 202B may comprise a drill for boring a hole, and a fourth end effector 202C may comprise a tap for defining threads within the bore created by the drill.

Referring again to FIG. 5A, the first end effector 202 may further comprise a retainer 214. The retainer 214 may comprise an annular recess in the proximal portion 206 of the end effector 202. For example, as illustrated in FIGS. 6A and 7B, the retainer 214 is realized with a V-shaped recess defined in the proximal portion 206 of the first end effector. As described above, the retainer 214 is configured to cooperate with the retention feature 180 of the receiver 178 on the surgical instrument 106 to removably secure the first end effector 202 to the surgical instrument 106. While the retainer is illustrated as a recessing have a V-shaped profile throughout the drawings, it is contemplated that the recess may be defined in alternate shapes that cooperate with the retention feature 180 of the receiver 178 or the surgical instrument 106 described above. For example, the retainer 214 may comprise a recess defined in the shaft 204 having a square-shaped profile, with the opposing surfaces of the recess arranged to be generally parallel to one another.

The first end effector 202 may also comprise a stop 210 arranged between the proximal portion 206 and the distal portion 208. Referring to FIG. 6A, the stop 210 comprises an annular body disposed on the shaft 204 of the first end effector 202. The stop 210 may be formed as part of the shaft 204 and configured as a protrusion that encircles and extends outwardly from an outer surface of the shaft 204. Alternatively, the stop 210 may be configured as a separate component that is attached to the shaft 204 of the first end effector 202. For example, the stop 210 may comprise a bearing or washer that is coupled to the shaft 204 of the end effector 202. The stop 210 may be press-fitted onto the shaft 204. Alternatively, the stop 210 may be coupled to the shaft via a weld, epoxy, or similar adhesive. It will be appreciated that the stop 210 could be defined by various components and/or structural features of the surgical instrument 106. Other configurations are contemplated.

The stop 210 is positioned at a defined location between the proximal portion 206 and the distal portion 208 of the first end effector 202 and is configured to abut the distal member 404 of the adapter 402. For example, the stop 210 may be positioned on the shaft 204 of the first end effector 202 at a known distance from the retainer 214. The distance that the stop 210 is spaced from the retainer 214 may be based on the length of the combination of the distal member 404 and the proximal member 406 of the adapter 402. The known distance between the stop 210 and the retainer 214 may be selected to compress the biasing member 422 a known distance when the first end effector 202 is coupled to the surgical handpiece 108. The distance that the biasing member 422 is compressed may be determined based on geometric and/or material properties of the biasing member 422, wherein the distance the biasing member 422 is compressed is configured to generate a predetermined amount of friction between the distal member 404 and the proximal member 406 of the adapter 402 as they are compressed by the combination of the stop 210 and the receiver 178 of the surgical handpiece 108. How the predetermined amount of friction force is achieved will be described in greater detail below.

In one exemplary configuration, the distance between the stop 210 and the retainer 214 is configured such that the biasing member 422 compresses to a distance (or by an amount) that generates a predetermined amount of friction between the distal member 404 and the proximal member 406 of the adapter 402 by the combination of the stop 210 and the receiver 178, where the predetermined amount of friction is sufficient to limit rotation of the distal member 404 relative to the proximal member 406. As will be appreciated by the subsequent description below, the predetermined amount of friction, created by the adapter 402 being compressed between the receiver 178 and the stop 210, may limit or otherwise prevent "free" rotation of the distal member 404 of the adapter 402 relative to the proximal member 406 absent the application of an additional force being applied to the distal member 404, such as an external force applied to the tracker mount 408. By contrast, when the adapter 402 is attached to the first end effector 202, but the first end effector 202 is detached from the surgical handpiece 108, the receiver 178 is not present, in combination with the stop 210, to compress the adapter 402. In this arrangement, the first end effector 202 being detached from the surgical handpiece 108, the distal member 404 of the adapter 402 may spin freely relative to the proximal member 406.

The stop 210 may also be configured to position the adapter 402 at a known distance from the distal portion 208 of the first end effector 202. Here, it will be appreciated that positioning the adapter 402 at a known distance from the distal portion 208 of the first end effector 202 can allow the navigation system 102 to precisely and accurately determine the position and/or orientation of the distal portion 208 of the first end effector 202 relative to the surgical site ST and/or target object. For example, the navigation system 102 may be configured to determine the position and/or orientation of the distal portion 208 of the first end effector 202 using the detected position of the tracker 502 that is coupled to the adapter 402 and the known position of the adapter 402 relative to the distal portion 208.

Referring again to FIG. 15, illustrating a variety of different end effectors 202, 202B, 202C, 302 that the adapter 402 and tracker 502 may be coupled to, it should be appreciated that each of the end effectors 202, 202B, 202C, 302 may constructed to have the same length, i.e. the same distance between the distal end of the distal portion 208, 308 and the proximal end of the proximal portion 206, 306, such that the adapter 402 is positioned at a common distance from the distal end of the distal portion 208, 308 of each of the end effectors 202, 202B, 202C, 302. Alternatively, it is also contemplated that the end effectors 202, 202B, 202C, 302 may have different lengths, and the stop 210, 310 may be configured to position the adapter 402 at a common distance from the distal end of the distal portion 208, 308 of each of the various end effectors 202, 202B, 202C, 302.

Referring again to FIG. 5A, the first end effector 202 may also comprise a recess 212, as described above, that is configured to receive the detent 420 of the coupler 418 on the adapter 402 when the adapter 402 is attached to the first end effector 202. The recess 212 on the proximal portion 206 of the first end effector 202 may be configured to removably attach the adapter 402 to the first end effector 202. As described above, the biasing member 422 may be compressed by the distal member 404 and the proximal member 406 as they are compressed between the receiver 178 of the surgical handpiece 108 and the stop 210 on the end effector 202. Therefore, the size and shape of the recess 212 defined in the outer surface of the proximal portion 206 of the end effector 202 must allow for sufficient lateral movement of the detent 420 within the recess 212 to allow the distal member 404 to abut the stop 210 when the end effector 202 is attached to the surgical handpiece 108 causing the biasing member 422 to compress when the receiver of the surgical handpiece 108 engages the abutment interface 424 of the proximal member 406. Furthermore, the shape of the recess 212, in combination with the detent 420, are configured to allow the adapter 402, specifically the distal member 404, to be rotated about the end effector 202 and/or relative to the stop 210 or surgical handpiece 108.

In the representative configuration depicted in the FIGS. 6A and 6B, the recess 212 is an annular recess defined in the shaft 204 of the first end effector 202 and configured to receive the detent 420 of the adapter 402, as illustrated in FIG. 6B. The recess 212 encircles the shaft 204 such that once the detent 420 is positioned within the recess 212, the adapter 402 may be rotated about the shaft 204 and the detent 420 remains in the recess 212 securing the adapter 402 to the first end effector 202. While the illustrated configurations depict the recess 212 completely encircling the shaft 204 of the first end effector, it is contemplated that the recess 212 may be configured as a groove or differently-shaped formation that only partially encircles the shaft 204. In operation, this configuration would prevent the adapter from being fully rotated 360 degrees about the shaft 204 while still permitting the adapter 402 to be rotated about a portion of the shaft 204, which may be sufficient to maintain visibility between the tracker 502 and the navigation system 102. For example, when using a surgical handpiece 108 of the type illustrated in FIGS. 2A and 2B, it may only sometimes be necessary to rotate the adapter 402 about certain types of end effectors 202, 302, and may generally remain positioned on the underside of the end effector 202, 302 adjacent the grip portion 172. In this scenario, it may be sufficient that the end effector 202, 302 employ a recess 212, 312 that only partially encircles the end effector 202, 302, arranged such as to permit coupling the end effector 202, 302 to the surgical handpiece 108 so that the recess 212, 312 is positioned on the top of the end effector 202, 302 relative to the surgical handpiece 108. However, it will be appreciated that other configurations are contemplated.

Figure 11A:
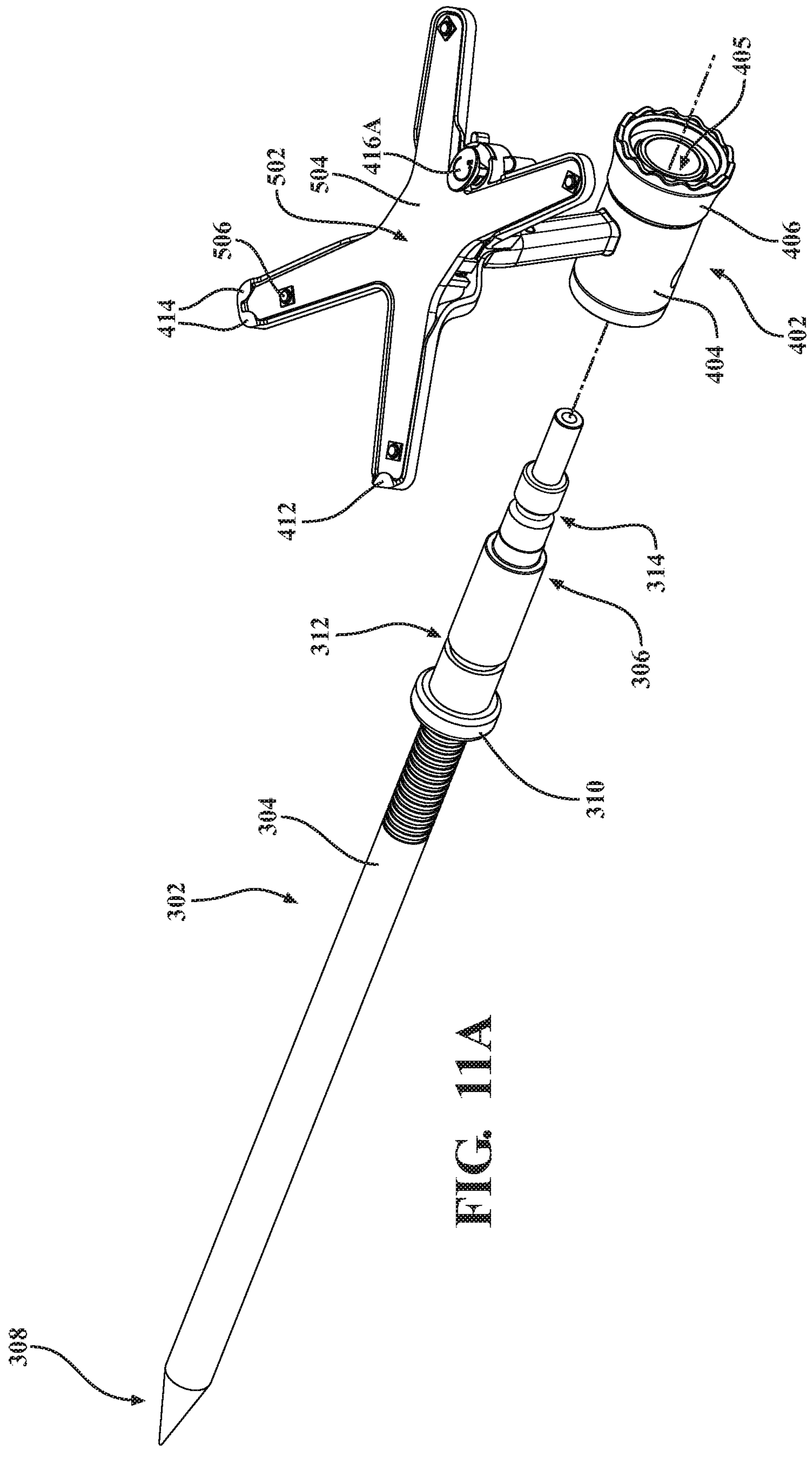
FIG. 11A is a partially exploded perspective view of a rotational adapter including a tracker with a second configuration of an end effector that may be used with the surgical instrument of FIGS. 2A-4.
Figure 11B:
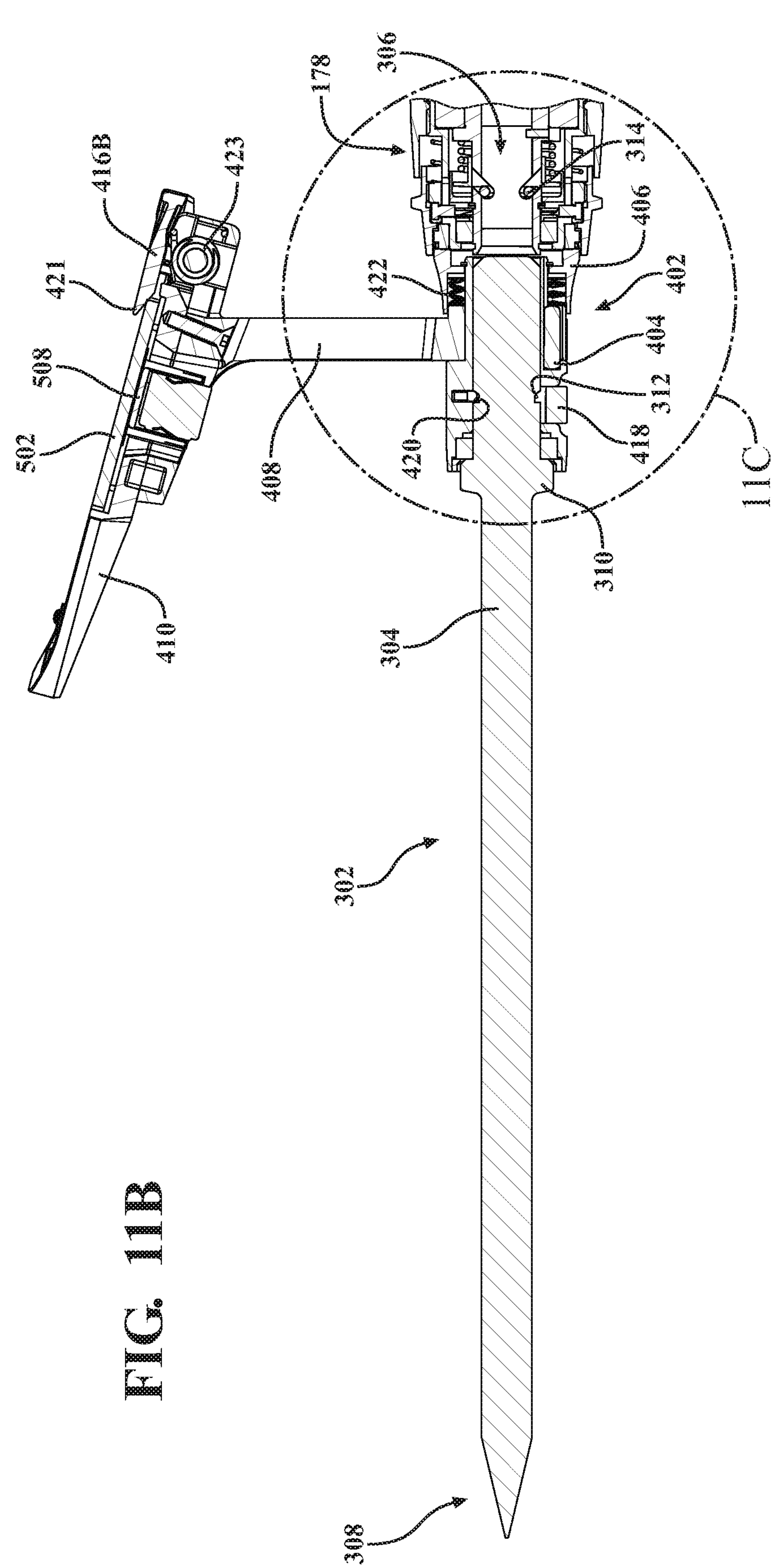
FIG. 11B is a sectional view of the rotational adapter for coupling the tracker to a second configuration of an end effector, the rotational adapter illustrated in a decompressed state when not coupled a surgical handpiece.
Figure 11C:
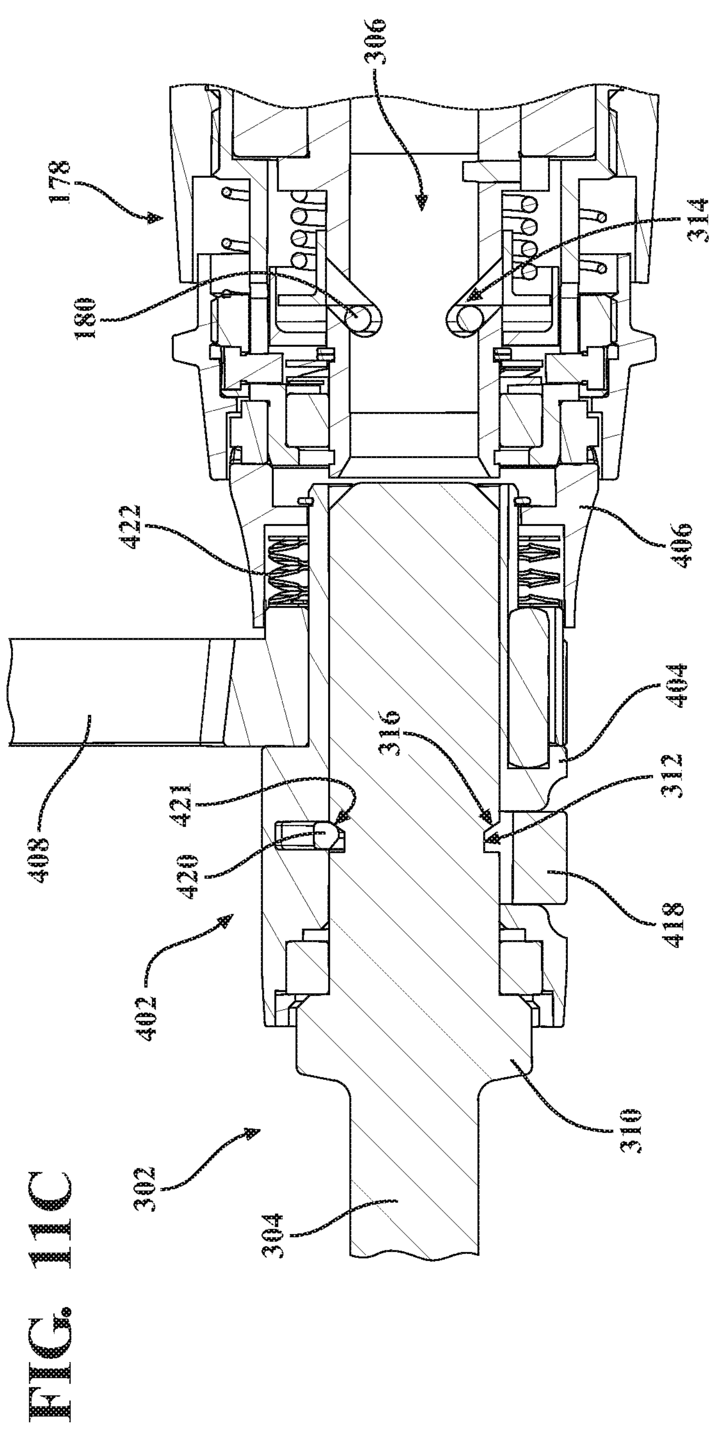
FIG. 11C is a partial sectional view of the rotational adapter of FIG. 11B for coupling the tracker to the second configuration of an end effector, the rotational adapter illustrated in a compressed state when coupled to a surgical instrument.

Referring to FIGS. 11A-11C, the adapter 402 is illustrated with a second configuration of an end effector 302. FIG. 11A is a partially exploded view of the adapter 402 and the second end effector 302. Those having ordinary skill in the art will appreciate that the same adapter 402 may be utilized to attach the instrument tracker 502 to multiple end effectors 202, 302 and/or to end effectors 202, 302 of different types, styles, configurations, and the like. In some configurations, the second end effector 302 may comprise or otherwise be realized as a calibration body 302 configured to function as a pointer or similar instrument to calibrate the position of the instrument tracker 502 with regard to the adapter 402, and/or to facilitate registration of various components of the navigation system 102. Other configurations are contemplated.

The second end effector 302 may include, define, or otherwise utilize components, structural features, and the like that are substantially similar (or even identical) to those described above in connection with the first end effector 202 (see FIG. 5A-7B). For example, the second end effector 302 may include a distal portion 308 for touching off on a one or more locations as part of a calibration procedure, and a proximal portion 306 defining a retainer 314 for removably attaching the second end effector 302 to the surgical handpiece 108. Here too, it will be appreciated that the retainer 314 of the second end effector 302 may have the similar characteristics and/or functionality as the retainer 214 of the first end effector 202 described above. For example, in operation, the retainer 314 of the second end effector 302 may be utilized to removably couple the second end effector 302 to the surgical instrument 106. The surgical instrument 106 may then be manipulated by the user to touch the distal portion 308 of the second end effector 302 to points at known locations to allow the navigation system 102 to calibrate the position of the tracker 502 relative to the adapter 402. It is also contemplated that the second end effector 302 may be utilized to calibrate the position of the tracker 502 relative to the adapter 402 without coupling the second end effector 302 to the surgical instrument 106. For example, the adapter 402 may be coupled to the second end effector 302, and the user may manipulate the second end effector 302 directly to touch the distal portion 308 of the second end effector 302 to points at known locations to allow the navigation system 102 to calibrate the position of the tracker 502 relative to the adapter 402. Other configurations are contemplated.

The second end effector 302 may also comprise a recess 312 configured to receive the detent 420 of the coupler 418 on the adapter 402 when the adapter 402 is attached to the second end effector 302. However, as described above, it is contemplated that the second end effector 302 does not require coupling of the second end effector 302 to the surgical handpiece 108 for the purpose of calibrating the position of the tracker 502 relative to the adapter 402. Without the surgical handpiece 108, there is no combination of the receiver 178 and the stop 310 to compress the biasing member 422 and cause the adapter 402 to abut the stop 310. Furthermore, during calibration, it will be appreciated that the adapter 402 needs to be positioned at a specific distance from the distal portion 308 of the second end effector 302 in order for the navigation system to accurately determine the position of the tracker 502 relative to the adapter 402. One way of accomplishing this is to utilize the position, the size, and/or the shape of the recess 312 of the second end effector 302 to locate the adapter 402 relative to the distal portion 308 of the second end effector 302. For example, the position where the recess 312 is defined in the shaft 304 of the second end effector 302 may be configured to cause the adapter 402 to abut the stop 310 when the detent 420 is disposed in the recess 312. The width of the recess 312 in the shaft 304 may also be configured to snugly receive the detent 420, such as to prevent lateral movement along the length of the second end effector 302 when the detent 420 is disposed in the recess 312.

The shape and size of the recess 312 may also be configured to correspond to the shape of the detent 420, such that the combination of the detent 420 and recess 312 urge the adapter 402 toward the stop 310, causing the adapter 402 to abut the stop 310 when the detent 420 is disposed in the recess 312. For example, the recess 312 may comprise an angled surface 316 and the detent 420 may comprise an opposing angled surface 421. The opposing angled surfaces 421 may be arranged such that when the detent 420 is disposed in the recess 312, the angled surface 421 of the detent 420 engages the angled surface 316 of the recess 312 such that the opposed sloped surfaces 316, 421 urge the adapter 402 toward the stop 310. Other configurations are contemplated.

Referring to FIG. 15, it is contemplated that each of the adapters 402 associated with the particular end effector 202, 202B, 202C, 302 may be configured to be coupled to the second end effector 302 comprising the calibration body in the manner described above, where each of the adapters 402 comprise the detent 420 having the angled surface 421 configured to engage the angled surface 316 of the second end effector to position the particular adapter 402 on the second end effector 302 at the known location relative to the distal end of the distal portion 308 of the second end effector 302. This allows the position of each of the trackers 502A, 502B, 502C, 502D to be calibrated relative to the adapter 402 it is coupled to using the unique pattern of the markers 506A, 506B, 506B, 506D of the respective trackers 502A, 502B, 502C, 502D.

As illustrated in the FIG. 11A, the recess 312 is an annular recess defined in the shaft 304 of the second end effector 302 and configured to receive the detent 420 of the adapter 402. As noted above, the recess 312 encircles the shaft 304 such that once the detent 420 is positioned within the recess 312, the distal member 404 of the adapter 402 may be rotated about the shaft 304 and the detent 420 remains in the recess 312 securing the adapter 402 to the first end effector 202. Here too, while the recess 312 that encircles the shaft 304 of the second end effector 202 in the illustrated configurations, it is contemplated that the recess 312 may be realized as a groove or other formation that only partially encircles the shaft 304. The recess 312 may also be configured as a single indent configured to receive the detent 420. Here, it will be appreciated that employing a partial recess or an indent would facilitate preventing the distal member 404 of the adapter 402 from being fully rotated 360 degrees about the shaft 304. However, the recess 312 would nevertheless function to attach the adapter 402 to the second end effector 302. Here, in some configurations, such as where second end effector 302 is configured as a calibration body for the purpose of calibrating the position of the tracker 502 to the adapter 402, it may not be necessary to be able to rotate the distal member 404 of the adapter 402 about the second end effector 302. For the purpose of calibration, for example, the position of the adapter 402 on the second end effector 302 may be more important than being able to rotate the distal member 404 of the adapter 402 about the second end effector 302. In such a scenario, the partial recess and/or the single indent would serve the purpose of attaching the adapter 402 to the second end effector 302 at a specific location on the second end effector 302.

Figure 12:
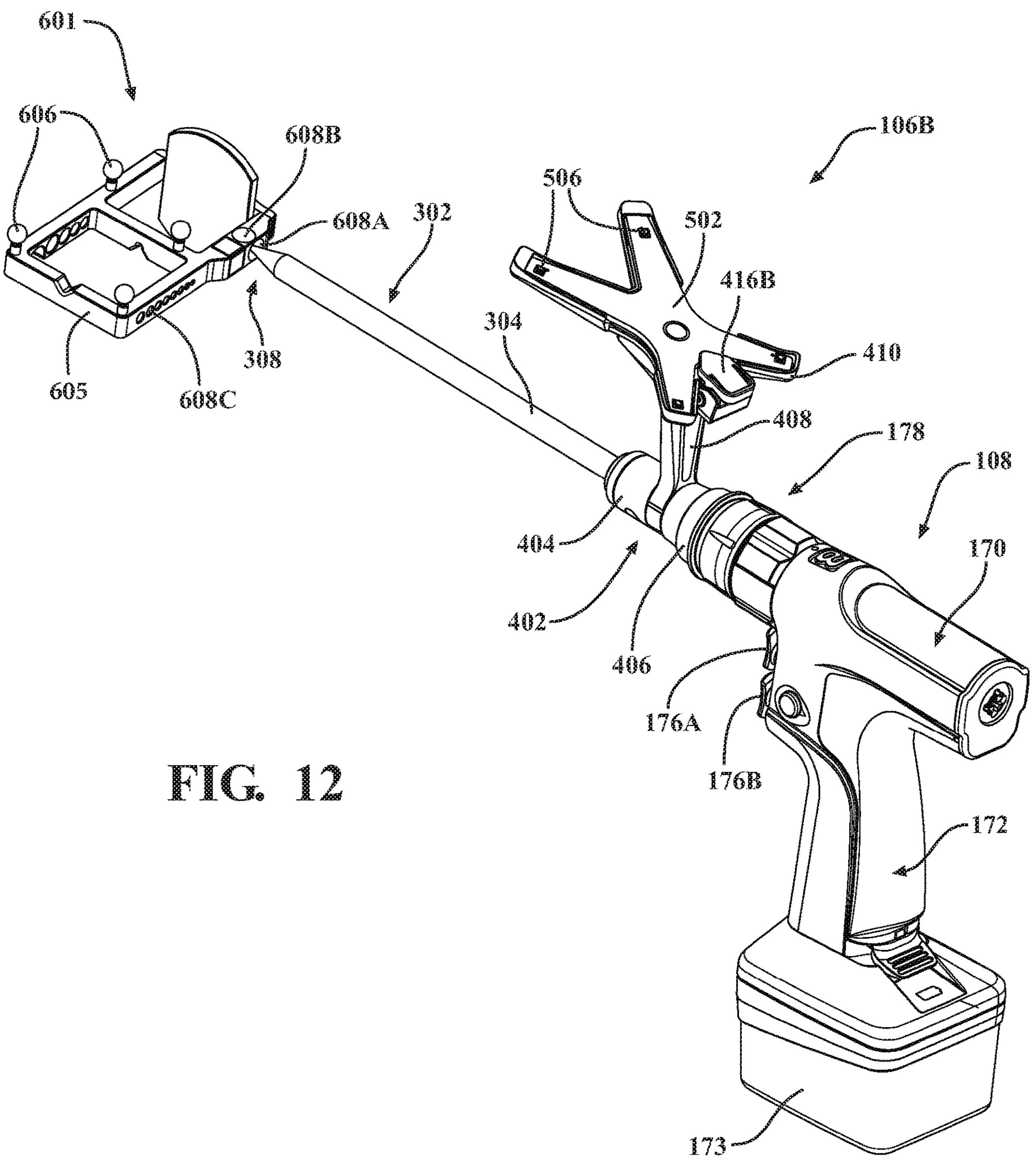
FIG. 12 is a perspective view of a surgical instrument including a rotational adapter and the second configuration of the end effector of FIGS. 11A-11C, the rotational adapter and the second configuration of the end effector configured to calibrate a position of a tracker relative to the rotational adapter with the navigation system using a calibration block.

Referring to FIG. 12, an exemplary arrangement of the surgical instrument 106B is illustrated with a calibration block 601. The surgical instrument 106B, including the surgical handpiece 108, end effector 302 and the adapter 402 including the tracker may function as described above. The calibration block 601 may comprise a structure 605, and two or more markers 606 coupled to the structure 605. The structure 605 may also define one or more touch points 608A, 608B, 608C. The touch points 608A, 608B, 608C may each comprise a recess, indent, or the like and identify a known location on the structure relative to the markers 606 for the end effector 302, which may also be referred to as a calibration body, to contact to calibrate the position of the tracker 502 relative to the adapter 402.

In operation, a method of calibrating an adapter 402 with a navigation system 102 may comprise coupling an adapter 402, including a tracker 502, to the calibration body 302. The navigation system 102 may then observe the calibration body 302 as the calibration body 302 is touched to a number of known locations. Each known location may be a touch point 608A, 608B, 608C on an object such as the calibration block 601 including one or more markers 606 that are identifiable by the navigation system 102. Additionally or alternatively, the known locations a known point on the patient that was identified using a patient tracker 132A and/or patient image data ID. This will allow the surgical navigation system to calibrate a position of the instrument tracker 502 relative to the adapter 402.

The adapter 402, including the tracker 502, may then be removed from the calibration body 302. The adapter 402 and tracker 502 may then be coupled to a different end effector 202, and the end effector 202 may be coupled to a surgical handpiece 108. Coupling the end effector 202 to the surgical handpiece 108 may engage the proximal member 406 causing the biasing member 422 of the adapter 402 to compress and urge the distal member 404 of the adapter 402 away from the surgical handpiece 108 and toward the stop 210 of the end effector 202. The compression of the biasing member 422 of the adapter 402 between the surgical handpiece 108 and the stop 210 will create a predetermined amount of friction between the distal member 404 and the proximal member 406 limiting rotational movement of the distal member 404 of the adapter 402 relative to the proximal member 406. Here, it will be appreciated that coupling the end effector 202 to the surgical handpiece 108, which causes the biasing member 422 to position distal member 404 of the adapter 402 adjacent the stop 210 of the end effector 202, also results in the tracker 502 coupled to the adapter 402 being positioned at a known position relative to a distal portion 208 of the end effector 202.

The method may also comprise identifying the pose of the end effector 202 based on the calibrated position of the tracker 502 relative to the adapter 402 and a known position of the adapter 402 relative to the end effector 202. The method may also comprise applying an external force to distal member 404 of the adapter 402 to rotate the tracker 502 about the end effector 202 so that the tracker 502 remains in view of the surgical navigation system 102.

Referring back to FIGS. 6A and 6B, a partial sectional view of the end effector 202 coupled to the receiver 178 of the of the surgical handpiece 108 is illustrated. As described above, the adapter 402 is coupled to an end effector 202, 302 by sliding the adapter 402 onto the proximal portion 206, 306 of the end effector 202, 302. The detent 420 of the coupler 418 on the adapter 402 is seated in the recess 212, 312 defined in the shaft 204, 304 of the end effector 202, 302 to secure the adapter 402 to the end effector 202, 302. Prior to attaching the end effector 202, 302 to the surgical handpiece 108, the end effector 202, 302 and adapter 402 are configured such that the distal member 404 of the adapter 402 may spin freely relative to the proximal member 406 and about the shaft 204, 304 of the end effector 202, 302.

The end effector 202, 302 may then be attached to the surgical handpiece 108 by inserting the proximal portion 206, 306 of the end effector 202, 302 into the receiver 178 to engage the retention feature 180 of the receiver 178 with the retainer 214, 314 of the end effector 202, 302. As proximal portion 206, 306 of the end effector 202, 302 is inserted into the receiver 178, the abutment interface 424 defined by the proximal member 406 will engage the receiver 178, with the biasing member 422 urging the distal member 404 of the adapter 402 away from the receiver 178 and causing the distal member 404 of the adapter 402 to abut the stop 210, 310 of the end effector 202, 302.

Once the distal member 404 of the adapter 402 abuts the stop 210, 310, the biasing member 422 compresses as the proximal portion 206, 306 of the end effector 202, 302 is inserted further into the receiver 178 until the retention feature 180 engages the retainer 214, 314, thereby securing the end effector 202, 302 to the surgical handpiece 108. As described above, when the biasing member 422 is compressed between the distal member 404 and the proximal member 406 by the receiver 178 urging the adapter against the stop 210, 310, a predetermined amount of friction will be generated between the receiver 178 and the proximal member 406, as well as between the distal member 404 and the proximal member 406. The adapter 402 may be configured such that the predetermined amount of friction generated by compressing the biasing member 422 between the distal member 404 and the proximal member 406 is great enough to limit free rotation (and/or even prevent free rotation) of the distal member 404 of the adapter 402 relative to the proximal member 406. Upon detaching the end effector 202, 302 from the surgical handpiece 108, the biasing member 422 decompresses, and the distal member 404 of the adapter 402 will once again be able to spin freely relative to the proximal member 406 and about the shaft 204, 304 of the end effector 202, 302.

FIGS. 6A and 6B illustrate the biasing member 422 in a compressed state when the adapter 402 is attached to the end effector 202 and the end effector 202 is coupled to the receiver 178 of the surgical handpiece 108. As described above, coupling the end effector 202, 302 to the receiver 178 causes the biasing member 422 to compress, placing it in the compressed state. In the compressed state, the distal member 404 and the proximal member 406 of the adapter 402 have a compressed length spanning a distance D1, with the biasing member 422 having a compressed length spanning a distance D2.

Referring back to FIGS. 7A and 7B, a side view of the adapter 402 is shown illustrating the biasing member 422 in a decompressed state. Specifically, FIG. 7A illustrates the adapter 402 detached from both the surgical handpiece 108 and an end effector 202, 302, and FIG. 7B illustrates the adapter 402 disconnected from the surgical handpiece 108 but disposed on the end effector 202. In the decompressed state, the distal member 404 and the proximal member of the adapter 402 have an overall length spanning a decompressed length D3, with the biasing member 422 spanning a decompressed length D4. The compressed length D1 of the adapter 402 and the compressed length D2 of the biasing member 422 are shorter than decompressed length D3 of the adapter 402 and the decompressed length D4 of the biasing member 422. It will be appreciated that the terms "distance" and "length" may be used interchangeably herein unless otherwise noted.

The distance the biasing member 422 is compressed when the end effector 202, 302 is coupled to the receiver 178 of the surgical handpiece 108 may be determined by the structural features of the end effector 202, 302. Specifically, the distance the biasing member 422 is compressed may be based on the distance D5 between the stop 210, 310 and the retainer 214, 314 of the end effector 202, 302. As illustrated in FIG. 7B, the location of the retainer 214, 314 determines the amount of the proximal portion 206, 306 of the end effector 202, 302 is inserted into the receiver 178. The amount of the proximal portion 206, 306 that is inserted into the receiver 178 in combination with the location of the stop 210, 310 on the end effector 202, 302 dictates the distance between the receiver 178 and the stop 210, 310, and the distance between the receiver 178 and the stop 210, 310 determines the distance the biasing member 422 is compressed. The distance that the biasing member 422 is compressed, in combination with the mechanical properties of the biasing member 422, determine the amount of frictional force that will be generated between the receiver 178 and the proximal member 406, as well as between the distal member 404 and the proximal member 406.

Thus, assuming the configuration of the adapter 402 remains constant, the predetermined amount of friction created to limit the rotation of the adapter 402 about the end effector 202, 302 may be varied from one end effector 202, 302 to the next by manipulating the distance D5 between the stop 210, 310 and the retainer 214, 314. For example, increasing the distance D5 between the stop 210, 310 and the retainer 214, 314 will reduce the distance the biasing member 422 is compressed, resulting in a lesser amount of friction being created between the receiver 178 and the proximal member 406, as well as between the distal member 404 and the proximal member 406. Meaning it would require less force to rotate the distal member 404 of the adapter 402 relative to the proximal member 406. Alternatively, decreasing the distance D5 between the stop 210, 310 and the retainer 214, 314 will increase the distance the biasing member 422 is compressed, resulting in a greater amount of friction being created between the receiver 178 and the proximal member 406, as well as between the distal member 404 and the proximal member 406. Meaning it would require a greater force to rotate distal member 404 of the adapter 402 relative to the proximal member 406.

Referring to FIGS. 13A-14B, an alternative configuration of an adapter 402B for attaching a tracker 502 to an end effector 202, 302 is illustrated. The adapter 402B includes all of the components and features of the adapter 402 described above, but, the distal member 404B and the proximal member 406B of the adapter 402B have been modified to include additional features.

Figures 13A, 13B:
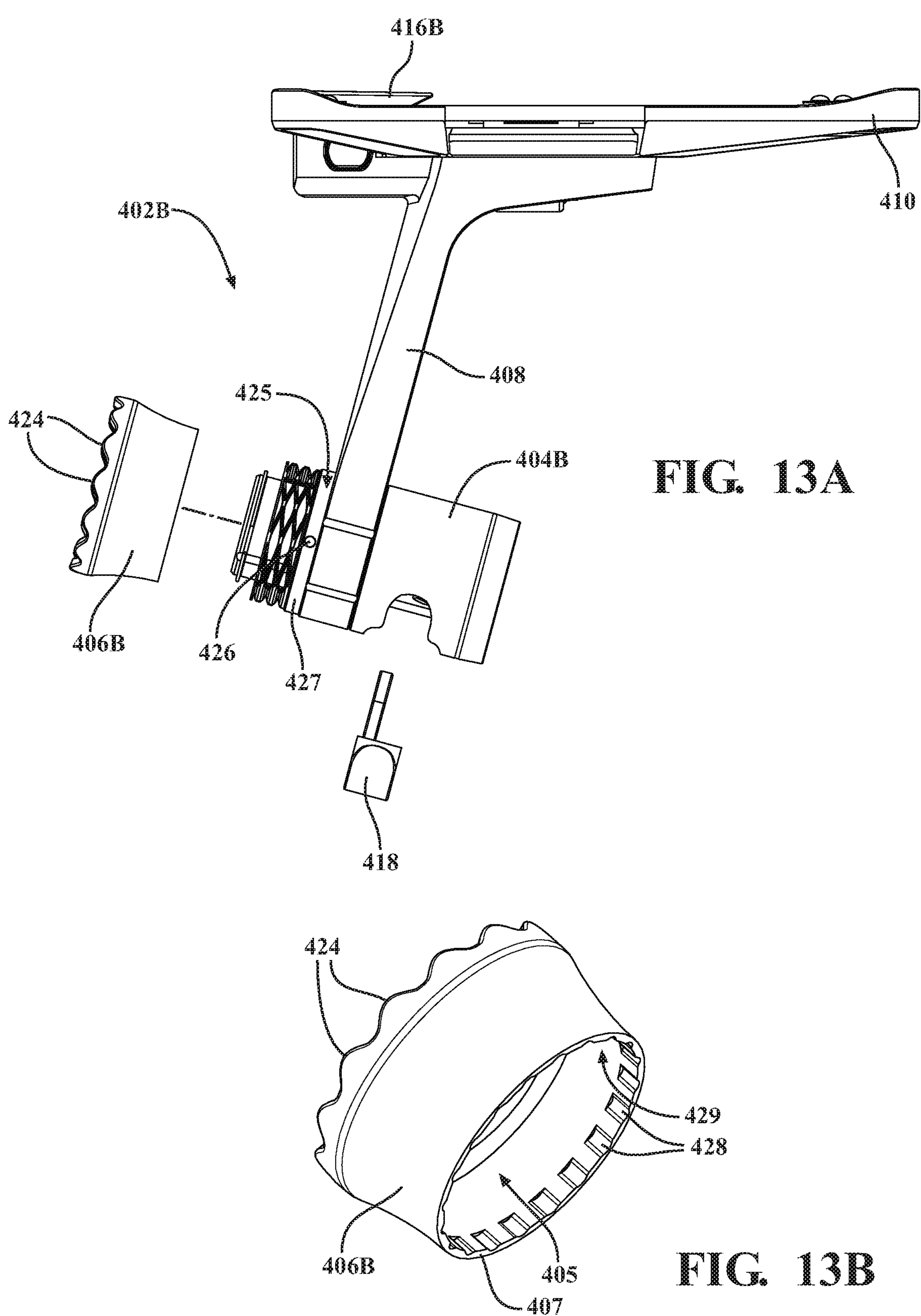
FIG. 13A is a partially exploded view of a second configuration of a rotational adapter including a detent and one or more recesses arranged on the rotational adapter to inhibit free rotation of the distal member of the rotational adapter relative to the proximal member.
FIG. 13B is a perspective view of the proximal member of the rotational adapter of FIG. 13A, illustrating a plurality of recesses arranged annularly about an interior surface of the proximal member.

Referring to FIG. 13A, the distal member 404B of the adapter 402B may optionally include a detent 426. The detent 426 may comprises a projection, protrusion, tab, or similar member extending from an outer surface 425 of a proximal end 427 of the distal member 404B. While only a single detent is illustrated in FIG. 13A, it is contemplated that a plurality of detents 426 may be annularly spaced about the outer surface 425 of the distal member 404B.

Referring to FIG. 13B, the proximal member 406B of the adapter 402B is illustrated. A distal end 407 of the proximal member 406B comprises an interior surface 429 defining an aperture 405 through the proximal member 406B. The aperture 405 is sized and shaped to receive the proximal end 427 of the distal member 404B. The proximal end 427 of the distal member 404B is sized to fit within the aperture 405 defined by the distal end 407 of the proximal member 406B and is configured to allow both rotational and axial movement of the distal member 404B relative to the proximal member 406B, as described above.

The proximal member 406B may optionally comprise at least one recess 428 defined in the interior surface 429 of the proximal member 406B proximate the distal end 407 of the proximal member 406B. For example, as illustrated in FIG. 13B, the proximal member 406B may comprise a plurality of recesses 428 defined by the interior surface 429. The plurality of recesses 428 may be annularly spaced about the interior surface 429.

The annularly spaced recesses 428 of the proximal member 406B and the at least one detent 426 of the distal member 404B may be configured to limit or even prevent the rotation of the distal member 404B relative to the proximal member 406B absent an external force being applied to the distal member 404B. This limiting and/or preventive rotation force provided by the combination of the detent 426 and the plurality of recesses 428 may be in addition to the friction force provided when the biasing member 422 of the adapter 402B is compressed as described above.

While FIGS. 13A and 13B illustrate the detent 426 on the distal member 404B of the adapter 402B and the recesses 428 formed in the proximal member 406B, the reverse configuration is contemplated. For example, the plurality of recess 428 may be annularly spaced about the outer surface 425 of the proximal end 427 of the distal member 404B and the detent 426 may be deposed on the interior surface 429 of the proximal member 406B. It is further contemplated that the detent 426 may be disposed on an interior surface of the distal member 404B and the plurality of annually spaced recesses 428 may be defined in an outer surface of the end effector 202, 302, such that the at least one detent 426 of the distal member 404B may be configured to limit or even prevent the rotation of the distal member 404B relative to the end effector 202, 302 absent an external force being applied to the distal member 404B.

Figures 14A, 14B:
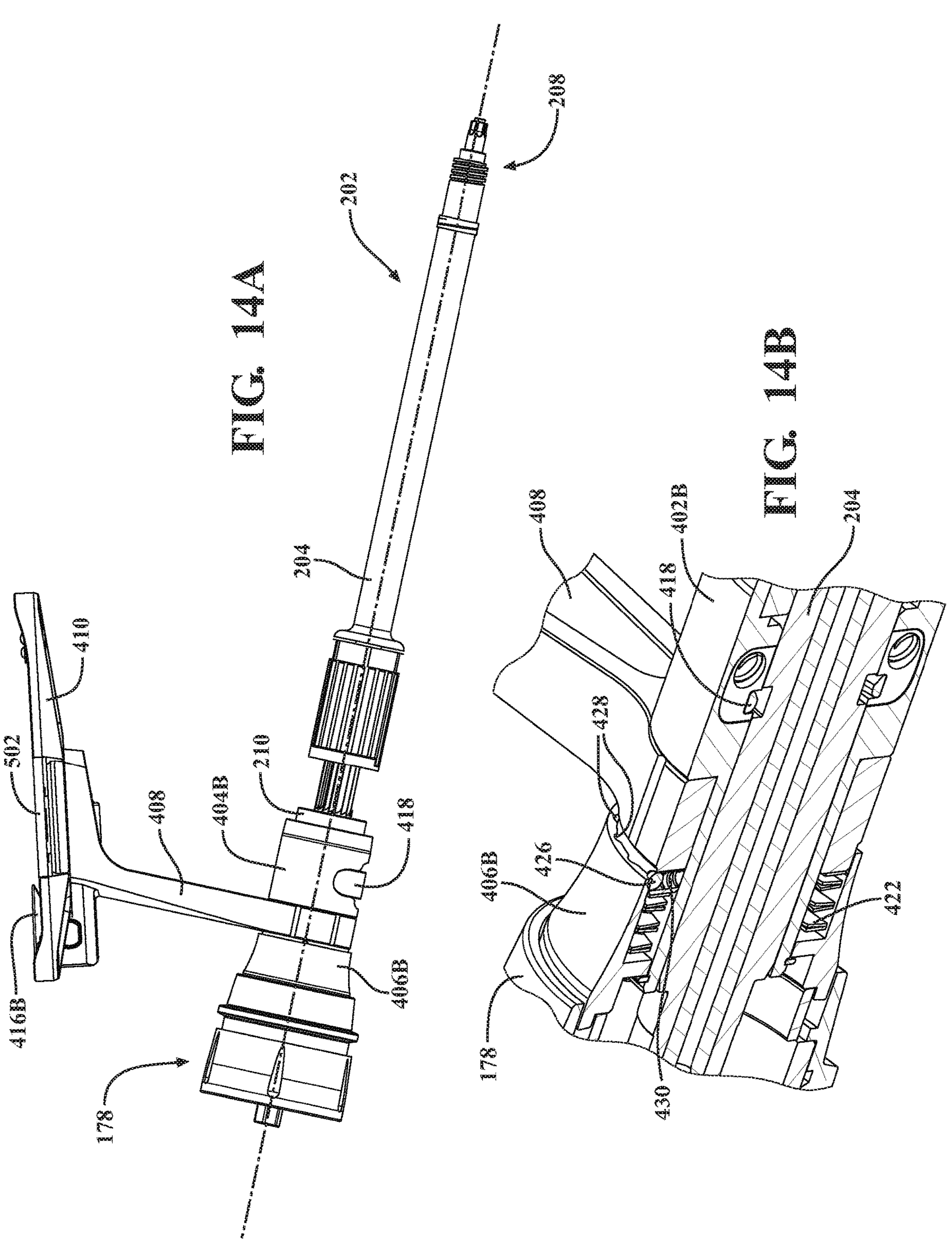
FIG. 14A is a side view of the second configuration of the rotational adapter of FIGS. 13A and 13B coupled to an end effector.
FIG. 14B is a partial sectional view of the second configuration of the rotational adapter coupled to the end effector of FIG. 14A, illustrating the detent of the distal member engaged with one of the recesses of the proximal member.

Referring to FIGS. 14A and 14B, an exemplary configuration of the adapter 402B coupled to an end effector 202 is illustrated. The adapter 402B may be coupled to the end effector 202 in the same manner as described above. The adapter 402B is similarly configured to have the biasing member 422 compress when the end effector 202 is attached to the surgical handpiece 108, generating a friction force between the receiver 178 and the proximal member 406B, as well as between the distal member 404B and the proximal member 406B to limit, or even prevent, the rotation of the distal member 404B relative to the proximal member 406B absent an external force being applied to the distal member 404B.

However, the adapter 402B also includes a detent 426 and plurality of recess 428 arranged to provide an additional anti-rotational force between the distal member 404B and the proximal member 406B. Referring to FIG. 14B, a sectional view of the adapter 402B is shown illustrating how the detent 426 of the distal member 404B interacts with the recess(es) 428 of the proximal member 406B to provide this additional anti-rotation force between the distal member 404B and the proximal member 406B. As illustrated in FIG. 14B, when the proximal end 427 of the distal member 404B is disposed within the aperture 405 defined by the distal end 407 proximal member 406B, the detent 426 is urged into one of the recesses 428 by a compression spring 430, creating an additional frictional force between the distal member 404B and the proximal member 406B configured to limit or prevent rotation of the distal member 404B relative to the proximal member 406B. Detent 426 and recess(es) 428 are defined such that the anti-rotational force may be overcome by the application of an external force to the distal member 404B. Applying an external force to the distal member 404B may allow the distal member 404B to be rotated relative to the proximal member 406B to reposition the tracker mount 408 and tracker 502 relative to the surgical handpiece 108 to maintain visual contact between the navigation system 102 and the tracker 502. The recesses 428 may be spaced apart on the interior surface 429 of the proximal member 406B in increments by which the distal member 404B may be rotated relative to the proximal member 406B.

Figure 24:
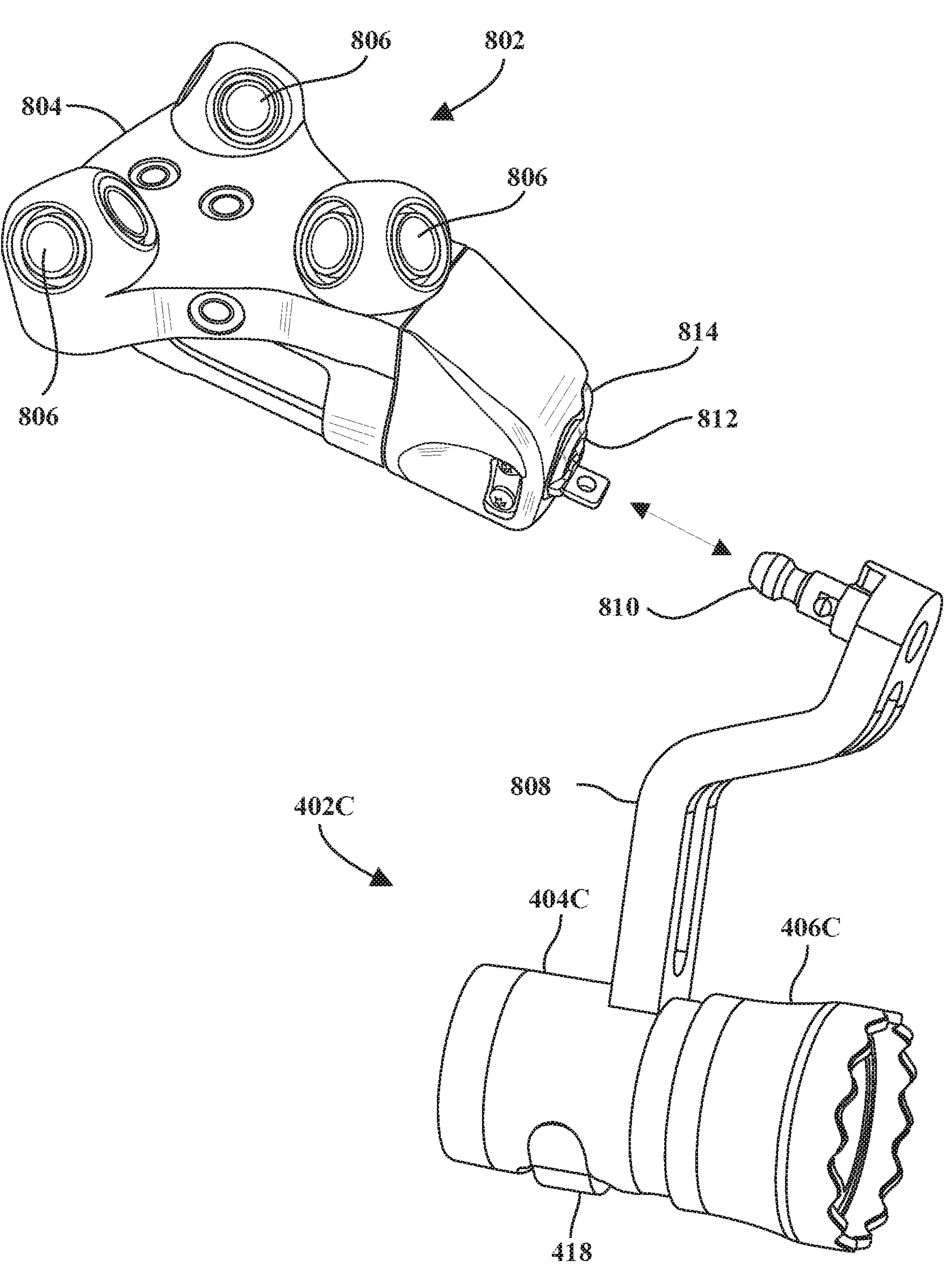
FIG. 24 is a perspective view of an alternative tracker and a third configuration of a rotational adapter for coupling the tracker to a surgical instrument.

Referring to FIGS. 24-26, an alternative configuration of an adapter 402C for attaching a tracker 802 to an end effector 202, 302 is illustrated. The adapter 402C includes many of components and features of the adapter 402 described above, as indicated by the similar reference numbers, but has been modified to accommodate an alternative tracker 802 and to include additional features.

Unlike the tracker 502, the tracker 802 may include a housing 804 and a plurality of markers 806, such as light emitting diodes, disposed in the housing 804 for emitting light detectable by the navigation system 102 to track a pose of the tracker 802. The markers 806 may be arranged such that at least three of the markers 806 are visible from a wide range of viewing angles, enabling the navigation system 102 to track a pose of the tracker 802 in further positions. Nevertheless, it is still possible that the view of markers 806 may become obscured during a surgical procedure, and the adapter 402C may thus enable the practitioner to reposition the tracker 802 to maintain visibility of the markers 806.

To this end, the adapter 402C may include a tracker mount 808 extending from the distal member 404C of the adapter 402C to couple to the tracker 802 to the distal member 404C. The tracker mount 808 may include an interface pin 810 for being received in a receiving interface 812 of the tracker 802. More specifically, the tracker 802 may include an interface button 814 that, when pressed, allows the interface pin 810 to be inserted in the receiving interface 812. Subsequent release of the interface button 814 may then function to releasably lock the interface pin 810 within the receiving interface 812.

Referring specifically to FIGS. 25 and 26, the adapter 402C may operate similarly to the adapter 402. More specifically, the adapter 402C may similarly include a coupling member 418 for engaging an end effector 202, 302 and a biasing member 422 configured to generate a frictional force between the distal member 404C and the proximal member 406C to restrict rotation of the distal member 404C relative to the proximal member 406C when the distal member 404C is disposed on the end effector 202, 302 and the end effector 202, 302 is coupled to the surgical handpiece 108. However, unlike the adapter 402, the adapter 402C may additionally include a tapered washer 820 disposed between the proximal member 406C and the biasing member 422. The tapered washer 820 may be rotationally fixed to the distal member 404C of the adapter, and may be configured to create a wedging effect between the distal member 404C and the proximal member 406C, which correspondingly creates a sliding friction to resist rotation of the distal member 404C relative to the proximal member 406C.

More specifically, the tapered washer 820 may be positioned between the distal member 404C and the proximal member 406C, and may include a beveled surface 822 generally facing a reciprocal surface 824 of the proximal member 406C. When the distal member 404C is disposed on the end effector 202, 302 and the proximal member 406C is engaged with the surgical handpiece 108 as described herein, the biasing member 422 may be compressed and thereby urge the beveled surface 822 into contact with the reciprocal surface 824 of the proximal member 406C. In this manner, the tapered washer 820 may wedge between the distal member 404C and the proximal member 406C to create the sliding friction that resists rotation of the distal member 404C relative to the proximal member 406C.

In addition to manipulating the distance D5 between the stop 210, 310 and the retainer 214, 314 of the end effector 202, 302, the predetermined amount of spring force and friction created to resist the rotation of the distal member 404C relative to the proximal member 406C may be varied by adjusting the material and taper angle of the tapered washer 820. The tapered washer 820 may also enable the adapter 402C to provide increased rotational resolution of the distal member 404C relative to the proximal member 406C, allowing the user further control of the positioning the tracker 802 relative to the surgical handpiece 108 and/or end effector 202, 302. Although FIGS. 24-26 illustrate the adapter 402C with the tracker mount 808 for coupling with the tracker 802, it is contemplated that the adapter 402C may be configured instead with the tracker mount 408 previously described in reference to the adapter 402 for enabling use of the tracker 502 with the adapter 402C.

Referring to FIGS. 16 to 19, an exemplary configuration of a tracker 502 is illustrated. As described above, during a surgical procedure, an instrument tracker 502 including one or more markers 506 may be coupled to the surgical instrument 106 to allow the navigation system 102 to determine the position and/or orientation of the surgical instrument 106. The markers 506 may be active light sources (e.g., LEDs) driven by an electrical current or passive reflectors arranged in a predefined pattern, and the navigation system 102 may be configured to detect the pose of the tracker 502, and correspondingly the pose of the surgical instrument 106, by detecting light signals received from the markers 506 and matching the detected light signals to the predetermined pattern. In some examples, the instrument tracker 502 may be a disposable tracker. An exemplary implementation of a disposable tracker is shown and described in International Application No. PCT/IB2020/059064, which is hereby incorporated by reference.

The tracker 502 may comprise a base 504 to which the light source type markers 506 are mounted. The base 504 may define opposing surfaces 503, 505 (also referred to as "opposing faces") of the tracker 502. For example, as illustrated in the figures, the base 504 may be in the form of a board with the opposing surfaces 503, 505 corresponding to the substantially parallel and planar surfaces of the board. In the illustrated examples, when the tracker 502 is mounted to the surgical instrument 106, the surface 505 may be positioned proximal the surgical instrument 106 such that the surface 505 is at least partially obscured from view of the navigation system 102 and practitioner, and the opposed surface 503 may be positioned distally the surgical instrument 106 such that the surface 503 is observable by the practitioner and navigation system 102. The markers 506 may thus be disposed on the surface 503 that is distally positioned so as to enable localization of the tracker 502 by the navigation system 102. The surface 503 may also be referred to as a "first surface 503" herein, and the surface 505 may also be referred to a "second surface 505" herein. In some instances, the base 504 may be a circuit board, such as a printed circuit board (PCB), described in greater detail below.

The base 504 of the tracker 502 may include a central portion 501 and a plurality of leg portions 510A, 510B, 510C, 510D that extend from the central portion 501. While the tracker 502 is illustrated in the figures as having a generally star-shaped base 504, it is contemplated that the base 504 may be formed in any number of suitable shapes, such as a square, rectangle, disk, triangle, plate, circle, sphere, trapezoid cube, or the like.

Figure 16:
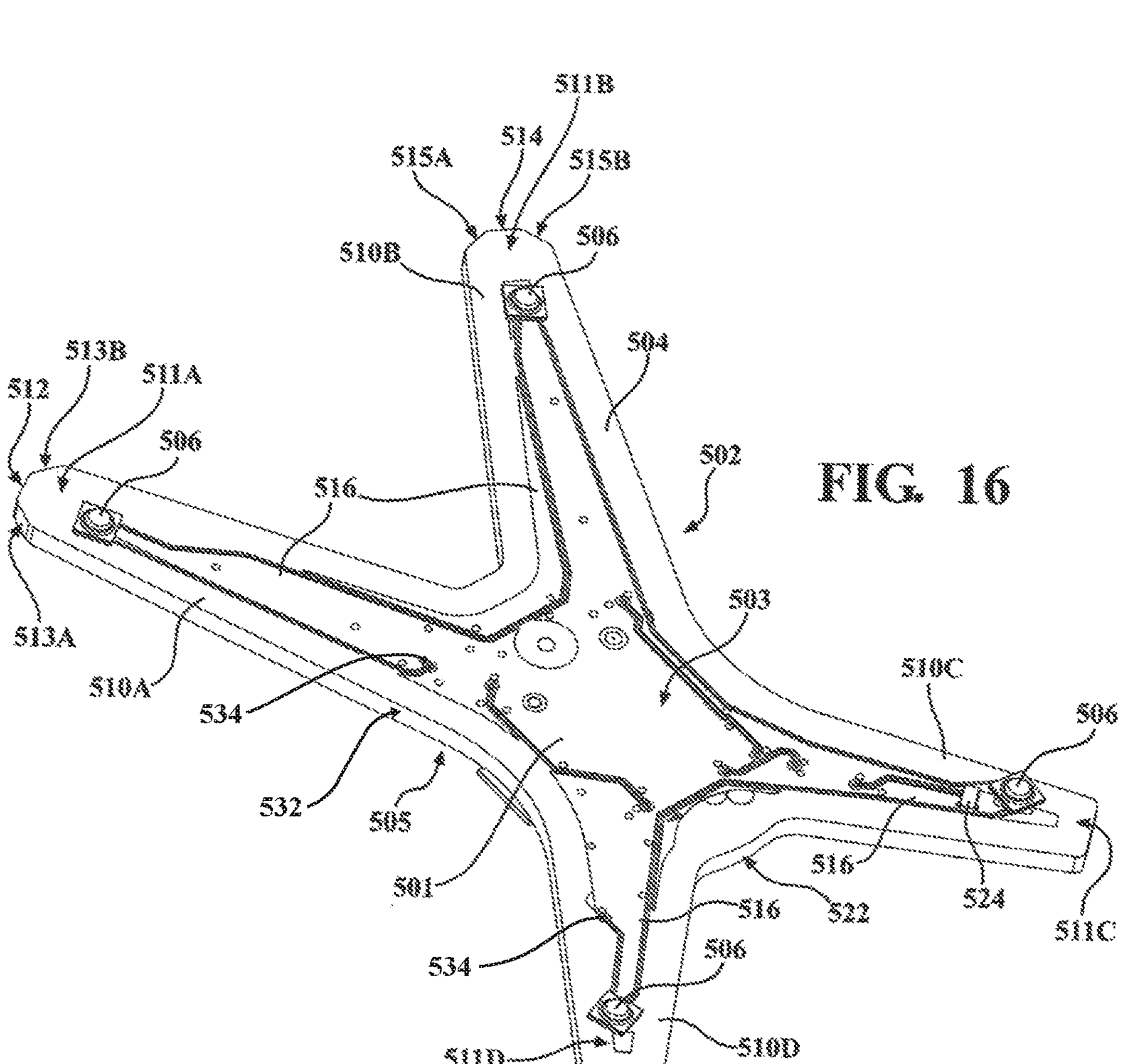
FIG. 16 is a perspective view of an exemplary configuration of a tracker including a plurality of markers disposed on a base and electrically interconnected by a trace.
Figures 17A, 17B:
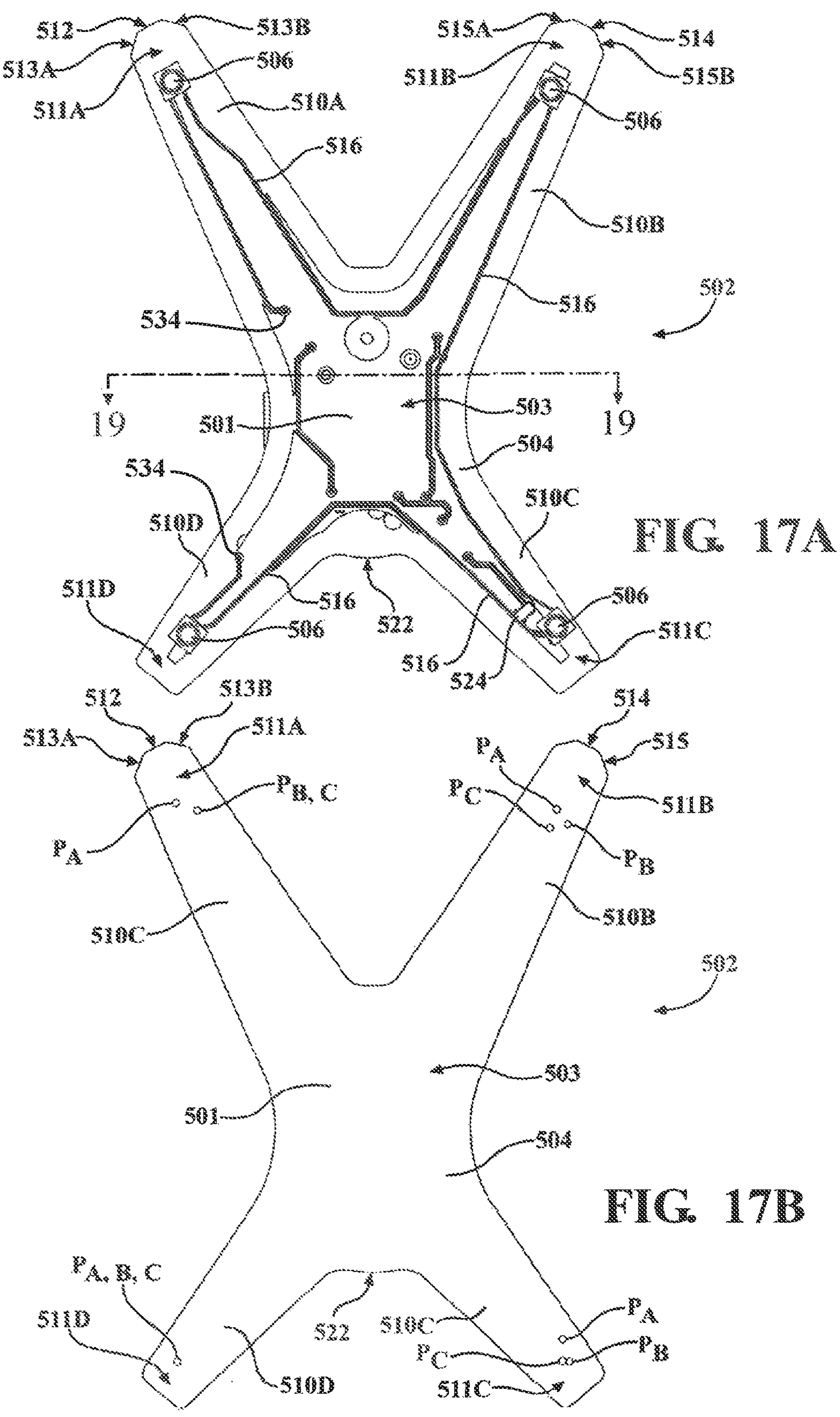
FIG. 17A is a top view of the tracker of FIG. 16 including a plurality of markers disposed on a base and electrically interconnected by a trace.
FIG. 17B is a top view of the tracker of FIG. 17A showing mounting locations for the plurality of markers.
Figure 18:
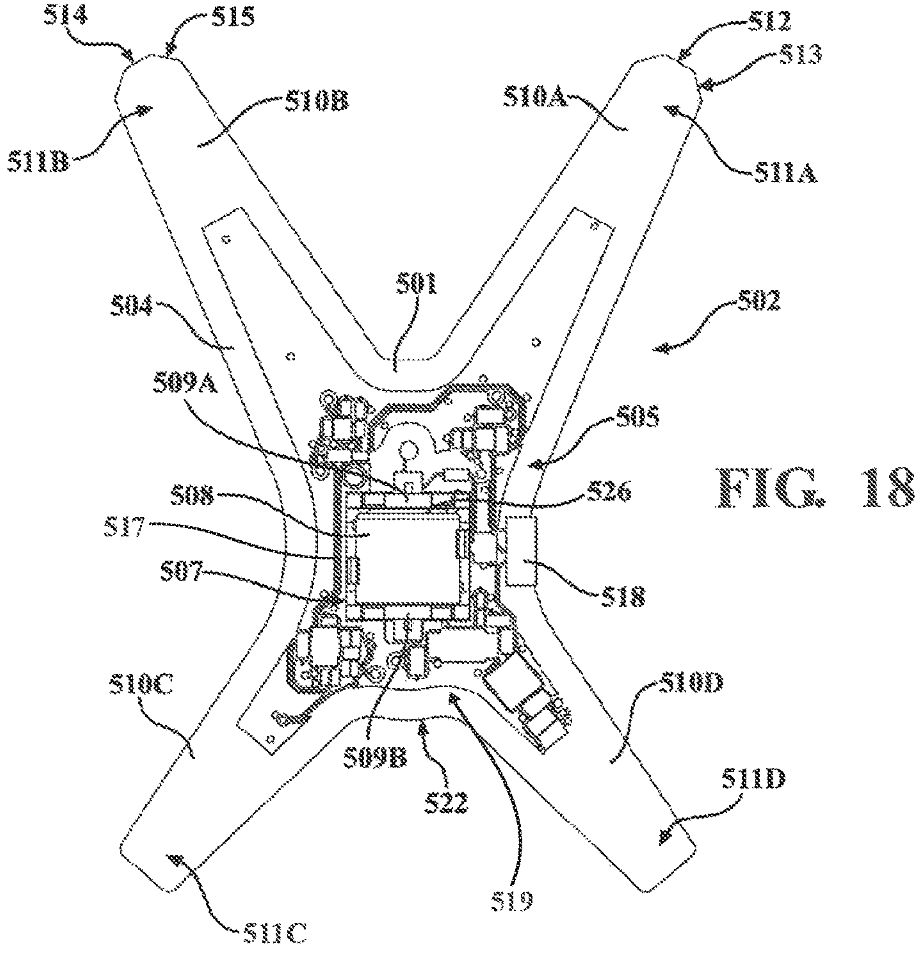
FIG. 18 is a bottom view of the tracker of FIG. 16 including a battery mount with one or more terminals for connecting a battery to the markers by a trace.

As described above, the tracker 502 may be coupled to a surgical instrument 106 using an adapter 402 including a tracker mount 408. One or more of the leg portions 510A, 510B, 510C, 510D of the tracker 502 may be shaped to assist with coupling the tracker 502 to the tracker mount 408. For example, as illustrated in FIGS. 16 to 18, each of the leg portions 510A, 510B, 510C, 510D may comprise a foot portion 511A, 511B, 511C, 511D located distally from the central portion 501 of the base 504. A foot portion 511A of the first leg 510A may comprise a lateral surface at the distal end 512 that extends between the first surface 503 and the second surface 505 of the base 504. The lateral surface may be configured to be generally flat, with the opposing ends of the lateral surface being angled to define chamfers 513A, 513B in the foot portion 511A of the first leg portion 510A. The chamfers 513A, 513B in the foot portion 511A may be configured to engage the coupling feature 412 of the tracker mount 408 of the adapter 402 as described above. While the foot portion 511A of the first leg portion 510A illustrated in FIGS. 16 to 18 includes the lateral surface at the distal end 512 having a pair chamfers 513A, 513B defined at opposed ends of the lateral surface, it is contemplated that the foot portion 511A may be formed with only one end of the lateral surface being angled to form a single chamfer in the foot portion 511A, or formed with no chamfers. Alternatively, it is also contemplated that the lateral surface of the distal end 512 of the foot portion 511A may be formed with three or more angled surfaces to define a plurality of chamfers, fillets, or the like.

A foot portion 511B of the second leg 510B may also comprise a lateral surface 514 that extends between the first surface 503 and the second surface 505 of the base 504. The lateral surface 514 may be configured to be generally flat, with the opposing ends of the lateral surface 514 being angled to define chamfers 515A, 515B in the foot portion 511B of the first leg portion 510B. The chamfers 515A, 515B in the foot portion 511B may be configured to engage the coupling feature 414 of the tracker mount 408 of the adapter 402 described above. Furthermore, similar to the foot portion 511A of the first leg portion 510A, while the foot portion 511B of the second leg portion 510B illustrated in FIGS. 16 to 18 includes the lateral surface 514 having a pair chamfers 515A, 515B defined at opposed ends of the lateral surface 514, it is contemplated that the foot portion 511B may be formed with only one end of the lateral surface 514 being angled to form a single chamfer in the foot portion 511B, or formed with no chamfers. Alternatively, it is also contemplated that the lateral surface 514 of the foot portion 511B may be formed with three or more angled surfaces to define a plurality of chamfers, fillets, or the like.

The shape of each of the foot portions 511A, 511B may be configured to engage the first coupling feature 412 or the second coupling feature 414 of the tracker mount 408 described above. The first coupling feature 412 and/or the second coupling feature 414 may each comprise one or more tabs (e.g., a pair of spaced apart tabs) that are positioned over the base 410 of the tracker mount 408 such that the foot portions 511A, 511B are each configured to be positioned between the one or more tabs of the first coupling feature 412 or of the second coupling feature 414 and the base 410. Furthermore, the first coupling feature 412 and/or the second coupling feature 414 may each comprise one or more angled surfaces 413, 415A, 415B. The one or more angled surfaces 413, 415A, 415B of the first coupling feature 412 and/or second coupling feature 414 may serve to wedge the foot portions 511A, 511B of the first and second portions 510A, 510B between the first coupling feature 412 and/or the second coupling feature 414 and the base 410.

In one example, the first coupling feature 412 and/or second coupling feature 414 may each comprise a pair of angled surfaces 415A, 415B, as illustrated in FIG. 8D, that are spaced apart and configured to engage the fillets or chamfers 513A, 513B, 515A, 515B of the lateral surfaces of the distal ends 512, 514 of the foot portions 511A, 511B of the first and second portions 510A, 510B to provide an anti-rotational force on the base 504 of the tracker 502 to prevent the base 504 of the tracker 502 from rotating relative to the base 410. For instance, using the coordinate system described above where the plane defined by the X-axis and Y-axis is parallel to the top surface of the base 504 of the tracker 502 and the Z-axis is perpendicular to the top surface of the base 504, the first coupling feature 412 and/or the second coupling feature 414 may be configured to prevent movement of the tracker 502 in yaw. The combination of the first coupling feature 412 and the second coupling feature 414 apply both a retention force and an anti-rotational force to the base 504 of the tracker 502 limiting the movement of the tracker 502 in all six degrees of freedom, which can improve both the fitment and the accuracy of the positioning of the tracker 502 relative to the adapter 402.

Figure 23:
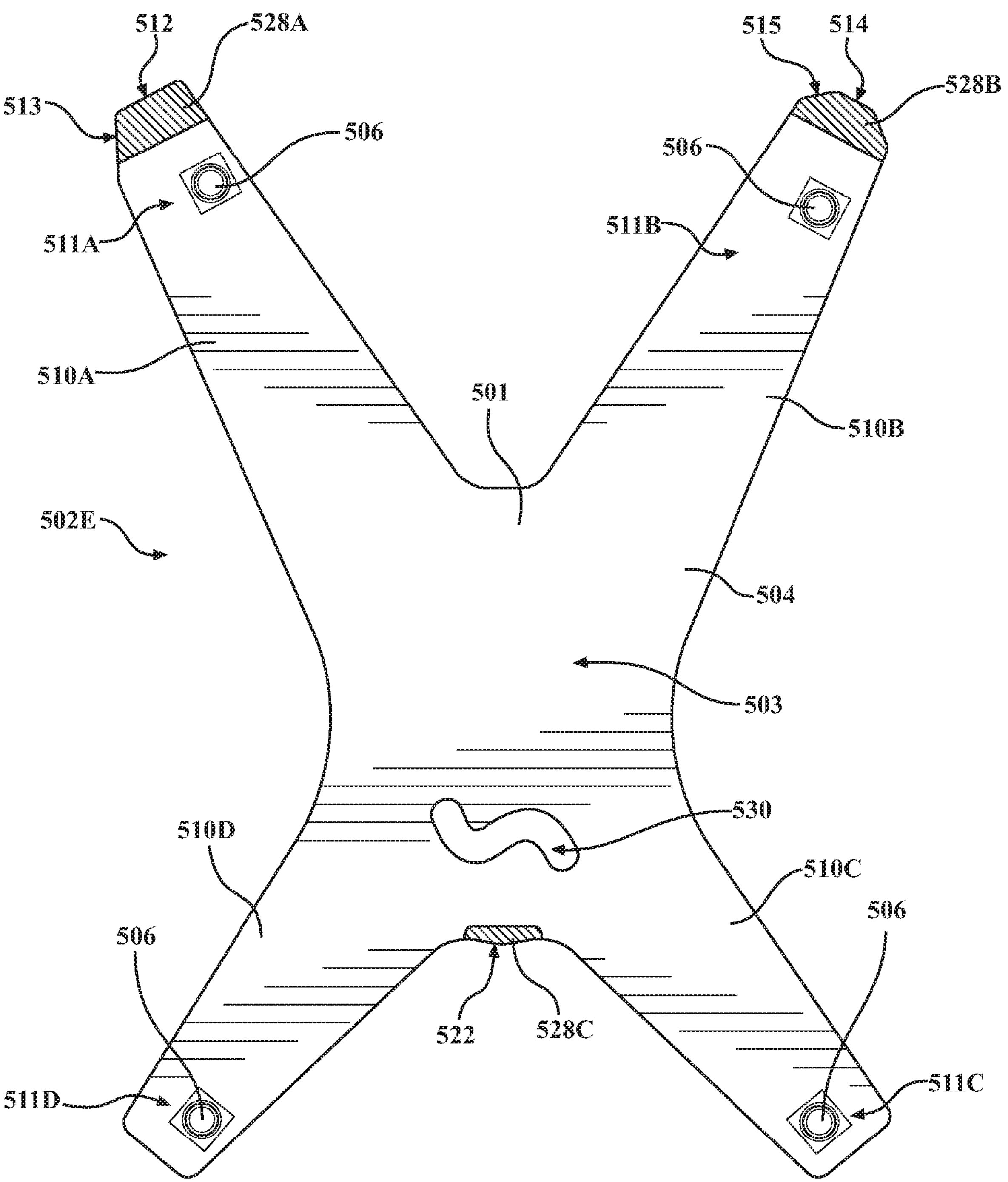
FIG. 23 is a top view of an alternative configuration of a tracker including indicia on at least one of a foot portion of a leg and/or on a protrusion, and an aperture shaped to assist the user in attaching the tracker to the tracker mount.

While the foot portions 511A, 511B of the first and second leg portions 510A, 510B, illustrated in the figures comprise a chamfer, fillet, or similar shape configured to engage the first coupling feature 412 and/or the second coupling feature 414 of the tracker mount 408, and the foot portions 511C, 511D of the third and fourth leg portions 510C, 510D may comprise a similar or more generic shape. However, it is contemplated that any of the foot portions 511A, 5111B, 511C, 511D of the leg portions 510A, 510B, 510C, 510D may be similarly shaped to include one or more fillets, chamfers, or the like that is configured to assist with coupling and/or securing the tracker 502 to the tracker mount 408. It is also contemplated that the tracker 502 may be configured to include any combination of the foot portions 511A, 511B, 511C, 511D of the leg portions 510A, 510B, 510C, 510D shaped to include one or more fillets, chamfers, or the like. For example, as illustrated in FIGS. 16 to 18, the foot portion 511A, 511B of the first and second leg portions 510A, 510B may each comprise a double chamfer 513A, 513B, 515A, 515B. Alternatively, as illustrated in FIG. 23, the foot portion 511A of the first leg portion 510A may comprise a single chamfer 513A and the foot portion 511B of the second leg portion 510B may comprise a double chamfer 515A, 515B. While not illustrated in the figures specifically, other arrangements, shapes, and configurations of the foot portions 511A, 511B, 511C, 511D of the leg portions 510A, 510B, 510C, 510D are contemplated.

It is also contemplated that the tracker 502 may comprise indicia 528 disposed on the first surface 503. The indicia 528 may be disposed on one or more of the foot portions 511A, 511B, 511C, 511D of the leg portions 510A, 510B, 510C, 510D of the tracker 502, and may be configured to assist the user with coupling of the tracker 502 to the tracker mount 408 and/or the adapter 402. For example, as illustrated in FIG. 23, each of the foot portions 511A, 511B of the first and second leg portions 510A, 510B may comprise an indicia 528A, 528B. The indicia 528A, 528B may include a pattern, color, or similar type marking that distinguishes a portion of the first surface 503 that the indicia 528A, 528B is disposed on that is configured to be positioned adjacent the first coupling feature 412 or the second coupling feature 414 from a remaining portion of the first surface 503 of the tracker 502 to assist the user in coupling the tracker 502 to the tracker mount 408. The indicia 528A, 528B may be disposed on the portion of each foot portion 511A, 511B that is configured to be covered by the first coupling feature 412 or the second coupling feature 414 when the tracker 502 is coupled to the tracker mount 408 to provide a visual indicator to the user when the tracker 502 is properly mounted to the tracker mount 408. For example, in operation, each indicia 528A, 528B may be positioned such that when the tracker 502 is properly mounted to the tracker mount 408, the indicia 528 is covered by the first coupling feature 412 or the second coupling feature 414. Alternatively, in the event that the tracker 502 is improperly mounted to the tracker mount 408, each indicia 528A, 528B may not be covered or may only be partially covered by the first coupling feature 412 or the second coupling feature 414. The user being able to still visually see the indicia 528A, 528B may indicate to the user that the tracker 502 is not properly coupled to the tracker mount 408.

The base 504 may also comprise a protrusion 522 extending from the central portion 501 of the tracker 502. The protrusion 522 may extend a distance from the central portion 501 that is less than the distance any one of the leg portions 510A, 510B, 510C, 510D extends from the central portion 501 of the tracker 502. The protrusion 522 may also be positioned between the third and fourth leg portions 510C, 510D, and be configured to selectively engage the locking mechanism 416A, 416B of the tracker mount 408 described above. For example, the protrusion 522 may define a contact portion of the base 504 for the mechanism 416A, 416B to engage on the tracker 502, where the locking mechanism 416A, 416B may be shaped such that the engagement surface 423A, 423B of the locking mechanism 416A, 416B engages the protrusion 522 of the tracker 502 and urges the tracker 502 toward the coupling features 412, 414 of the tracker mount 408 when in the locked position. The locking mechanism 416A, 416B of the tracker mount 408 may further be shaped such that an engagement surface 423A, 423B of the locking mechanism 416A, 416B is disposed over the protrusion 522 of the tracker 502 when in the locked position to supply a downward force on the protrusion 522 to secure the tracker 502 to the tracker mount 408. The rotatable member 419A and/or a pivotable member 419B style locking mechanism 416A, 416B may be utilized to secure the tracker 502 in place to accurately and securely mount the tracker 502 to the tracker mount 408 in a quick and efficient manner without the need for additional tools such as a wrench or screw driver.

As illustrated in FIG. 23, the protrusion 522 may also include an indicia 528C, similar to the indicia 528A, 528B that may be included on the foot portions 511A, 511B, 511C, 511D of the leg portions 510A, 510B, 510C, 510D. The indicia 528C may be disposed on the portion of the protrusion 522 that is covered by the locking mechanism 416A, 416B to assist the user in properly attaching the tracker 502 to the tracker mount 408. For example, in operation, the indicia 528C on the protrusion 522 may be positioned such that when the tracker 502 is properly mounted to the tracker mount 408, the indicia 528C is covered by the locking mechanism 416A, 416B. Alternatively, in the event that the tracker 502 is improperly mounted to the tracker mount 408, the indicia 528C may not be covered or may only be partially covered by the locking mechanism 416A, 416B. The user being able to still visually see the indicia 528C on the protrusion 522 may indicate to the user that the tracker 502 is not properly coupled to the tracker mount 408.

The base 504, such as in the form of a board, may be configured to be directly seated in the tracker mount 408. To this end, the base 504 may not be contained within a housing or rigid covering, and may be shaped to conform to the recess defined by the tracker mount 408 for receiving the tracker 502. For instance, assuming the tracker mount 408 defines a star-shaped recess for receiving the tracker 502 that includes a central portion and a plurality of leg recesses that extend from the central portion, the base 504 may have a shape conforming to the star-shaped recess (e.g., a central portion 501 and leg portions 510 extending from the central portion 501 that correspond to the leg recesses of the star-shaped recess). The base 504 may also include a perimeter surface 532 extending between the first and second faces 503, 505 and circumferentially extending around the base 504 for being gripped by a user to mount the tracker 502 to the tracker mount 408.

As described above, the tracker 502 may comprise one or more markers 506. The markers 506 may be active light sources (e.g., LEDs) driven by a control circuit 519 of the tracker 502 or passive reflective type markers consistent with the description above. The markers 506 may be disposed on the base 504 of the tracker 502. More particularly, as illustrated in FIG. 17A, the markers 506 may be disposed on the distally directed surface 503 of the base 504. For instance, the markers 506 may be disposed on the foot portion 511 of each of the leg portions 510 of the base 504. The markers 506 may be arranged on the base 504 in a unique pattern and/or arrangement that when optically perceived by the navigation system 102, is recognizable and/or identifiable by the navigation system 102 to distinguish between trackers 502A, 502B, 502C, 502D.

Figure 21:
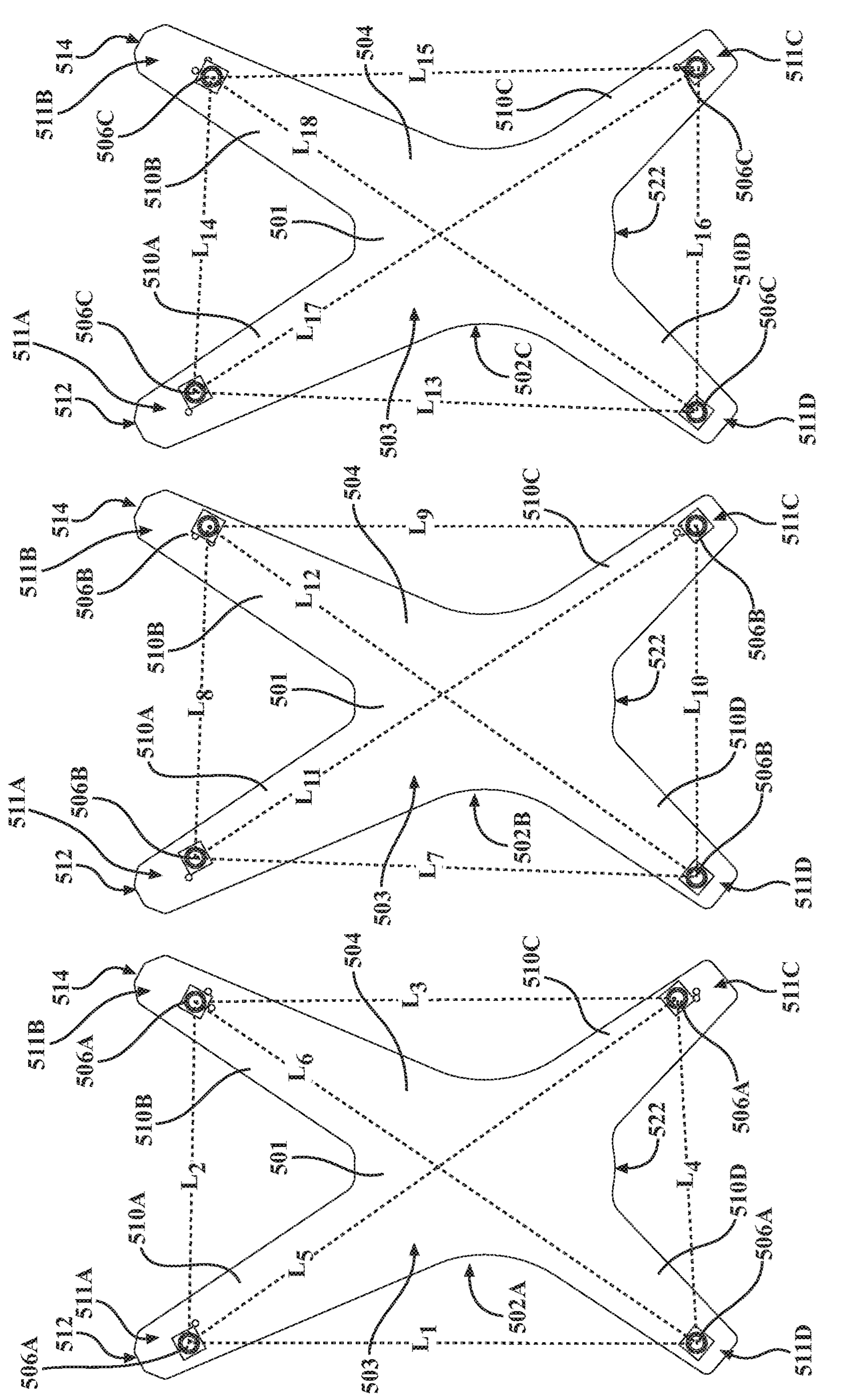
FIG. 21 is a top view of a set of trackers, each of the trackers including a distinct marker pattern from the other trackers in the set.

FIG. 17B illustrates an exemplary base 504 including a plurality of marker locations $P_A$, $P_B$, $P_C$ on the leg portions 510 for creating unique patterns and/or arrangements of markers 506A, 506B, 506C (see FIGS. 15 and 21). For example, a first tracker 502A (see FIGS. 15, 17B, and 21) may include a first arrangement of markers 506A where each of the markers 506A are positioned at the marker locations $P_A$ about the base 504. A second tracker 502B (see FIGS. 15, 17B, and 21) may include a second arrangement of markers 506B where each of the markers 506B are positioned at the marker locations $P_B$. Further yet, a third tracker 502C (see FIGS. 15, 17B, and 21) may include a third arrangement of markers 506C where each of the markers 506*c* are positioned at the marker locations $P_C$. Note, it is further contemplated that all of the variations of the markers 506A, 506B, 506C may include at least one common reference marker location that is positioned at the same location on the base 504 of each of the trackers 502A, 502B, 502C. For example, all variations of the markers 506A, 506B, 506C may include a marker 506 positioned at marker location $P_{A, B, C}$, of the fourth leg portion 510D. The marker 506 disposed on each the remaining three leg portions 510 may then be positioned at different marker locations to create the unique pattern for each of the trackers 502A, 502B, 502C.

Figure 19:
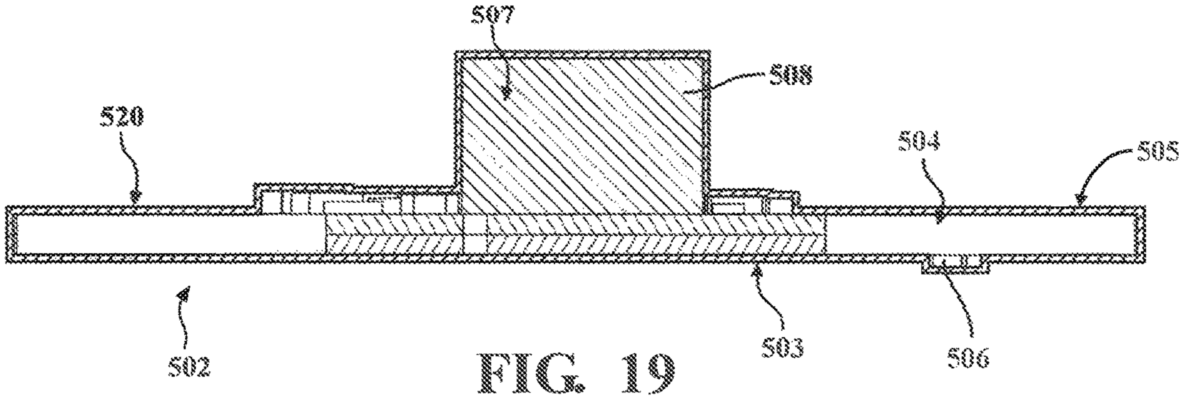
FIG. 19 is a sectional view of the tracker of FIG. 16 including a coating applied to exterior surfaces of the base and related components of the tracker.

In instances in which the markers 506 are active light sources, the tracker 502 may also include a battery mount 507 and a control circuit 519 coupled to the base 504 of the tracker 502. The battery mount 507 may be configured for connecting and/or securing a battery 508 to the base 504 for the purpose of powering the electrical components of the tracker, such as the markers 506. For example, as illustrated in FIGS. 18 and 19, the battery mount 507 may be disposed on the second surface 505 of the base 504, which may also be referred to as the bottom surface or underside of the base 504 of the tracker 502, such that the battery 508 when secured to the battery mount 507 extends outward from the second surface 505. This arrangement may prevent the battery 508 from interfering with or intercepting the light signals emitted from the markers 506 by virtue of the markers 506 being disposed on the opposed first surface 503. While the battery mount 507 is illustrated in the Figures as being disposed on the second surface 505 of the base 504, it is also contemplated that the battery mount 507 could be disposed on the first surface 503 of the base 504, such as if the navigation system 102 is positioned to observe the tracker 502 from angles not affected by the battery 508.

The battery mount 507 may comprise two or more terminals (also referred to as "battery contacts") 509A, 509B for engaging a battery 508 when the battery 508 is seated in the battery mount 507. In particular, the battery contacts 509 may be configured to communicate electrical energy between the battery 508 disposed in the battery mount 507 and each of the markers 506. Some exemplary implementations of LED tracking markers 506 are shown and described in U.S. Patent Application Publ. No. 2019/0321108 and International Application No. PCT/IB2020/060187, both of which are hereby incorporated by reference. The control circuit 519, described in more detail below, may be configured to regulate the brightness of the markers 506 by regulating the current applied to the markers 506 from the battery 508.

In some instances, the battery 508 may be permanently affixed within the battery mount 507, so as to provide a tracker 502 configured for limited use (e.g., single use). In other words, the battery 508 may be configured with a capacitor for powering the markers 56 for the duration or a portion of a surgical procedure, but not substantially more. In alternative examples, the battery 508 may be removable from the battery mount 507 and replaced so as to enable extended use of the tracker 502, such as in multiple surgical procedures.

In either configuration, the tracker 502 may comprise a switch configured to regulate the flow of electrical energy from the battery 508 to each of the markers 506, such as by preventing the flow of such electrical energy until the switch is activated. This may allow for preservation of the battery 508 and prevent unnecessary draining of the battery 508 when the tracker 502 is not in-use. In some instances, such as when the tracker 502 is configured for multi-use, the switch may comprise a multi-use switch 518, such as an electrical switch or breaker, that may be toggled between an ON position where the flow of electricity from the battery 508 to each of the markers 506 is enabled, and an OFF position in which the flow of electricity from the battery 508 to each of the markers 506 is prevented.

Alternatively, such as when the tracker 502 is configured for single use, the switch may be a single use switch 526. For instance, the single use switch 526 may be a dielectric or nonconducting film disposed between the battery 508 and at least one of the battery terminals 509A, 509B to break the circuit between the battery 508 and each of the markers 506. As examples, the single use switch 526 may be configured as a film or strip comprising a Mica, ceramic, cellulose, porcelain, Mylar, Teflon or similar non-conductive material that is removably disposed between the battery 508 and at least one of the battery terminals 509A, 509B. In operation, when the user is ready to use the tracker 502, the user can remove the switch 526 from between the battery 508 and at least one of the battery terminals 509A, 509B, allowing the circuit between the battery 508 and each of the markers 506 to be completed and electrical energy to flow to the markers 506.

In some examples, the tracker 502 may further comprise circuitry for a status indicator 524 electrically coupled to at least one of the markers 506, the battery 508, and the control circuit 519. In one implementation, the status indicator 524 may comprise an LED that emits visible (i.e. non-infrared) light so that a surgeon can easily verify that the tracker 502 has been activated and is functioning. The status indicator 524 may be configured to provide additional diagnostic or operational information to the surgeon, such as remaining battery capacity. For example, the status indicator 524 may flash or blink when the battery 508 voltage corresponds to a first level, and when the battery 508 voltage corresponds to a second level the status indicator 524 may turn off. The status indicator 524 may further be implemented with more than one LED, or an LED capable of illuminating with more than one color. If more than one LED is used the voltage level of the battery 508 may correspond to the number of LEDs that are concurrently illuminated. If multi-color LEDs are used the color emitted from the LED may correspond to the voltage level of the battery 508.

As previously mentioned, in some instances, the base 504 of the tracker 502 may be a printed circuit board (PCB). In other words, the base 504 may take the form of a PCB shaped to correspond to the recess defined by the tracker mount 408. For instance, assuming the tracker mount 408 defines a star-shaped recess for receiving the tracker 502, the base 504 may be a PCB having a shape conforming to the star-shaped recess (e.g., including leg portions 510 corresponding to the leg recesses of the star-shaped recess). The PCB may include traces connecting the markers 506, control circuit 519, and battery 508.

More particularly, the base 504 may be a double-layered PCB with the markers 506 mounted to the first surface 503 of the PCB, and the battery 508 and control circuit 519 mounted to the second surface 505, as described above. The first surface 503 of the PCB may include first traces 516 (FIG. 17A) connecting the markers 506 to each other, such as in parallel or series as described in more detail below, and the second surface 505 of the PCB may include second traces 517 (FIG. 18B) for connecting the control circuit 519 to the battery contacts 509 and to each the markers 506, such as with the latter connection being facilitated by plated through holes 534 formed in the PCB.

Referring to FIG. 19, some embodiments of the tracker 502 may be configured where the base 504 (e.g., PCB) comprises outward facing exterior surfaces 503, 505 that may be exposed and susceptible to contact with debris or fluids. A short circuit from such contact may result in damage to the components coupled to the base 504 (e.g., PCB) such as the markers 506, battery 508, or control circuit 519, which may cause undesirable operation of the tracker 502. To help alleviate this issue, the base 504 (e.g., PCB) forming each of the tracker arrays 502 may be protected by the application of a conformal coating 520, which creates a barrier on the base 504 (e.g., PCB) preventing the ingress of debris and fluids. Exemplary conformal coatings 520 may comprise a parylene film applied to assembled PCBs. Alternatively, the markers 506, and/or battery 508, and/or status indicator 524, and/or ICs disposed on the base 504 (e.g., PCB) may be masked off before applying the conformal coating 520 such that these items are not covered or not fully covered with the conformal coating 520 applied to the remaining portions of the base 504.

Figure 20:
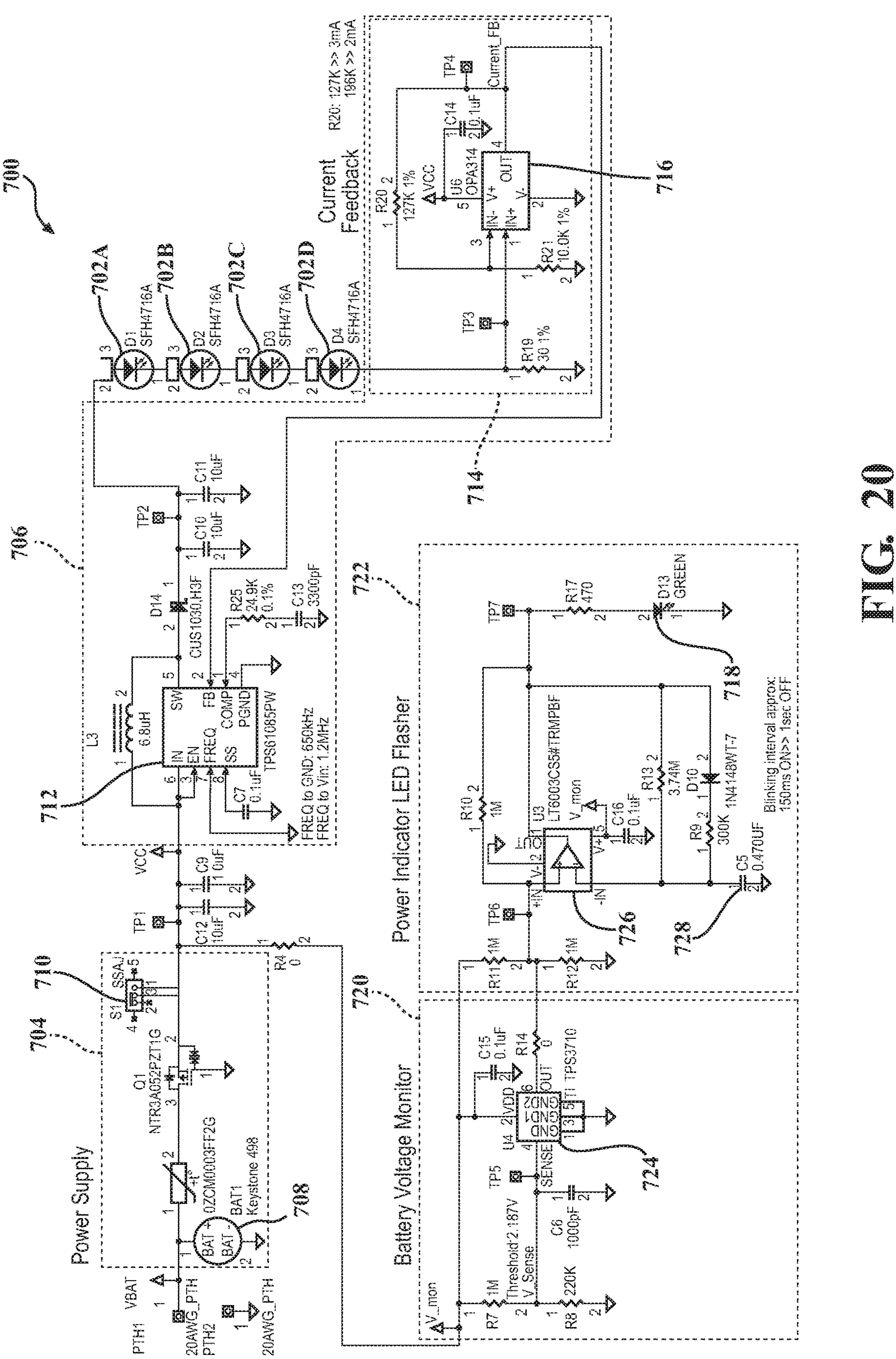
FIG. 20 is a schematic diagram outlining an exemplary electrical circuit of the tracker of FIGS. 16 to 19.

FIG. 20 illustrates a circuit 700 that may be incorporated into the tracker array 502. The circuit 700 may include a plurality light sources 702, a power supply 704, and a control circuit 706 coupled to the power supply 704 and the light sources 702. The control circuit 706 may be configured to control the intensity of the light emitted from the light sources 702, such as by regulating the current supplied to the light sources 702 from the power supply 704. In this way, the control circuit 706 may prevent the light sources 702 from emitting light that saturates the optical sensors 150 of the navigation system 102, which in turn may cause imprecise tracking by the navigation system 102.

The light sources 702 may correspond to the markers 506 of the tracker array 502 described above, and may thus be arranged in a predefined pattern on the tracker array 502 for being recognized by the navigation system 102 to track a surgical object or instrument associated with the tracker array 502. Each light source 702 may be a light emitting diodes (LED), or more particularly, an infrared LED (IR-LED), that is configured to emit light at a wavelength corresponding to the range of wavelengths detectable by the camera unit 148. For instance, the camera unit 148 may be optimized to detect light at one or more wavelengths between 840 nm and 860 nm, such as above about 850 nm, and each light source 702 may be configured to emit light with a wavelength between 800 nm and 900 nm, or more preferably with a wavelength between 850 nm and 860 nm. Each light source 702 may have a peak brightness at 859 nm.

As shown in the illustrated example, the light sources 702 may be connected in series so that, during operation of the circuit 700, the current passing through each light source 702 is the same. Correspondingly, the light intensity emitted from each light source 702 may be substantially the same. Under this configuration, the control circuit 706 may regulate the intensity of all the light sources 702 based on a current measurement taken at a single point in the circuit 700, such as by adjusting the voltage applied across the light sources 702 based on the measured current.

In alternative configurations, the light sources 702 may be connected in parallel, with each light source 702 being connected in series with a resistor that limits the current passing through the corresponding light source 702. The resistors may be selected so that the current passing through each light source 702 is substantially the same, and correspondingly, the light intensity emitted from each light source 702 is substantially the same. In some examples, the resistors may be adjustable to enable fine tuning of the current passing through each light source 702. In the parallel configuration, if one of the light sources 702 fails, operation of the other light sources 702 may remain uninterrupted.

The power supply 704 may include a battery 708, which may correspond to the battery 508 described above. The battery 708 may be permanently mounted to the tracker array 502 such that the tracker array 502 is configured for limited use (e.g., single use). More specifically, the battery 708 may be configured with a capacity sufficient to power the tracker array 502 for the duration of or a significant portion of many surgical procedures. The battery 708 may also have a weight that is low enough so as to not cause the tracker array 502 to overcome the biasing member 422 when coupled to the tracker mount 408 without applied user force. In one example, the battery 708 may be a CR1/3N 3V battery, which may have such a weight and is capable of operating the tracker array 502 for about ten hours.

The circuit 700 may also include a user switch for controlling the flow of energy from the battery 708 to the control circuit 706 and the light sources 702. In some examples, the user switch may be a multi-use switch 710, which may correspond to the multi-use switch 518 described above, that enables a user to repeatably turn on and off the supply of electrical energy from the battery 708 to the control circuit 706 and light sources 702. Alternatively, such as when the tracker array 502 is configured for single use, the user switch may be a single-use switch, such as the single-use switch 526 described above, in which an initial interaction with the single-use switch by a user enables electrical energy to flow from the battery 708 to the control circuit 706 and light sources 702, and also disables the switch such that a user is unable to thereafter interact with the switch to prevent the flow of energy.

The control circuit 706 may form at least part of the control circuit 519 described above, and may be configured to receive the electrical energy from the power supply 704, and to utilize such energy to regulate the intensity of the light emitted from the light sources 702 from the electrical energy. More particularly, the control circuit 706 may be configured to limit the intensity of the light emitted from each of the light sources 702 to prevent saturation of the optical sensors 150 of the camera unit 158. For instance, the control circuit 706 may be configured to limit the intensity of the light sources 702 to not exceed 40 microwatts per steradian (μW/sr), preferably 20 μW/sr, and more preferably 10 μW/sr.

The control circuit 706 may be configured to limit the intensity of the light sources 702 by limiting the current through each of the light sources 702. For instance, the control circuit 706 may be configured to limit the current through each of the light sources 702 to not exceed 20 milliamps, preferably 15 milliamps, more preferably 10 milliamps, and further more preferably 4 milliamps. In some instances, the control circuit 706 may be configured to maintain the current through each of the light sources 702 at a level less than 4 milliamps and greater than 1 milliamps, such as at approximately 2 milliamps or 3 milliamps.

In one example, the control circuit 706 may include a controller 712 and a current feedback circuit 714 coupled to the controller 712. The controller 712, which may include a step-up DC-DC converter, may be configured to generate a drive signal applied to the light sources 702 that causes the light sources 702 to emit light signals, such as continuously or quasi-continuously. Thereafter, the current feedback circuit 714 may be configured to compare the current through the light sources 702 to a target current level that corresponds to one or more of the above limits (e.g., less than 20 milliamps, such as 2 milliamps or 3 milliamps), and generate a feedback signal based on the comparison. The feedback signal may correspond to the error between the applied current and the target current level.

For instance, as shown in the illustrated example, the current feedback circuit 714 may include a comparator 716 that is connected to and receives the voltage at the cathode of the last light source 702D in the series, and generates a feedback signal based thereon that represents the difference between the current through the light sources 702 and the target current level. The target current legal may be set, such as to 2 milliamps or 3 milliamps, by adjusting the feedback resistor of the current feedback circuit 714. The current feedback circuit 714 may then supply the feedback signal to the controller 712, which may be configured to responsively adjust the voltage applied to the light sources 702 to reduce the difference.

The circuit 700 may also include a status indicator 718, such as an LED, coupled to the power supply 704. The status indicator 718 may correspond to the status indicator 524 described above, and may be configured to emit visible light indicative of the operating condition of the tracker array 502, such as the remaining capacity of the battery 708. For instance, the status indicator 718 may be configured to emit blinking visible light when the capacity of the battery 708 is greater than a threshold level, and to cease emitting any visible light when the capacity of the battery 708 is less than the threshold level and/or no longer sufficient to operate the tracker array 502.

To this end, the circuit 700 may include a battery voltage monitor circuit 720 and a power indicator LED flasher circuit 722. The battery voltage monitor circuit 720 may include a voltage comparator 724 configured to sense and compare the voltage of the battery 708 to a threshold level, such as 2.187 volts, and to output a voltage sense signal representative of the comparison. For instance, responsive to the comparison indicating that the voltage of the battery 708 is greater than or equal to the threshold level, the voltage comparator 724 may be configured to output a high voltage sense signal, and responsive to the comparison indicating that the voltage of the battery 708 is less than the threshold level, the voltage comparator 724 may be configured to output a low voltage sense signal.

The battery voltage monitor circuit 720 may be configured to supply the voltage sense signal to the power indicator LED flasher circuit 722, which may include a comparator 726 for driving the status indicator 718. One input of the comparator 726 may be coupled to the supplied voltage sense signal, and another input of the comparator 726 may be coupled to a capacitor 728. The output of the comparator of the 726 may be coupled to both the status indicator 718 and the capacitor 728. When the voltage sense signal is high, the comparator 726 may initially output a signal that causes the status indicator 718 to emit light and simultaneously charges the capacitor 728. Upon the voltage across the capacitor 728 exceeding the voltage at the other input of the comparator 726, the output of the comparator 726 may be driven low, and correspondingly, the status indicator 718 may cease emitting visible light. Subsequently, the capacitor 728 may begin to discharge, causing the comparator 726 to again be driven to high and cause the status indicator 718 to emit visible light. In this way, the status indicator 718 may emit flashing visible light, such as at a rate of 150 milliseconds ON followed by 1 second OFF.

Conversely, when the voltage sense signal is low, the output of the comparator 726 may be driven low, and the status indicator 718 may correspondingly cease emitting any visible light. Along with the control circuit 706, the battery voltage monitor circuit 720 and power indicator LED flasher circuit 722 may form at least part of the control circuit 519 of the tracker 502 described above.

Referring to FIGS. 15 and 21, a plurality of end effectors 202, 202B, 202C, 302 each having their own adapter 402 and trackers 502A, 502B, 502C, 502D. Each of the trackers 502A, 502B, 502C, 502D may have a unique pattern of markers 506A, 506B, 506C, 506D that is identifiable by the navigation system 102. The navigation system 102 may be configured to assign a given pattern or arrangement of markers 506A, 506B, 506C, 506D on a tracker 502A, 502B, 502C to a particular end effector 202, 202B, 202C, 302 either by user section/input into the navigation system 102 or by using the optical sensor 150 of the camera unit 148, i.e. machine vision, to identify the end effector 202, 202B, 202C, 302 that the pattern of markers 506A, 506B, 506C, 506D is associated with. Once a particular pattern of markers 506A, 506B, 506C, 506D is assigned to one of the end effectors 202, 202B, 202C, 302, the navigation system 102 will be able to identify which of the end effectors 202, 202B, 202C, 302 is currently in use, and accurately track the pose of the given end effector 202, 202B, 202C, 302 as it is manipulated by the user.

This may be accomplished by varying the position of markers 506 on the trackers 502A, 502B, 502C, 502D such that the segment lengths L1 to L18 connecting any two markers 506 are distinguishable from one another. This may be accomplished by positioning the various markers 506 for a specific tracker 502A, 502B, 502C, 502D in different marker locations (e.g., marker locations $P_A$, $P_B$, $P_C$) associated with each of the leg portions 510A, 510B, 510C, 510D. For instance, as illustrated in FIG. 21, by positioning the markers 506 of a given tracker 502A, 502B, 502C in a different set of marker locations $P_A$, $P_B$, $P_C$ on the corresponding leg portions 510A, 510B, 510C, 510D, the segment lengths connecting the markers 506 will vary such that any three markers 506 on a given tracker 502A, 502B, 502C with define a uniquely shaped triangle that differs from the triangle formed by the same three markers 506 on one of the other trackers 502A, 502B, 502C.

As an example, the arrangement of markers 506A on the first tracker 502A includes segment lengths L1, L2, and L6 defining a triangle using the markers 506A disposed on the first, second, and fourth leg portions 510A, 510B, 510D of the first tracker 502A. The arrangement of markers 506B on the second tracker 502B includes a segment lengths L7, L8, and L12 defining a triangle using the markers 506B disposed on the first, second, and fourth leg portions 510A, 510B, 510D of the second tracker 502B. The arrangement of markers 506C on the third tracker 502C includes a segment lengths L13, L14, and L18 defining a triangle using the markers 506C disposed on the first, second, and fourth leg portions 510A, 510B, 510D of the third tracker 502C. The triangles formed by these segment lengths connecting the various markers 506 are each unique based on the combination of segment lengths L1, L2, L6 of the first tacker 502A compared to the combination of segment lengths L7, L8, L12 of the second tacker 502B and compared to segment lengths L13, L14, and L18 of the third tracker 502C.

The navigation system 102 may be configured observe the arrangement of markers 506A, 506B, 506C, 506D and use the specific patterns to identify the specific tracker 502A, 502B, 502C, 502D and by extension the end effectors 202, 202B, 202C, 302 associated with the tracker 502A, 502B, 502C, 502D. While the navigation system 102 may be configured to distinguish between trackers 502A, 502B, 502C, 502D based on any arrangement of three markers 506 on the tracker 502A, 502B, 502C, 502D, the addition of a fourth marker 506 being disposed on the base 504 of the tracker 502A, 502B, 502, 502D may improve accuracy. Specifically, the improved accuracy may allow the navigation system 102 to distinguish between two or more similar trackers 502A, 502B, 502C, 502D in close proximity to one another and when observed using the same optical sensor 150 of the camera unit 148 of the navigation system 102. In some exemplary configurations of the navigation system 102, for trackers 502 with four markers 506 arranged on the bases 504 of the trackers 502, the navigation system 102 may be configured to detect and distinguish between segment lengths L1 to L18 between any two of the markers 506 that differ from one another by greater than or equal to 2.0 millimeters (mm). However, the navigation system 102 may be adjusted such that the threshold of 2.0 mm to detect and/or distinguish between any two segment lengths may be adjusted and/or calibrated.

Figure 22A:
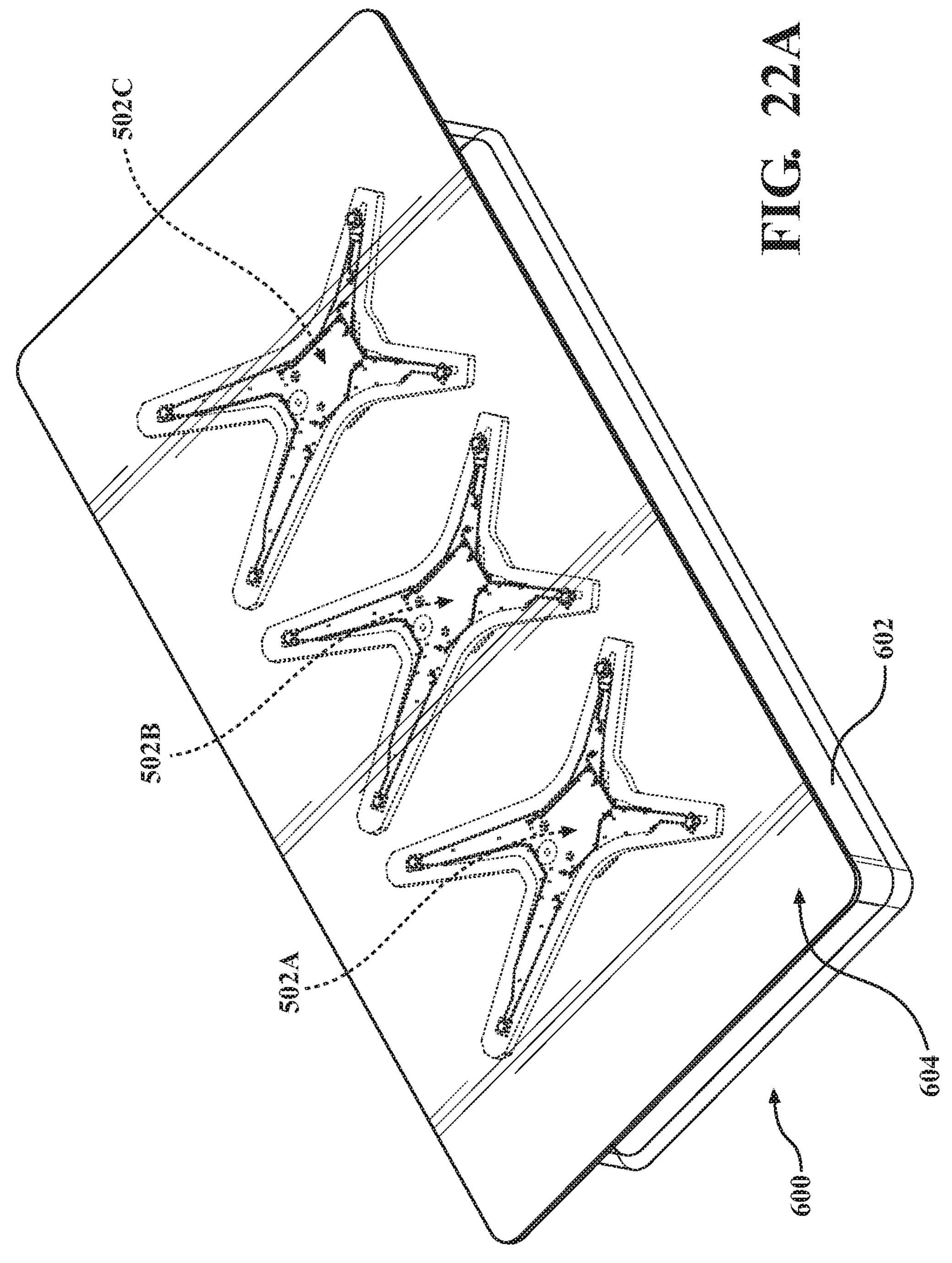
FIG. 22A is a perspective view of an exemplary configuration of a packaging system for storing a set of trackers in a sterile environment prior to use, illustrating the packaging system with the cover sealing to the container to maintain the sterile environment within the container.
Figure 22B:
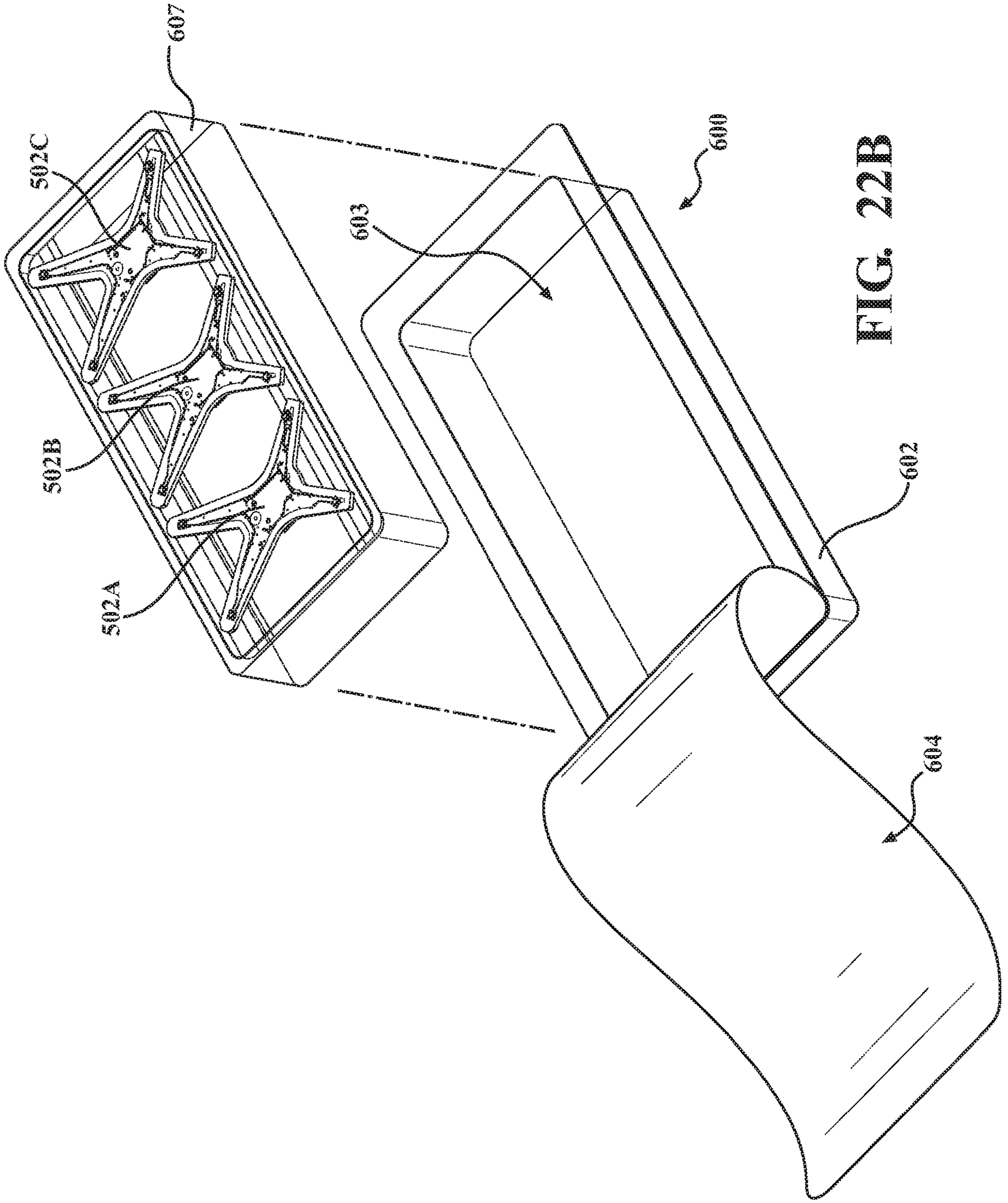
FIG. 22B is a perspective view of the packaging system of FIG. 22A, illustrating the packaging system with the cover removed from the container allowing the user to access the trackers stored within.

Referring to FIGS. 22A and 22B, an exemplary configuration of a packaging system 600 for maintaining sterility of one or more trackers 502A, 502B, 502C is illustrated. The packaging system 600 may comprise a container 602 defining a cavity 603, and a cover 604 configured to removably seal the cavity 603 defined by the container 602. The cover 604 may be configured to cover the cavity 603 defined by the container 602 to maintain a sterile environment within the cavity until the cover 604 is removed. One or more of the trackers 502A, 502B, 502C may be stored within the cavity 603 defined by the container 602 until the cover 604 is removed to access the trackers 502A, 502B, 502C. The packaging system 600 may further comprise a tray 607 sized to fit within the cavity 603 defined by the container 602 and configured to support and/or organize the one or more trackers 502A, 502B, 502C stored within the container 602. The tray 607 may further be shaped and/or configured to store two more trackers 502A, 502B, 502C, each of the trackers 502A, 502B, 502C having a unique pattern or markers 506A, 506B, 506C, such that each tracker 502A, 502B, 502C is distinguishable from the other trackers 502A, 502B, 502C included in the packaging system 600. This provides the advantage of packaging multiple distinguishable trackers 502A, 502B, 502C in a single container 602 for use during a surgical procedure involving multiple surgical instruments 106 and/or end effectors 202, 302 that all require tracking by the navigation system 102.

Referring to FIG. 23, an alternative configuration of a tracker 502E is provided. The tracker 502E includes many of the same features as the trackers 502 described above, as indicated by the common reference numbers. However, the tracker 502E illustrated in FIG. 23 shows an exemplary representation of the indicia 528A, 528B, 528C on the foot portions 511A, 511B and/or protrusion 522 of the base 504 for assisting the user with properly aligning and/or installing the tracker 502 on the tracker mount 408 and/or adapter 402.

The tracker 502E may also include an aperture 530 defined in the base 504 of the tracker 502E. The aperture 530 may be shaped to receive a pin or protrusion (not shown) of the tracker mount 408. The combination of the aperture 530 of the tracker 502E and the pin of the tracker mount 408 may serve to assist the user with aligning the tracker 502E within the tracker mount 408. This may improve the tolerance for positioning the tracker 502E within the tracker mount 408, further improving the accuracy of tracking the pose of the surgical instrument 106. The aperture 530 may also be shaped to assist the user with inserting the tracker 502E into the tracker mount 408 in the correct orientation. For example, the aperture 530 may be shaped so that the tracker 502E may only be inserted within the tracker mount 408 one way, with the first surface 503 facing up and the second surface 505 of the base 504 facing down, toward the tracker mount 408. If the user tried to insert the tracker 502E within the tracker mount 408 in the inverse orientation, the aperture 530 would not properly align with the pin of the tracker mount 408 and prevent the user from securing the tracker 502E to the tracker mount 408 using the locking mechanism 416.

Method of Attaching:

The method of attaching a tracker 502 to a tracker mount 408 for tracking the position of a surgical instrument 106 with a surgical navigation system 102 comprises providing a tracker 502 comprising a central body portion 501 and a plurality of legs 510 extending from the central body portion 501, each of the plurality of legs 510 comprising a foot portion 511 located spaced apart from the central body portion 501, and a plurality of light source type markers 506 coupled to the plurality of legs 510. The method may further comprise inserting the foot portions 511 of two of the plurality of legs 510 within respective recesses defined by coupling features 412, 414 of the tracker mount 408 of the surgical instrument 106, and manipulating a locking mechanism 416 of the tracker mount 408 to removably secure the tracker 502 to the tracker mount 408 after the foot portions 511 are inserted within the respective recesses of the tracker mount 408.

The method may further comprise removing insulator type single use switch 526 from between a battery terminal 509 of a battery mount 507 on the tracker 502 and a battery 508 disposed in the battery mount 507 to allow electrical connection between the battery 508 and the battery terminal 509.

Those having ordinary skill in the art will appreciate that aspects of the configurations described and illustrated herein can be interchanged or otherwise combined.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

Certain implementations may be described with reference to the following exemplary clauses:

1. A tracker assembly for tracking a surgical instrument with a surgical navigation system, the tracker assembly comprising:
   a tracking array comprising:
      an array base;
      a first leg extending distally from the array base; and
      a first marker identifiable by the surgical navigation system coupled to the first leg proximate a distal end of the first leg; and
   a tracking array mount for securing the tracking array to a surgical instrument, the tracking array mount comprising:
      a base defining a mounting surface; and
      a first tab disposed above the mounting surface a distance greater than a thickness of the array base, the first tab comprising an angled surface configured to urge the array base toward the mounting surface when the distal end of the first leg of the array base is disposed between the first tab and the mounting surface.
2. The tracker assembly of clause 1, further comprising:
   a second leg extending distally from the array base; and
   a second marker identifiable by the surgical navigation system coupled to the second leg proximate a distal end of the second leg.
3. The tracker assembly of clause 2, wherein the tracking array mount further comprises a second tab disposed above the mounting surface, the second tab comprising a pair of angled surfaces configured to provide two contact points on opposing edges of the second leg of the tracking array to inhibit rotation of the tracking array relative to the mounting surface.

4. The tracker assembly of clause 3, wherein the tracking array mount further comprises a biasing member configured to urge the tracking array toward the first tab and the second tab to removably couple the tracking array to the tracking array mount, and wherein, optionally, the biasing member is further configured to urge the tracking array toward the mounting surface.

5. A tracking array mount for securing a tracking array to a surgical tool, the tracking array mount comprising:

a base defining a mounting surface;

a first tab disposed above the mounting surface, the first tab comprising an angled surface configured to urge the tracking array toward the mounting surface;

a second tab disposed above the mounting surface the second tab comprising a pair of angled surfaces configured to provide two contacts points on opposing edges of the tracking array to inhibit rotation of the tracking array relative to the mounting surface; and a biasing member configured to urge the tracking array toward the first tab and the second tab to removably couple the tracking array to the tracking array mount.

6. The tracking array mount of clause 5, further comprising a wall disposed at a perimeter of the base, the wall extending from the mounting surface and defining a recess, and wherein, optionally, the first tab is oriented to project from the wall and be at least partially disposed above the mounting surface, and the wall extends a distance above the mounting surface that is greater than a thickness of the tracking array such that at least a portion of the tracking array is disposed between the mounting surface and the first tab when the tracking array is disposed in the recess defined by the wall to couple the tracking array to the tracking array mount.

7. The tracking array mount of clause 6, wherein the wall extends a distance above the mounting surface that is greater than a thickness of the tracking array such that the wall protects the tracking array and/or a marker disposed on the tracking array from an impact.

8. The tracking array mount of clause 6 or 7, wherein the recess is substantially similar to the shape of the tracking array.

9. The tracking array mount of any one of clauses 6-8, further comprising a first tracking array comprising a plurality of tracking elements, wherein the recess defines a plurality of leg recesses, and wherein the first tracking array comprises a plurality of legs, the plurality of leg recesses sized to accommodate the plurality of legs, and wherein, optionally, the first tab is located within one of the plurality of leg recesses.

10. The tracking array mount of clause 9, wherein the second tab is located within a different one of the plurality of leg recesses from the first tab.

11. The tracking array mount of clause 9 or 10, wherein the plurality of legs of the first tracking array include a first leg and a second leg, the first leg including a first indentation at distal portion of the first leg and the second leg including a second indentation at a distal portion of the second leg, wherein the first indentation is shaped differently from the second indentation, and wherein, optionally, the first indentation is V-shaped, and the second indentation is concave and arc-shaped.

12. The tracking array mount of any one of clauses 9-11, further comprising a second tracking array comprising a plurality of tracking elements, a spatial orientation of the plurality of tracking elements of the second tracking array being different than a spatial orientation of the plurality of tracking elements of the first tracking array, wherein, optionally, the first tracking array includes a first visual indicia and the second tracking array includes a second visual indicia, the first visual indicia being distinguishable by a person from the second visual indicia.

13. The tracking array mount of any one of clauses 9-12, wherein the first tracking array comprises: a circuit board having a planar configuration; an arrangement of at least three IR-LEDs coupled to the circuit board and disposed in a common plane, the distance between any two IR-LEDs being unique; and a battery in electrical communication with the at least three IR-LEDs, wherein the tracking array does not comprise a communication interface and does not comprise a power cord, and wherein, optionally, the arrangement of at least three IR-LEDs is configured for continuous or quasi-continuous operation.

14. The tracking array mount of clause 13, wherein the tracking array further comprises an electrical circuit configured to limit a current for the at least three IR-LED to not exceed 15 mA.

15. A disposable tracker for coupling to the tracking array mount of any one of the preceding clauses, the disposable tracker comprising:

a circuit board having a planar configuration; an arrangement of at least three IR-LEDs coupled to the circuit board and disposed in a common plane, the distance between any two IR-LEDs is unique;

an electrical circuit configured to limit a current for the at least three IR-LED to not exceed 15 mA; and a battery in electrical communication with the at least three IR-LEDs, wherein the disposable tracker does not comprise a communication interface and does not comprise a power cord, and wherein, optionally, the electrical circuit comprises at least one resistor configured to limit the current for at least one of the at least three IR-LEDs.

16. The disposable tracker of clause 15, wherein the current for the at least one of the at least three IR-LEDs is limited by an internal electrical resistance of the at least one of the at least three IR-LEDs and an electrical resistance of the at least one resistor electrically connected in series to the at least one of the at least three IR-LEDs.

17. The disposable tracker of clause 15 or 16, wherein the electrical circuit is configured to limit a radiant intensity of at least one of the at least three IR-LEDs to not exceed 40 microwatts per steradian (μW/sr).

18. The disposable tracker of any one of clauses 15-17, wherein a distance between two of the at least three IR-LEDs is less than 70 mm.

19. The disposable tracker of any one of clauses 15-18, wherein the electrical circuit is configured to operate the at least three IR-LEDs simultaneously.

20. The disposable tracker of any one of clauses 15-19, wherein a mass of the disposable tracker does not exceed 40 g.

21. The disposable tracker of any one of clauses 15-20, further comprising a battery receptacle configured to engage the battery, and wherein the battery is further defined as a coin-cell battery.

22. The disposable tracker of any one of clauses 15-21, further comprising a single-use switch in electrical communication with the at least three IR-LEDs.
23. A surgical navigation system comprising the tracker of any one of clauses 15-22 and a camera capable of detecting light emitted from the at least three IR-LEDs and of generating a camera signal indicative of the detected light.
24. A tracker array for tracking a surgical object, the tracker array comprising:
a body;
first, second, and third light sources secured to the body and arranged in a pattern for being recognized by a navigation system to track the surgical object;
a battery mount secured to the body and including battery contacts for engaging a battery and communicating electrical energy from the battery to the first, second, and third light sources when the battery is secured to the battery mount; and
a control circuit coupled to the battery and to the first, second, and third light sources, the control circuit being configured to limit current through each of the first, second, and third light sources to less than 20 milliamps,
wherein, optionally, the first, second, and third light sources are infrared light emitting diodes.
25. A tracker array for tracking a surgical object, the tracker array comprising:
a body;
first, second, and third light sources secured to the body and arranged in a pattern for being recognized by a navigation system to track the surgical object;
a battery mount secured to the body and including battery contacts for engaging a battery and communicating electrical energy from the battery to the first, second, and third light sources when the battery is secured to the battery mount; and
a control circuit coupled to the battery and to the first, second, and third light sources, the control circuit being configured to limit an intensity of each of the first, second, and third light sources to less than 40 μW/sr,
wherein, optionally, the first, second, and third light sources are infrared light emitting diodes.
26. The tracker array of clause 24 or 25, wherein the first, second, and third light sources are each configured to emit light with a wavelength between 800 nm and 900 nm, and
wherein, optionally, the first, second, and third light sources are each configured to emit light with a wavelength between 850 and 860 nm.
27. The tracker array of any one of clauses 24-26, wherein the first, second, and third light sources are connected in series.
28. The tracker array of any one of clauses 24-27, wherein the control circuit includes a feedback circuit configured to limit the current through each of the first, second, and third light sources to less than 20 milliamps,
wherein, optionally, the feedback circuit is configured to compare the current through the first, second, and third light sources with a target current level that is less than 20 milliamps; and adjust the voltage applied to the first, second, and third light sources based on the comparison.
29. The tracker array of any one of clauses 24-28, wherein the control circuit is configured to limit the current through each of the first, second, and third light sources to less than 15 milliamps,
wherein, optionally, the control circuit is configured to limit the current through each of the first, second, and third light sources to less than 10 milliamps,
wherein, optionally, the control circuit is configured to limit the current through each of the first, second, and third light sources to less than 10 milliamps,
wherein, optionally, wherein the control circuit is configured to limit current through each of the first, second, and third light sources to less than 4 milliamps,
wherein, optionally, the control circuit is configured to maintain the current through each of the first, second, and third light sources to a level greater than 2 milliamps,
wherein, optionally, the control circuit is configured to maintain the current through each of the first, second, and third light sources at approximately 3 milliamps.
30. The tracker array of any one of clauses 24-29, further comprising a user switch for controlling the flow of energy from the battery to the first, second, and third light sources,
wherein, optionally, the user switch is a one-use switch.
31. The tracker array of clause 30, wherein the user switch is a removable insulative member positioned between the battery contacts and the battery.
32. The tracker array of any one of clauses 24-31, wherein the body is a board including a first face and an opposed second face, the first, second, and third light sources are disposed on the first face of the board, and the battery mount is disposed on the second face of the board,
wherein, optionally, the control circuit is disposed on the second face of the board.
33. The tracker array of clause 32, wherein the board includes a central portion and first, second, and third legs each extending from the central portion, and the first, second, and third light sources are mounted to distal end portions of the first, second, and third legs respectively,
wherein, optionally, the distal end portions of the first, second, and third legs are each less than 3 millimeters thick.
34. The tracker array of clause 32 or 33, wherein the board includes a surface extending between the first and second faces for being gripped by a user to mount the tracker array to the surgical object.
35. The tracker array of any one of clauses 32-34, wherein the board is not contained within a housing.
36. The tracker array of any one of clauses 32-35, wherein the board is a printed circuit board including traces connecting the first, second and third light sources, the control circuit, and the battery,
wherein. optionally, the printed circuit board is a double-layer circuit board.
37. The tracker array of clause 36, wherein the first face of the printed circuit board includes first traces connecting the first, second, and third light sources to each other, and the second face of the printed circuit board includes second traces connecting the control circuit to the battery contacts and to the first, second, and third light sources.
38. The tracker array of clause 36 or 37, further comprising a conforming protective coating covering the printed circuit board, the first, second, and third light sources, and/or the control circuit, wherein, optionally, the tracker array further comprises a battery secured to the battery mount, and the conforming protective coating also covers the battery.

39. A tracker array for tracking a surgical object, the tracker array comprising:

a board including a first face and an opposed second face;

first, second, and third light sources disposed on the first face of the board and arranged in a pattern for being recognized by a navigation system to track the surgical object; and a battery mount disposed on the second face of the board and including battery contacts for engaging a battery and communicating electrical energy from the battery to the first, second, and third light sources when the battery is secured to the battery mount, wherein, optionally, a control circuit is disposed on the second face of the board and configured to regulate the current applied to the first, second, and third light sources.

40. A disposable tracker for tracking a surgical object during a surgical procedure, the disposable tracker being removably couplable to a tracker mount secured to the surgical object, the tracker mount defining a star-shaped recess for receiving the disposable tracker, the star-shaped recess including first, second, and third leg recesses that extend distally from a central portion of the star-shaped recess, the disposable tracker comprising:

a body having a shape conforming to the star-shaped recess, the body including first, second, and third portions for being positioned adjacent distal end portions of the first, second, and third leg recesses respectively when the disposable tracker is secured to the tracker mount;

first, second, and third light sources disposed on the first, second, and third portions respectively and arranged in a pattern for being recognized by a navigation system to track the surgical object; and a battery mounted to the body and in electrical communication with the first, second, and third light sources, wherein the disposable tracker is configured for single use, and wherein, optionally, the battery is permanently secured to the body.

41. The disposable tracker of clause 40, wherein the first, second, and third portions are each less than 3 millimeters thick.

42 The disposable tracker of clause 40 or 41, wherein the disposable tracker is defined as the tracker array of any one of clauses 24-39.

43. A tracking array that is removably couplable to a tracking array mount for tracking a surgical object using a navigation system, the tracking array comprising:

a circuit board defining a central body portion and a plurality of legs extending from the central body portion, the plurality of legs including a first leg, a second leg, a third leg, and a fourth leg, the circuit board including a first face, and a second face, the first face being opposite the second face;

the central body portion having a center and defining an alignment aperture, the alignment aperture offset from the center of the central body portion;

a first light source coupled to the first leg, a second light source coupled to the second leg, a third light source coupled to the third leg, a fourth light source coupled to the fourth leg, the first, the second, the third light source, and the fourth light source extending from the first face of the circuit board;

a control circuit coupled to the circuit board;

a plurality of electrical traces printed on the circuit board, and connected to the first, second, third, and fourth light sources, and the control circuit;

a battery mount shaped to engage a battery, the battery mount coupled to the second face of the circuit board and in electrical communication with each of the light sources;

wherein the first leg, the second leg, the third leg, and the fourth leg each includes a foot portion at a distal end of the respective leg, the foot portions of the third leg and the fourth leg being shaped to align the tracking array with a tracking array mount; and a protrusion extending from the central body portion between the third leg and the fourth leg, the protrusion protruding from the central body portion for a length less than the length the third and fourth legs protrude from the central body portion, wherein, optionally, at least one of the first, second, third, and fourth light sources comprises an LED.

44. The tracking array of clause 43, further comprising a battery coupled to the battery mount, wherein, optionally, the control circuit is configured to limit the current from the battery to less than 20 mA, wherein, optionally, the control circuit is configured to limit the current from the battery to less than 10 mA, wherein, optionally, the control circuit is configured to limit the current from the battery to less than 5 mA.

45. The tracking array of clause 43 or 44, wherein the first, second, third, and fourth light sources are each configured to emit a wavelength between 800 and 900 nm.

46. The tracking array of any one of clauses 43-45, wherein the control circuit is configured to limit the intensity of each of the first, second, third, and fourth light sources to less than 40 uW/sr.

47. The tracking array of any one of clauses 43-46, further comprising an aperture defined in the central body portion of the circuit board, the aperture shaped to receive a pin of the tracking array mount.

48. The tracking array of any one of clauses 43-47, wherein the foot portion of at least one of the first leg or the second leg are shaped differently from the foot portion of the third leg and/or the fourth leg to align the tracking array with a tracking array mount.

49. The tracking array of any one of clauses 43-48, wherein the foot portion of each of the first and the second legs comprises lateral surface extending between the first and the second face of the circuit board, the lateral surface comprising at least one chamfer extending between an end face of the foot portion and a side surface of the foot portion.

50. The tracking array of any one of clauses 43-49, wherein the protrusion is unitarily formed as part the central body portion of the circuit board.

51. The tracking array of any one of clauses 43-50, wherein the light sources are arranged to define segments interconnecting each of the light sources, such that the segments differ in length from one another by at least 1 mm.

52. A tracking array for tracking a surgical object, the tracking array comprising:

a base defining a central portion and a plurality of legs extending from the central portion, the plurality of legs including a first leg, a second leg, a third leg, and a fourth leg, and the base including a first face and a second face, the first face being opposite the second face;

the central portion having a center and defining an alignment aperture, the alignment aperture offset from the center of the central portion;

a first light source coupled to the first leg, a second light source coupled to the second leg, a third light source coupled to the third leg, a fourth light source coupled to the fourth leg, the first, the second, the third, and the fourth light sources disposed on the first face of the base;

a control circuit coupled to the base;

an electrical conductor coupled to the base and connected to the first light source and the control circuit;

a battery mount including a plurality of battery contacts shaped to engage a battery upon coupling of the battery to the battery mount, the battery mount coupled to the second face of the base; and a protrusion extending from the central portion of the base between the third leg and the fourth leg, the protrusion protruding from the central portion for a length less than the length the third and fourth legs protrude from the central portion, wherein the first leg, the second leg, the third leg, and the fourth leg each includes a foot portion at a distal end of the respective leg, the foot portion of the third leg and the fourth leg being shaped to align the tracking array with a tracking array mount.

53. A package of tracking arrays for use with a surgical navigation system to identify a pose of one or more surgical objects, the package of tracking arrays comprising:

a package comprising a first portion and a second portion, the package defining a sterile volume, and the first portion and second portion separable from one another to provide access to the sterile volume;

a first tracking array including a first light source, second light source, third light source, and a fourth light source coupled to the first tracking array, the first tracking array disposed within the sterile volume, and the first tracking array comprising a battery; and a second tracking array including a first light source, second light source, third light source, and a fourth light source coupled to the second tracking array, the second tracking array comprising a second battery, wherein each of the first tracking array and the second tracking array include a circuit board including a first leg, a second leg, a third leg, and a fourth leg, wherein the first light source of each of the first tracking array and the second tracking array is disposed on the first leg at a reference location, wherein the second light source, the third light source, and the fourth light source of the first tracking array are arranged to define a plurality of triangles using the first light source and any two of the second light source, the third light source, and the fourth light source as a first pattern that is identifiable by a surgical navigation system, wherein the second light source, the third light source, and the fourth light source of the second tracking array are arranged to define a plurality of triangles using the first light source and any two of the second light source, the third light source, and the fourth light source as a second pattern that is identifiable by the surgical navigation system, and wherein the first pattern is distinguishable by the navigation system from the second pattern to allow the surgical navigation system to distinguish between each of one or more surgical objects that the first tracking array and the second tracking array are coupled to.

54. The package of tracking arrays of clause 53, wherein the first tracking array is assigned to a first surgical instrument; and wherein the second tracking array is assigned to a second surgical instrument.

55. The package of tracking arrays of clause 53 or 54, further comprising a third tracking array including three or more of light source arranged to define one or more triangles as a third pattern that is identifiable by the surgical navigation system, the third tracking array assigned to a third surgical instrument; and wherein the third pattern is distinguishable by the navigation system from the first pattern and the second pattern to allow the surgical navigation system to identify the third surgical instrument.

56. The package of tracking arrays of any one of clauses 53-55, further comprising a base defining a cavity for supporting each of the first tracking array and the second tracking array and a film for covering the cavity for storing the first tracking array and the second tracking array in a sterile state until ready for use during a surgical procedure.

57. A method of attaching a tracking array to a tracker mount of a surgical object for use with a surgical navigation system, the method comprising:

providing a tracker array comprising a central body portion, a plurality of legs extending from the central body portion, each of the plurality of legs comprising a foot portion located spaced apart from the central body portion, and a plurality of light sources coupled to the plurality of legs;

inserting the foot portions of two of the plurality of legs within respective recesses of the tracker mount of the surgical object; and manipulating a locking mechanism of the tracker mount to removably secure the tracking array to the tracker mount after the foot portions are inserted within the respective recesses of the tracker mount, wherein, optionally, the method further comprises removing an insulator from between a battery terminal of a battery mount on the tracker array and a battery disposed in the battery mount to allow electrical connection between the battery and the battery terminal.

58. The method of clause 57, wherein the step of inserting at least one of the plurality of legs in coupling feature of a tracker mount further comprises positioning a first leg having a first foot portion within a first coupling feature of the tracker mount and positioning a second leg having a second foot portion within a second coupling feature of the tracker mount; and wherein each of the first and second foot portions are shaped differently and configured to engage the respective first and second coupling feature of the tracker mount.

59. A method of manufacturing a kit of tracking arrays, the method comprising:

providing at least two circuit boards, each of the circuit boards comprising a central body portion and a plurality of legs extending from the central body portion arranged such that each of the at least two circuit boards comprises a generally identical shape;

attaching three or more light sources to a first of the at least two circuit boards, each of the three or more light sources coupled to one of the plurality of legs extending from the central body portion to define a first pattern;

attaching three or more light sources to a second of the at least two circuit boards, each of the three or more light sources coupled to one of the plurality of legs extending from the central body portion to define a second pattern; and packaging the first and second of the at least two circuit boards in a single sterile container in preparation for use during a surgical procedure including two or more surgical objects, each of which utilizes a universal tracker mount and the first pattern or the second pattern to allow a navigation system to distinguish between each of the two or more surgical tracking arrays, wherein, optionally, the method further comprises applying a protective coating to an exterior surface of each of the at least two circuit boards.

60. A tracking array for tracking a surgical object using a navigation system, the tracking array comprising:

a central body portion and a plurality of legs extending from the central body portion, the plurality of legs including a first leg, a second leg, a third leg, and a fourth leg, and the central body portion including a first face and a second face, the first face being opposite the second face;

the central body portion having a center and defining an alignment aperture, the alignment aperture offset from the center of the central body portion;

a first light source coupled to the first leg, a second light source coupled to the second leg, a third light source coupled to the third leg, a fourth light source coupled to the fourth leg, the first, the second, the third, and the fourth light sources are disposed on the first face of the central body portion;

a control circuit in communication with the first, second, third, and fourth light sources and configured to limit the current to the light sources such that the first, second, third, and fourth light sources emit light at an intensity capable of being observed by the navigation system;

a battery mount shaped to engage a battery, the battery mount coupled to the second face of the central body portion; and a protrusion extending from the central body portion between the third leg and the fourth leg, the protrusion protruding from the central body portion for a length less than the length the third and fourth legs protrude from the central body portion, wherein each of the first leg, the second leg, the third leg, and the fourth leg includes a foot portion at a distal end of the respective leg, the foot portions of the first leg and the second leg being shaped to align the tracking array with a tracking array mount, and wherein, optionally, each of the first, second, third, and fourth light sources are positioned proximate a distal end of the first, second, third, and fourth legs respectively.

61. The tracking array of clause 60, further comprising a battery disposed in the battery mount, the battery connected to battery terminals to form electrical connection with each of the first light source, the second light source, and the third light source.

62. A tracking array removably couplable to a tracking array mount for use with a navigation system to identify a pose of a surgical instrument, the tracking array comprising:

a circuit board including a first surface and an opposed second surface, the circuit board shaped to define a first leg, a second leg, and a third leg;

a first light source disposed on the first surface of the first leg;

a second light source disposed on the first surface of the second leg;

a third light source disposed on the first surface of the third leg; and a battery mount disposed on the second surface of the circuit board, the battery mount including battery terminals in electrical communication with each of the first light source, the second light source, and the third light source, wherein a combination of the first light source, the second light source, and the third light source are configured to define a visual indicia specific to the surgical instrument and identifiable by the navigation system, and wherein, optionally, the circuit board if further shaped to define a fourth leg and including a fourth light source disposed on the first surface of the fourth leg.

63. The tracking array of clause 62, wherein the circuit board if further shaped to define a fourth leg and including a fourth light source disposed on the first surface of the fourth leg.

64. A tracking array for tracking a surgical object using a navigation system, the tracking array comprising:

a central body portion and a plurality of legs extending from the central body portion, the plurality of legs including a first leg, a second leg, a third leg, and a fourth leg, the central body portion including a first face, and a second face, the first face being opposite the second face;

the central body portion having a center and defining an alignment aperture, the alignment aperture offset from the center of the central body portion;

a first light source coupled to the first leg, a second light source coupled to the second leg, a third light source coupled to the third leg, a fourth light source coupled to the fourth leg, the first, the second, the third, and the fourth light sources are disposed on the first face of the central body portion;

a control circuit in communication with the first, second, third, and fourth light sources and configured to limit the current to the light sources such that the first, second, third, and fourth light sources emit light at an intensity capable of being observed by the navigation system; and a battery mount shaped to engage a battery and coupled to the second face of the central body portion, wherein each of the first leg, the second leg, the third leg, and the fourth leg each include a foot portion at a distal end of the respective leg, the foot portions of the first leg and the second leg being shaped to align the tracking array with a tracking array mount.

65. A tracking array for tracking a surgical object, the tracking array comprising:

a base defining a central portion and a plurality of legs extending from the central portion, the plurality of legs including a first leg, a second leg, a third leg, and a fourth leg, the base including a first face, and a second face, the first face being opposite the second face;

a first light source coupled to the first leg, a second light source coupled to the second leg, a third light source coupled to the third leg, a fourth light source coupled to the fourth leg, the first, the second, the third, and the fourth light sources disposed on the first face of the base;

a control circuit coupled to the base;

an electrical conductor coupled to the base and connected to the first light source and the control circuit; and a battery mount including a plurality of battery contacts shaped to engage a battery upon coupling of the battery to the battery mount, the battery mount coupled to the second face of the base, wherein the first leg, the second leg, the third leg, and the fourth leg each include a foot portion at a distal end of the respective leg, the foot portion of the third leg and the fourth leg being shaped to align the tracking array with a tracking array mount, and wherein the foot portion of at least one of the first leg or the second leg comprises an indicia that distinguishes the foot portion from the remaining portion of the base.

66. The tracking array of clause 65, wherein, the tracking array further comprises a protrusion extending from the central portion of the base between the third leg and the fourth leg, the protrusion protruding from the central portion for a length less than the length the third and fourth legs protrude from the central portion, and wherein, optionally, the protrusion further comprises a second indicia that distinguishes the protrusion from the remaining portion of the base.

67. The tracking array of clause 65 or 66, wherein both of the foot portions of the first leg and the second leg comprise the indicia that distinguishes the foot portion from the remaining portion of the base.

68. The tracking array of any one of clauses 64-67, wherein the indicia and/or the second indicia is configured to assist the user in properly positioning the base within a tracking array mount of a surgical instrument.

69. The tracking array of any one of clauses 64-67, wherein the indicia and/or the second indicia is visually perceivable by the user and/or a surgical navigation system.

What is claimed is:

1. A surgical instrument assembly for removably coupling a tracker to a surgical handpiece, the surgical instrument assembly comprising:

an end effector comprising:

a shaft comprising a distal portion and opposing proximal portion, the distal portion for manipulating biological tissue and the proximal portion defining a coupling feature for removably attaching the end effector to the surgical handpiece; and a reference feature disposed on the shaft between the proximal portion and the distal portion, the reference feature spaced a defined distance from the coupling feature; and an adapter removably couplable to the end effector, the adapter comprising:

a proximal member comprising a surgical handpiece interface configured to engage the surgical handpiece and prevent rotation of the proximal member relative to the surgical handpiece;

a distal member rotatably and slidably coupled to the proximal member, wherein the distal member further comprises a tracking array mount for coupling a tracker to the adapter; and a biasing member positioned to urge the proximal member and the distal member in opposing directions, wherein the proximal member and the distal member define an aperture through the adapter that is configured to receive the shaft of the end effector, and wherein the coupling feature and the reference feature of the end effector are spaced along the shaft of the end effector such that the surgical handpiece will engage the proximal member of the adapter and the reference feature will engage the distal member of the adapter when the end effector is coupled to the surgical handpiece causing the biasing member to create a frictional force between the proximal member and the distal member that resists rotation of the distal member relative to the proximal member.

2. The surgical instrument assembly of claim 1, wherein the frictional force inhibits rotation of the distal member relative to the proximal member absent an external force being applied to the distal member.

3. The surgical instrument assembly of claim 1, wherein the distal member further comprises a fastening member configured to removably secure the adapter to the shaft of the end effector when the end effector is decoupled from the surgical handpiece.

4. The surgical instrument assembly of claim 3, wherein the fastening member comprises a detent configured to selectively engage an annular recess defined in an outer surface of the shaft of the end effector to removably secure the adapter to the end effector.

5. The surgical instrument assembly of claim 3, wherein the fastening member for removably securing the adapter to the shaft of the end effector is configured to allow rotation of the end effector relative to the distal member.

6. The surgical instrument assembly of claim 3, further comprising a calibration body having a known length and configured to be identifiable by a surgical navigation system, the calibration body further including an adapter interface comprising a retention feature configured to matingly engage the fastening member of the adapter to removably attach the adapter to the calibration body at a known position relative to a distal end of the calibration body.

7. The surgical instrument assembly of claim 6, wherein the retention feature of the calibration body is configured to position the adapter a first distance from the distal end of the calibration body, wherein the reference feature of the end effector is configured to position the adapter a second distance from a distal end of the end effector, and wherein the first distance is equal to the second distance.

8. The surgical instrument assembly of claim 1, wherein the biasing member is disposed between the proximal member and the distal member.

9. The surgical instrument assembly of claim 1, wherein the proximal member and the distal member of the adapter are configured to generate a compressive force on the biasing member when the adapter is coupled to the end effector and the surgical handpiece interface of the proximal member is engaged with the surgical handpiece.

10. The surgical instrument assembly of claim 1, wherein the surgical handpiece interface comprises one or more protrusions configured to mate with a reciprocal feature on the surgical handpiece when the adapter is coupled to the end effector and the surgical handpiece interface is engaged with the surgical handpiece.

11. The surgical instrument assembly of claim 1, wherein the biasing member is configured to urge the proximal member toward the surgical handpiece when the adapter is coupled to the end effector and the surgical handpiece interface is engaged with the surgical handpiece.

12. The surgical instrument assembly of claim 1, wherein the proximal member is axially movable relative to the distal member between an engaged position when the surgical handpiece interface is engaged with the surgical handpiece and a free position when the surgical handpiece interface is separated from the surgical handpiece, such that:

the biasing member is compressed when the proximal member is in the engaged position creating a frictional force between the proximal and distal members of the adapter that inhibits rotation of the distal member relative to the proximal member absent an external force being applied to the distal member; and the biasing member is decompressed when the proximal member is in the free position allowing the distal member to rotate freely relative to the proximal member.

13. The surgical instrument assembly of claim 1, wherein the biasing member is a wave spring.

14. The surgical instrument assembly of claim 1, wherein the end effector is a first end effector and comprises a twist drill, and the surgical instrument assembly further comprising a second end effector, the second end effector being a screwdriver.

15. The surgical instrument assembly of claim 1, wherein the biasing member is disposed between the proximal member and the distal member, and further comprising a tapered washer disposed between the biasing member and the proximal member and including a beveled surface configured to contact a reciprocal surface of the proximal member to create a sliding friction that resists rotation of the distal member relative to the proximal member when the adapter is disposed on the end effector and the surgical handpiece interface of the proximal member is engaged with the surgical handpiece.

16. The surgical instrument assembly of claim 15, wherein the tapered washer is configured to wedge between the distal member and the proximal member to create the sliding friction that resists rotation of the distal member relative to the proximal member when the adapter is disposed on the end effector and the surgical handpiece interface of the proximal member is engaged with the surgical handpiece.

17. A surgical instrument adapter for use with a calibration body including a stop and a retention feature, the surgical instrument adapter comprising:

a proximal member comprising a surgical handpiece interface configured to engage a surgical handpiece and prevent rotation of the proximal member relative to the surgical handpiece;

a distal member slidably and rotatably coupled to the proximal member;

a biasing member disposed between the proximal member and the distal member and configured to urge the proximal member and distal member in opposing directions;

a tracking array mount coupled to the distal member; and a fastening member disposed on the distal member and configured to removably secure the adapter to the calibration body, the fastening member shaped to matingly engage the retention feature of the calibration body such that the distal member abuts the stop of the calibration body to position the adapter at a known distance from a distal end of the calibration body.

18. The surgical instrument adapter of claim 17, wherein the fastening member comprises a protrusion and the retention feature of the calibration body comprises an annular recess defined in a shaft of the calibration body, and wherein the protrusion and the annular recess are reciprocally shaped to prevent lateral movement of the distal member of the adapter along the shaft of the calibration body while allowing rotation of the distal member of the adapter about the shaft of the calibration body.

19. A surgical instrument adapter for use with an end effector including a reference feature and an attachment feature for coupling the end effector to a surgical handpiece, the surgical instrument adapter comprising:

a proximal member comprising a surgical handpiece interface configured to engage the surgical handpiece and prevent rotation of the proximal member relative to the surgical handpiece;

a distal member slidably and rotatably coupled to the proximal member;

a biasing member disposed between the proximal member and the distal member and configured to urge the proximal member and distal member in opposing directions;

a tracking array mount coupled to the distal member; and a fastening member disposed on the distal member and configured to removably secure the adapter to the end effector such that the end effector can rotate freely relative to the distal and proximal members, wherein the biasing member is configured to be compressed by the reference feature and the surgical handpiece acting upon the distal member and the proximal member when the end effector is coupled to the surgical handpiece, the biasing member creating a friction force between the distal member and the proximal member that resists rotation of the distal member relative to the proximal member, and wherein the biasing member is configured to be decompressed when the end effector is decoupled from the surgical handpiece allowing the distal member to rotate freely relative to the proximal member.

20. The surgical instrument adapter of claim 19, wherein the proximal member is axially movable relative to the distal member between an engaged position when the surgical handpiece interface is engaged with the surgical handpiece and a free position when the surgical handpiece interface is separated from the surgical handpiece, such that:

when the proximal member is in the engaged position the biasing member is compressed creating a friction force between the proximal member and the distal member that inhibits rotation of the distal member relative to the proximal member absent application of an external force to the adapter; and when the proximal member is in the free position the biasing member is decompressed allowing the distal member to rotate freely relative to the proximal member.

* * * * *